United States Patent
Arnold et al.

(10) Patent No.: US 6,537,746 B2
(45) Date of Patent: Mar. 25, 2003

(54) METHOD FOR CREATING POLYNUCLEOTIDE AND POLYPEPTIDE SEQUENCES

(75) Inventors: Frances Arnold, Pasadena, CA (US); Zhixin Shao, Penzberg, DE (US); Alexander Volkov, South Pasadena, CA (US)

(73) Assignee: Maxygen, Inc., Redwood City, CA (US)

( * ) Notice: Subject to any disclaimer, the term of this patent is extended or adjusted under 35 U.S.C. 154(b) by 132 days.

(21) Appl. No.: 09/205,448

(22) Filed: Dec. 4, 1998

(65) Prior Publication Data

US 2002/0137661 A1 Sep. 26, 2002

Related U.S. Application Data

(60) Provisional application No. 60/067,908, filed on Dec. 8, 1997.

(51) Int. Cl.[7] .................................................. C12Q 1/68
(52) U.S. Cl. .................... 435/6; 435/91.1; 435/91.2; 435/69.1; 435/320.1; 536/27; 935/47
(58) Field of Search ................... 435/6, 91.1, 91.2, 435/69.1, 320.1; 536/27; 935/47

(56) References Cited

U.S. PATENT DOCUMENTS

| | | |
|---|---|---|
| 4,683,202 A | 7/1987 | Mullis |
| 4,800,159 A | 1/1989 | Mullis et al. |
| 4,816,567 A | 3/1989 | Cabilly et al. |
| 4,959,312 A | 9/1990 | Sirotkin |
| 4,965,188 A | 10/1990 | Mullis et al. |
| 4,994,368 A | 2/1991 | Goodman et al. |
| 4,994,379 A * | 2/1991 | Chang ........................ 435/69.1 |
| 5,023,171 A | 6/1991 | Ho et al. |
| 5,043,272 A | 8/1991 | Hartley |
| 5,093,257 A | 3/1992 | Gray |
| 5,106,727 A | 4/1992 | Hartley et al. |
| 5,169,764 A | 12/1992 | Shooter et al. |
| 5,176,995 A | 1/1993 | Sninsky et al. |

(List continued on next page.)

FOREIGN PATENT DOCUMENTS

| | | |
|---|---|---|
| EP | 0 252 666 | 1/1988 |
| EP | 552 266 | 1/1993 |

(List continued on next page.)

OTHER PUBLICATIONS

Andersson et al., "Muller's ratchet decreases fitness of a DNA–based microbe", *PNAS*, 93: 906–907 (Jan. 1996).

(List continued on next page.)

*Primary Examiner*—W. Gary Jones
*Assistant Examiner*—Janell E. Taylor
(74) *Attorney, Agent, or Firm*—Townsend and Townsend and Crew LLP

(57) ABSTRACT

The invention provides methods for evolving a polynucleotide toward acquisition of a desired property. Such methods entail incubating a population of parental polynucleotide variants under conditions to generate annealed polynucleotides comprising heteroduplexes. The heteroduplexes are then exposed to a cellular DNA repair system to convert the heteroduplexes to parental polynucleotide variants or recombined polynucleotide variants. The resulting polynucleotides are then screened or selected for the desired property.

42 Claims, 24 Drawing Sheets

U.S. PATENT DOCUMENTS

| | | |
|---|---|---|
| 5,187,083 A | 2/1993 | Mullis |
| 5,223,408 A | 6/1993 | Goeddel et al. |
| 5,234,824 A | 8/1993 | Mullis |
| 5,264,563 A | 11/1993 | Huse |
| 5,279,952 A | 1/1994 | Wu |
| 5,314,809 A | 5/1994 | Erlich et al. |
| 5,316,935 A | 5/1994 | Arnold et al. |
| 5,356,801 A | 10/1994 | Rambosek et al. |
| 5,360,728 A | 11/1994 | Prasher |
| 5,418,149 A | 5/1995 | Gelfand et al. |
| 5,422,266 A | 6/1995 | Cormier et al. |
| 5,470,725 A | 11/1995 | Borriss et al. |
| 5,489,523 A | 2/1996 | Mathur |
| 5,502,167 A | 3/1996 | Waldmann et al. |
| 5,512,463 A | 4/1996 | Stemmer |
| 5,514,568 A | 5/1996 | Stemmer |
| 5,521,077 A | 5/1996 | Khosla et al. |
| 5,523,388 A | 6/1996 | Huse |
| 5,541,309 A | 7/1996 | Prasher |
| 5,556,750 A | 9/1996 | Modrich et al. |
| 5,556,772 A | 9/1996 | Sorge et al. |
| 5,571,708 A | 11/1996 | Yang et al. |
| 5,605,793 A | 2/1997 | Stemmer |
| 5,629,179 A | 5/1997 | Mierendorf et al. |
| 5,652,116 A | 7/1997 | Grandi et al. |
| 5,679,522 A | 10/1997 | Modrich et al. |
| 5,698,426 A | 12/1997 | Huse |
| 5,714,316 A | 2/1998 | Weiner et al. |
| 5,723,323 A | 3/1998 | Kauffman et al. |
| 5,756,316 A | 5/1998 | Schellenberger |
| 5,763,192 A | 6/1998 | Kauffman et al. |
| 5,770,434 A | 6/1998 | Huse |
| 5,773,267 A | 6/1998 | Jacobs et al. |
| 5,783,431 A | 7/1998 | Peterson et al. |
| 5,795,747 A | 8/1998 | Henco et al. |
| 5,808,022 A | 9/1998 | Huse |
| 5,811,238 A | 9/1998 | Stemmer et al. |
| 5,814,476 A | 9/1998 | Kauffman et al. |
| 5,817,483 A | 10/1998 | Kauffman et al. |
| 5,824,469 A | 10/1998 | Horwitz et al. |
| 5,824,485 A | 10/1998 | Thompson et al. |
| 5,824,514 A | 10/1998 | Kauffman et al. |
| 5,830,696 A | 11/1998 | Short |
| 5,830,721 A | 11/1998 | Stemmer et al. |
| 5,834,252 A | 11/1998 | Stemmer et al. |
| 5,837,458 A | 11/1998 | Minshull et al. |
| 5,843,643 A | 12/1998 | Ratner |
| 5,851,813 A | 12/1998 | Desrosiers |
| 5,858,725 A | 1/1999 | Crowe et al. |
| 5,866,363 A | 2/1999 | Pieczenik |
| 5,871,974 A | 2/1999 | Huse |
| 5,877,402 A | 3/1999 | Maliga et al. |
| 5,928,905 A | 7/1999 | Stemmer et al. |
| 5,939,250 A | 8/1999 | Short |
| 5,955,358 A | 9/1999 | Huse |
| 5,958,672 A | 9/1999 | Short |
| 5,965,408 A | 10/1999 | Short |
| 5,965,415 A | 10/1999 | Radman et al. |
| 5,976,862 A | 11/1999 | Kauffman et al. |
| 6,001,574 A | 12/1999 | Short et al. |
| 6,004,788 A | 12/1999 | Short |
| 6,030,779 A | 2/2000 | Short |
| 6,051,409 A | 4/2000 | Hansen et al. |
| 6,054,267 A | 4/2000 | Short |
| 6,057,103 A | 5/2000 | Short |
| 6,071,889 A | 6/2000 | Weiss et al. |
| 6,074,853 A | 6/2000 | Pati et al. |
| 6,087,177 A | 7/2000 | Wohlstadter |
| 6,087,341 A | 7/2000 | Khavari et al. |
| 6,093,873 A | 7/2000 | Chambon et al. |
| 6,096,548 A | 8/2000 | Stemmer |
| 6,103,463 A * | 8/2000 | Chetverin et al. ............ 435/6 |
| 6,117,679 A | 9/2000 | Stemmer |
| 6,132,970 A | 10/2000 | Stemmer |
| 6,165,793 A | 12/2000 | Stemmer |
| 6,168,919 B1 | 1/2001 | Short |
| 6,171,820 B1 | 1/2001 | Short |
| 6,174,673 B1 | 1/2001 | Short et al. |
| 6,180,406 B1 | 1/2001 | Stemmer |

FOREIGN PATENT DOCUMENTS

| | | |
|---|---|---|
| EP | 544 809 B1 | 12/1998 |
| EP | 563 296 B1 | 3/1999 |
| WO | WO 90/07576 | 7/1990 |
| WO | WO 90/14424 | 11/1990 |
| WO | WO 90/14430 | 11/1990 |
| WO | WO 91/01087 | 2/1991 |
| WO | WO 91/06570 | 5/1991 |
| WO | WO 91/06643 | 5/1991 |
| WO | WO 91/06645 | 5/1991 |
| WO | WO 91/07506 | 5/1991 |
| WO | WO 91/15581 | 10/1991 |
| WO | WO 91/16427 | 10/1991 |
| WO | WO 92/06176 | 4/1992 |
| WO | WO 92/07075 | 4/1992 |
| WO | WO 92/18645 | 10/1992 |
| WO | WO 93/01282 | 1/1993 |
| WO | WO 93/02191 | 2/1993 |
| WO | WO 93/06213 | 4/1993 |
| WO | WO 93/11237 | 6/1993 |
| WO | WO 93/12228 | 6/1993 |
| WO | WO 93/15208 | 8/1993 |
| WO | WO 93/16192 | 8/1993 |
| WO | WO 93/18141 | 9/1993 |
| WO | WO 93/19172 | 9/1993 |
| WO | WO 93/25237 | 12/1993 |
| WO | WO 94/03596 | 2/1994 |
| WO | WO 94/09817 | 5/1994 |
| WO | WO 94/11496 | 5/1994 |
| WO | WO 94/13804 | 6/1994 |
| WO | WO 95/17413 | 6/1995 |
| WO | WO 95/22625 | 8/1995 |
| WO | WO 96/17056 | 6/1996 |
| WO | WO 96/33207 | 10/1996 |
| WO | WO 97/07205 | 2/1997 |
| WO | WO 97/20078 | 6/1997 |
| WO | WO 97/25410 | 7/1997 |
| WO | WO 97/35966 | 10/1997 |
| WO | WO 98/01581 | 1/1998 |
| WO | WO 98/27230 | 6/1998 |
| WO | WO 98/28416 | 7/1998 |
| WO | WO 98/41622 | 9/1998 |
| WO | WO 98/41623 | 9/1998 |
| WO | WO 98/41653 | 9/1998 |
| WO | WO 98/42832 | 10/1998 |
| WO | WO 99/29902 | 6/1999 |
| WO | WO 00/04190 | 1/2000 |
| WO | WO 00/06718 | 2/2000 |
| WO | WO 00/09727 | 2/2000 |
| WO | WO 00/18906 | 4/2000 |

OTHER PUBLICATIONS

Bailey, "Toward a Science of Metabolic Engineering", *Science*, 252: 1668–1680 (1991).

Barrett et al., "Genotypic analysis of multiple loci in somatic cells by whole genome amplification", *Nuc. Acids Res.*, 23(17): 3488–3492 (1995).

Cameron et al., "Cellular and Metabolic Engineering An Overview", *Applied Biochem. Biotech.*, 38: 105–140 (1993).

Chakrabarty, "Microbial Degradation of Toxic Chemicals: Evolutionary Insights and Practical Considerations", *ASM News*, 62(3): 130–137 (1996).

Chater, "The Improving Prospects for Yield Increase by Genetic Engineering in Antibiotic–Producing Streptomycetes", *Biotechnology*, 8: 115–121 (Feb. 1990).

Chen et al., "Tuning the activity of an enzyme for unusual environments: Sequential random mutagenesis of subtilisin E for catalysis in dimethylformamide", *PNAS*, 90: 5618–5622 (Jun. 1993).

Dieffenbach et al., *PCR Primer, A Laboratory Manual*, Cold Spring Harbor Laboratory Press, pp. 583–589, 591–601, 603–612, and 613–621 (1995).

Evnin et al., "Substrate specificity of trypsin investigated by using a genetic selection", *PNAS*, 87: 6659–6663 (Sep. 1990).

Ippolito et al. "Structure assisted redesign of a protein–zinc–binding site with femtomolar affinity", *PNAS*, 92: 5017–5021 (May 1995).

Kellogg et al., "Plasmid–Assisted Molecular Breeding: New Technique for Enhanced Biodegradation of Persistent Toxic Chemicals", *Science*, 214: 1133–1135 (Dec. 4, 1981).

Kunkel, "Rapid and efficient site–specific mutagenesis without phenotypic selection", *PNAS*, 82: 488–493 (Jan. 1985).

Levichkin et al., "A New Approach to Construction of Hybrid Genes: Homolog Recombination Method", *Mol. Biology*, 29(5) part 1: 572–577 (1995).

Lewis et al., "Efficient site directed in vitro mutagenesis using ampicillin selection", *Nuc. Acids Res.*, 18(12): 3439–3443 (1990).

Moore et al., "Directed evolution of a para–nitrobenzyl esterase for aqueous–organic solvents", *Nature Biotech.*, 14: 458–467 (Apr. 1996).

Omura, "Philosophy of New Drug Discovery", *Microbiol. Rev.*, 59(3): 259–279 (Sep. 1986).

Piepersberg, "Pathway Engineering in Secondary Metabolite–Producing Actinomycetes", *Crit. Rev. Biotech.*, 14(3):251–285 (1994).

Prasher, "Using GFP to see the light", *TIG*, 11(8) (Aug. 1995).

Rice et al., "Random PCR mutagenesis screening of secreted proteins by direct expression in mammalian cells", *PNAS*, 89: 5467–5471 (Jun. 1992).

Simpson et al., "Two paradigms of metabolic engineering applied to amino acid biosynthesis", *Biochem. Soc. Transactions*, vol. 23 (1995).

Steele et al., "Techniques for Selection of Industrially Important Microorganisms", *Ann. Rev. Microbiol.*, 45: 89–106 (1991).

Stephanopoulos et al., "Metabolic engineering—methodologies and future prospects", *Trends Biotech.* 11: 392–396 (1993).

Stephanopoulos, "Metabolic engineering", *Curr. Opin. Biotech.*, 5: 196–200 (1994).

Wehmeier, "New multifunctional *Escherichia coli*–Streptomyces shuttle vectors allowing blue–white screening on XGal plates", *Gene*, 165: 149–150 (1995).

Atreya et al., "Construction of in–frame chimeric plant genes by simplified PCR strategies," *Plant Mol. Biol.*, 19:517–522 (1992).

Bock et al., "Selection of single–stranded DNA molecules that bind and inhibit human thrombin," *Nature*, 355:564–566 (Feb. 2, 1992).

Clackson et al., "Making antibody fragments using phage display libraries," *Nature*, 352:624–628 (Aug. 15, 1991).

Crameri et al., "10(20)–Fold aptamer library amplification without gel purification," *Nuc. Acids Res.*, 21(18):4410 (1993).

Cull et al., "Screening for receptor ligands using libraries of peptides linked to the C terminus of the lac repressor," *PNAS*, 89:1865–1869 (Mar. 1992).

Cwirla et al., "Peptides on phage: A vast library of peptides for identifying ligands," *PNAS*, 87:6378–6382 (Aug. 1990).

Daugherty et al., "Polymerase chain reaction facilitates the cloning, CDR–grafting, and rapid expression of a murine monoclonal antibody directed against the CD18 component of leukocyte integrins," *Nuc. Acids Res.*, 19(9):2471–2476 (1991).

Delagrave et al., "Searching Sequence Space to Engineer Proteins: Exponential Ensemble Mutagenesis," *Biotechnology*, 11:1548–1552 (Dec. 1993).

Dube et al., "Artificial mutants Generated by the Insertion of Random Oligonucleotides into the Putative Nucleoside Binding Site of the HSV–1 Thymidine Kinase Gene," *Biochemistry*, 30(51):11760–11767 (1991).

Fullen et al., "Genetic Algorithms and Recursive Ensemble Mutagenesis in Protein Engineering," *Complexity Int.'l 1994 I*, printed from website http://www.csu.edu.au/ci/vol1/fuellen/REM.html on Dec. 7, 1999.

Ghosh et al., "Arginine–395 Is Required for Efficient in Vivo and in Vitro Aminoacylation of tRNAs by *Escherichia coli* Methionyl–tRNA Stnthetase," *Biochemistry*, 30:11767–11774 (1991).

Goldman et al., "An Algorithmically Optimized Combinatorial Library Screened by digital Imaging Spectroscopy," *Biotechnology*, 10:1557–1561 (Dec. 1992).

Harlow et al., "Construction of Linker–Scanning Mutations using the Polymerase Chain Reaction," *Methods in Mol. Biol.*, 31:87–96 (1994).

Heda et al., "A simple in vitro site directed mutagenesis of concatamerized cDNA by inverse polymerase chain reaction," *Nuc. Acids Res.*, 20(19):5241–5242 (1992).

Ho et al., "DNA and Protein Engineering Using the Polymerase Chain Reaction: Splicing by Overlap Extension," *DNA and Protein Eng. Techniques*, 2(2):50–55 (1990).

Hodgson, "The Whys and Wherefores of DNA Amplification," *Biotechnology*, 11:940–942 (Aug. 1993).

Horton et al., "Gene Splicing by Overlap Extension," *Mehtods in Enzymology*, 217:270–279 (1993).

Horton et al., "Gene Splicing by Overlap Extension: Tailor–Made Genes Using the Polymerase chain Reaction," *BioTechniques*, 8(5):528–535 (May 1990).

Jayaraman et al., "Polymerase chain reaction–mediated gene synthesis: Synthesis of a gene coding for isozyme c of horseradish peroxidase," *PNAS*, 88:4084–4088 (May 1991).

Jones et al., "A Rapid Method for Recombination and Site–Specific Mutagenesis by Placing Homologous ends on DNA Using Polymerase Chain Reaction," *BioTechniques*, 10(1): 62–66 (1991).

Joyce, G. F., "Directed Molecular Evolution," *Scientific American*, (Dec. 1992).

Klug et al., "Creating chimeric molecules by PCR directed homologous DNA recombination," *Nuc. Acids Res.*, 19(10):2793 (1991).

Krishnan et al., "Direct and crossover PCR amplification to facilitate Tn5supF–based sequencing of λ phage clones," *Nuc. Acids Res.*, 19(22):6177–6182 (1991).

Lowman, H.B. et al, "Affinity Maturation of Human Growth Hormone by Monovalent Phage Display," *J. Mol. Biol.*, 234:564–578 (1993).

Majumder, K., "Ligation–free gene synthesis by PCR: synthesis and mutagenesis at multiple loci of a chimeric gene encoding OmpA signal peptide and hirudin," *Gene*, 110:89–94 (1992).

Marks et al., "By–passing Immunization, Human Antibodies from V–gene Libraries Displayed on Phage," *J. Mol. Biol.*, 222:581–597 (1991).

McCafferty et al., "Phage antibodies: filamentous phage displaying antibody variable domains," *Nature*, 348:552–554 (Dec. 6, 1990).

Morl et al., "Group II intron RNA–catalyzed recombination of RNA in vitro," *Nuc. Acids Res.*, 18(22):6545–6551 (1990).

Mullis et al., "Specific Synthesis of DNA in Vitro via a Polymerase–Catalyzed Chain Reaction," *Methods in Enzymology*, 155:335–351 (1987).

Mullis et al., "Specific Enzymatic Amplification of DNA In Vitro: The Polymerase Chain Reaction," Cold Spring Harbor Symposia on Quantitative Biology, 51:263–273 (1986).

Nissim et al., "Antibody fragments from a 'single pot' display library as immunochemical reagents," *EMBO Journal*, 13(3):692–698 (1994).

Osuna et al., "Combinatorial mutagenesis of three major groove–contacting residues of Eco RI: single and double amino acid replacements retaining methyltransferase–sensitive activities," *Gene*, 106:7–12 (1991).

Paabo et al., "DNA Damage Promotes Jumping between Templates during Enzymatic Amplification," *J. Biol. Chem.*, 265(8):4718–4721 (Mar. 15, 1990).

Robles et al., "Hydropathy and Molar Volume Constraints on Combinatorial mutants of the Photosynthetic Reaction Center," *J. Mol. Biol.*, 232:242–252 (1993).

Saiki et al., "Diagnosis of sickle Cell Anemia and β–Thalassemia with Enzymatically Amplified DNA and Nonradioactive Allele–Specific Oligonucleotide Probes," *New England J. of Medicine*, 319(9):537–541 (Sep. 1, 1988).

Saiki et al., "analysis of enzymatically amplified β–globin and HLA–DQα DNA with allele–specific oligonucleotide probes," *Nature*, 324:163–166 (Nov. 13, 1986).

Saiki et al., "Enzymatic Amplification of β–Globin Genomic Sequences and Restriction Site analysis for Diagnosis of Sickle Cell Anemia," *Science*, 230:1350–1354 (Dec. 20, 1985).

Saiki et al., "Primer–Directed Enzymatic Amplification of DNA with a Thermostabl;e DNA Polymerase," *Science*, 239:487–491 (Jan. 20, 1988).

Sambrook et al., *Molecular Cloning, A Laboratory Manual*, Cold Spring Laboratory Press, Cold Spring Harbor, New York (1989).

Scharf et al., "Direct Cloning and Sequence Analysis of Enzymatically Amplified Genomic Sequences," *Science*, 233:1076–1078 (Sep. 1986).

Scott et al., "Searching for Peptide Ligands with an Epitope Library," *Science*, 249:386–390 (Jul. 20, 1990).

Sikorski et al., "In Vitro Mutagenesis and Planned Shuffling: From Cloned Gene to Mutant Yeast," *Methods in Enzymology*, 194:302–318 (1991).

Smith et al., "Unwanted Mutations in PCR Mutagenesis: Avoiding the Predictable," *PCR Methods and Applications*, 2(3):253–257 (Feb. 1993).

Villarreal et al., "A General Method of Polymerase–Chain–Reaction–Enabled Protein Domain Mutagenesis: Construction of a Human Protein S–Osteonectin Gene," *Analytical Biochem.*, 197:362–367 (1991).

Weissenhorn et al., "Chimerization of antibodies by isolation of rearranged genomic variable regions by the polymerase chain reaction," *Gene*, 106:273–277 (1991).

Yao et al., "Site–directed Mutagenesis of Herpesvirus Glycoprotein Phosphorylation Sites by Recombination Polymerase Chain Reaction, " *PCR Methods and Applications*, 1(3):205–207 (Feb. 1992).

Yolov et al., "Constructing DNA by polymerase recombination," *Nuc. Acids Res.*, 18(13):3983–3986 (1990).

Yon et al., "Precise gene fusion by PCR," *Nuc. Acids Res.*, 17(12):4895 (1989).

Youvan et al., "Recursive Ensemble Mutagenesis: A Combinatorial Optimization Technique for Protein Engineering," from Parallel Problem Solving from Nature, 2, Manner eds., pp. 401–410 (1992).

Zoller, M.J., "New recombinant DNA methodology for protein engineering," *Curr. Opin. Biotech.*, 3:348–354 (1992).

Opposition Statement in matter of Australian Patent Application 703264 (Affymax Technologies NV), filed by Diversa Corporation on Sep. 23, 1999.

Adey et al., "Preparation of second–generation phage libraries," *Phage Disp. Pept. Proteins*, eds. Kay et al., pp. 277–291 (1996).

Carter, P., "Improved Oligonucleotide–Directed Mutagenesis Using M13 Vectors," *Methods in Enzymology*, 154:382–383 (1985).

Collet et al., "A Binary plasmid System for shuffling combinatorial antibody Libraries," *PNAS*, 89(21):10026–10030 (1992).

Higuchi et al., "A general method of in vitro preparation and specific mutagenesis of DNA fragments: study of protein and DNA interactions," *Nuc. Acids Res.*, 16(15):7351–7367 (1988).

Kang et al., "Antibody redesign by chain shuffling from random combinatorial immunoglobulin libraries," *PNAS*, 88(24):11120–11123 (1991).

Kim et al., "Cloning and Nucleotide Sequence of the Collb Shufflon," *Plasmid*, 22:180–184 (1989).

Komano et al., "Physical and Genetic Analyses of IncI2 Plasmid R721: Evidence for the Presence of Shufflon," *Plasmid*, 23:248–251 (1990).

Komano et al., "Distribution of Shufflon among IncI Plasmids," *J. Bacteriology*, 169(11):5317–5319 (1987).

Maryon et al., "Characterization of recombination intermediates from DNA injected into *Xenopus laevis* oocytes: evidence for a nonconservative mechnism of homologous recombination," *Mol. Cell Biol.*, 11(6):3278–3287 (1991).

Michael, S.F., "Thermostable Ligase–Mediated Incorporation of Mutagenic Oligonucleotides During PCR Amplification," chapter 19 from *Methods in Molecular Biology, PCR Cloning Protocols from Molecular Cloning to Genetic Engineering*, eds. B. White, Humana Press, totowa, New Jersey, pp. 189–195 (1997).

Ner et al., "Laboratory Methods: A Simple and Efficient Procedure for Generating Random Point Mutations and for Codon Replacements Using Mixed Oligodeoxynucleotides," *DNA*, 7(2):127–134 (1988).

Olsen et al., "Hybrid Bacillus (1–3,1–4)–beta–glucanases: engineering thermostable enzymes by construction of hybrid genes," *Mol. Gen. Genet.*, 225(2):177–185 (1991).

Prodromou et al., "Protocol, Recursive PCR: a novel technique for total gene synthesis," *Protein Engineering*, 5(8):827–829 (1992).

Rouwendal et al., "Simulatenous Mutagenesis of Multiple Sites: Application of the Ligase Chain Reaction Using PCR Products Instead of Oligonucleotides," *BioTechniques*, 15(1):68–70, 72–74, 76 (1993).

Sambrook et al., *Molecular Cloning: A Laboratory Manual*, 2nd edition, Cold Spring Harbor Laboratory Press, pp. 14.2, 14.34, and 14.35 (1989).

Sandhu et al., "Dual Asymmetric PCR: One–Step Construction of Synthetic Genes," *BioTechniques*, 12(1):14–16 (1992).

Shi et al., "Rapid PCR Construction of a Gene Containing Lym–1 Antibody Variable Regions," *PCR Methods and Applications*, 3:46–53 (1993).

Shuldiner et al., "Hybrid DNA artifact from PCR of closely related target sequences," *Nuc. Acids Res.*, 17(11):4409 (1989).

Smith et al., "Localized sex in bacteria," *Nature*, 349:29–31 (1991).

Stemmer et al., "Increased Antibody Expression from *Escherichia–coli* Through Wobble–Base Library Muatagenesis by Enzymatic Inverse PCR," *Gene*, 123(1):1–7 (1993).

Stemmer et al., "Enzymatic Inverse PCR—A Restriction Site Independent, single–Fragment Method for High–Efficiency, Site–Directed Mutagenesis," *Biotechniques*, 13(2):214 (1992).

Stemmer et al., "Expression of Antibody FV Fragments Specific for a Heavy Metal Chelate Indium Edta In *Escherichia–coli*," *J. Cell Biochem.*, Suppl. 0(15 part G), p. 217 (1991).

Stemmer et al., "A 20–Minute Ethidium Bromide High–slat Extraction Protocol for Plasmid DNA," *Biotechniques*, 10(6):726 (1991).

Wu et al., "Allele–specific enzymatic amplification of beta–globin fgenomic for diagnosis of sickle cell anemia," *PNAS*, 86(6):2757–2760 (1989).

Statutory Declaration of Dr. Gerald Joyce in Australian Opposition against application 703264.

Statutory Declaration of Mae Li Gan in Australian Opposition against application 703264.

Request for leave to amend the Statement of Grounds and Particulars re: opposition 703264 in Australian (Jan. 25, 2001).

Amended Statement of Particulars re: opposition 703264 in Australia (Jan. 25, 2001).

Biotransformations, Pathogenesis, and Evolving Biotechnology, Program and Abstracts, Pseudomonas '89, American Society for Microbiology and The University of Illinois, 7/9–13/89, abstracts 11–21 to 11–25.

Graf et al., "Random circular permutation of genes and expressed polypeptide chains: Application of the method to the catalytic chains of aspartate transcarbamoylase," *PNAS*, 93:11591–11596 (1996).

Janczewski et al., "Molecular phylogenetic inference from saber–toothed cat fossils of Rancho La Brea," *PNAS*, 89:9769–9773 (1992).

Kramer et al., "Oligonucleotide–directed construction of mutations via gapped duplex DNA," *Methods in Enzymology*, 154:350–367 (1987).

Kunkel et al., "Rapid and efficient site–specific mutagenesis without phenotypic selection," *Methods in Enzymology*, 154:367–382 (1987).

Shao et al., "Random–priming in vitro recombination: an effective tool for directed evolution," *Nuc. Acids Res.*, 26(2):681–683 (1998).

Zoller et al., "Oligonucleotide–directed mutagenesis: a simple method using two oligonucleotide primers and a single–stranded DNA template," *Methods in Enzymology*, 154:329–350 (1987).

Statutory Declaration of Ngarie Pepit–Young in Australian Opposition against application 703264.

Statutory Declaration of Ruth Bird in Australian Opposition against application 703264.

Lorberboum–Calski et al., "Cytotoxic activity of an inter-leukin 2–Pseudomonas exotoxin chimeric protein produced in *Escherichia coli*," *PNAS*, 85:1922–1926 (1988).

Arkin et al., "An Algorithm for Protein Engineering: Simulations of Recursive Ensemble Mutagenesis" *Proc. Natl. Acad. Sci. USA*, 89(16):7811–7815 (1992).

Balint et al., "Antibody Engineering By Parsimonious Mutagenesis", *Gene*, 137(1):109–118 (1993).

Bartel et al., "Isolation of New Ribozymes From a Large Pool of Random Sequences", *Science*, 261:1411–1418 (1993).

Beaudry et al., "Directed Evolution of an RNA Enzyme," *Science*, 257:635–641 (1992).

Berger et al., "Phoenix Mutagenesis: One–Step Reassembly of Multiply Cleaved Plasmids With Mixtures of Mutant and Wild–Type Fragments," *Anal. Biochem.*, 214:571–579 (1993).

Berkhout et al., "In Vivo Selection of Randomly Mutated Retroviral Genomes," *Nucleic Acids Research*, 21(22):5020–5024 (1993).

Cadwell et al., "Randomization of Genes by PCR Mutagenesis," *PCR Methods and Applications*, 2:28–33 (1992).

Calogero et al., "In Vivo Recombination and the Production of Hybrid Genes," *Microbiology Letters*, 76:41–44 (1992).

Caren et al., "Efficient Sampling of Protein Sequence Space for Multiple Mutants," *Biotechnology*, 12(5):517–520 (1994).

Crameri et al., "Combinatorial Multiple Cassette Mutagenesis Creates All The Permutations Of Mutant And Wild–Type Sequences", *Biotechniques*, 18(2):194–196 (1995).

Crameri et al., "Improved Green Fluorescent Protein By Molecular Evolution Using DNA Shuffling" *Nat. Biotechnol.*, 14(3):315–319 (1996).

Crameri et al., "Construction And Evolution Of Antibody–Phage Libraries By DNA Shuffling", *Nat. Med.*, 2(1):100–102 (1996).

Crameri et al., "Molecular Evolution Of An Arsenate Detoxification Pathway By DNA Shuffling", *Nat. Biotechnol.*, 15(5):436–438 (1997).

Crameri et al., "DNA Shuffling Of A Family Of Genes From Diverse Species Accelerates Directed Evolution", *Nature*, 391(3664):288–291 (1998).

Delagrave et al., "Recursive Ensemble Mutagenesis," *Protein Engineering*, 6(3):327–331 (1993).

Fang et al., "Human Strand–specific Mismatch Repair Occurs by a Bidirectional Mechanism Similar to That of the Bacterial Reaction", *J. Biol. Chem.*, 268(16): 11838–11844 (Jun. 5, 1993).

Feinberg et al., "A Technique for Radiolabeling DNA Restriction Endonuclease Fragments to High Specific Activity," *Anal. Biochem.*, 132:6–13 (1983).

Fisch et al., "A Strategy Of Exon Shuffling For Making Large Peptide Repertoires Displayed On Filamentous Bacteriophage", *Proc Natl Acad Sci USA*, 93(15):7761–7766 (1996).

Gates et al., "Affinity Selective Isolation Of Ligands From Peptide Libraries Through Display On A Iac Repressor 'Headpiece Dimer'", *J. Mol. Biol.*, 255(3):373–386 (1996).

Gram et al., "In Vitro Selection and Affinity Maturation of Antibodies From a Naïve Combinatorial Immunoglobulin Library", *Proc. Natl. Acad. Sci. USA*, 89:3576–3580 (1992).

Greener et al., "An Efficient Random Mutagenesis Technique Using An *E. coli* Mutator Strain", *Methods in Molecular Biology*, 57:375–385 (1995).

Heim et al., "Wavelength Mutations And Posttranslational Autoxidation Of Green Fluorescent Protein", *Proc. Natl. Acad. Sci. USA*, 91(26):12501–12504 (1994).

Hermes et al., "Searching Sequence Space by Definably Random Mutagenesis: Improving the Catalytic Potency of an Enzyme," *Proc. Natl. Acad. Sci. USA*, 87(2):696–700 (1990).

Ho et al., "Site–Directed Mutagenesis by Overlap Extension Using the Polymerase Chain Reaction," *Gene*, 77:51–59 (1989).

Horton et al., "Engineering Hybrid Genes Without the Use of Restriction Enzymes: Gene Splicing by Overlap Extension," *Gene*, 77:61–68 (1989).

Jones et al., "Recombinant Circle PCR and Recombination PCR for Site–Specific Mutagenesis Without PCR Product Purification," *Biotechniques* 12(4):528–534 (1992).

Kim et al., "Human Immunodeficiency Virus Reverse Transcriptase," *The Journal of Biological Chemistry*, 271(9):4872–4878 (1996).

Leung et al., "A Method For Random Mutagenesis of a Defined DNA Segment Using a Modified Polymerase Chain Reaction," *Techniques*, 1:11–15 (1989).

Marks et al., "By–Passing Immunization: Building High Affinity Human Antibodies by Chain Shuffling," *Bio/Technology*, 10:779–783 (1992).

Marton et al., "DNA Nicking Favors PCR Recombination", *Nucleic Acids Res.*, 19(9):2423–2426 (1991).

Meyerhans et al., "DNA Recombination During PCR," *Nucleic Acids Research*, 18(7):1687–1691 (1990).

Near, "Gene Conversion Of Immunoglobulin Variable Regions In Mutagenesis Cassettes By Replacement PCR Mutagenesis", *Biotechniques*, 12(1):88–97 (1992).

Oliphant et al., "Cloning of Random–Sequence Oligodeoxynucleotides," *Gene*, 44(2–3):177–183 (1986).

Perlak, "Single Step Large Scale Site–Directed In Vitro Mutagenesis Using Multiple Oligonucleotides", *Nucleic Acids Res.*, 18(24):7457–7458 (1990).

*Pharmacia Catalog*, pp. 70–71 (1993 Edition).

Pompon et al., "Protein Engineering by cDNA Recombination in Yeasts: Shuffling of Mammalian Cytochrome P–450 Functions," *Gene*, 83(1):15–24 (1989).

Rao et al., "Recombination and Polymerase Error Facilitate Restoration of Infectivity in Brome Mosaic Virus," *Journal of Virology*, 67(2):969–979 (1993).

Rapley, "Enhancing PCR Amplification And Sequencing Using DNA–Binding Proteins", *Mol. Biotechnol.*, 2(3):295–298 (1994).

Reidhaar–Olson et al., "Combinatorial Cassette Mutagenesis as a Probe of the Informational Content of Protein Sequences," *Science*, 241:53–57 (1988).

Stemmer, "Rapid Evolution of a Protein in Vitro by DNA Shuffling," *Nature*, 370:389–391 (1994).

Stemmer, "DNA Shuffling by Random Fragmentation and Reassembly: In Vitro Recombination for Molecular Evolution" *Proc. Natl. Acad. Sci. USA*, 91(22):10747–10751 (1994).

Stemmer et al., "Selection of an Active Single Chain FV Antibody from a Protein Linker Library Prepared by Enzymatic Inverse PCR," *Biotechniques*, 14(2):256–265 (1992).

Stemmer, "Searching Sequence Space", *Biotechnology*, 13:549–553 (1995).

Stemmer et al., "Single–Step Assembly of A Gene And Entire Plasmid From Large Numbers Of Oligodeoxyribonucleotides", *Gene*, 164(1):49–53 (1995).

Stemmer, "The Evolution of Molecular Computation", *Science*, 270(5241):1510 (1995).

Stemmer, "Sexual PCR and Assembly PCR" *Encyclopedia Mol. Biol.*, VCH Publishers, New York, pp. 447–457 (1996).

Wang et al., "Identification Of Glial Filament Protein And Vimentin In The Same Intermediate Filament System In Human Glioma Cells", *Proc. Natl. Acad. Sci. USA*, 81(7):2102–2106 (1984).

Weber et al., "Formation of Genes Coding for Hybrid Proteins by Recombinant Between Related, Cloned Genes in *E. coli*," *Nucleic Acids Research*, 11(16):5661–5669 (1983).

Weisberg et al., "Simultaneous Mutagenesis Of Multiple Sites: Application Of The Ligase Chain Reaction Using PCR Products Instead Of Oligonucleotides", *BioTechniques*, 15(1):68–76 (1993).

Winter et al., "Making Antibodies By Phage Display Technology", *Ann. Rev. Immunol.*, 12:433–455 (1994).

Zhang et al., "Directed Evolution Of A Fucosidase From A Galactosidase By DNA Shuffling And Screening", *Proc. Natl. Acad. Sci. USA*, 94(9):4504–4509 (1997).

Zhao et al., "Molecular Evolution by Staggered Extension Process (StEP) In Vitro Recombination", *Nature Biotech.*, 16:258–261 (1998).

\* cited by examiner

```
  1  MASVLTNINAMSALQTLRSISSMEDTQSRISSGMRVGSASDNAAYWSIATTMRSDNASLSAVQDAIGLG      R. lupini FlaA
     |.|:|:||||.||||.|||||||||||||||||||||||||||||||||||:||:|||||||||
  1  MTSILTNNSAMAALSTLRSISSSMEDTQSRISSGLRVGSASDNAAYWSIATTMRSDNQALSAVQDALGLG     R. melioti FlaA 71  AAKVDTASAGMDAVIDVVKQIKNKLVTAQESSADKTKIQGEVKQLQEOLKGIVDSASFSGENWLKGDLST     R. lupini FlaA
     |||||||.||.|:::||.|:||||.||||||:.|:.||:|:|||||:||||||||||||||:|||:|
 71  AAKVDTAYSGMESAIEVVKEIKAKLVAATEDGVDKAKIQEEITQLKDQLTSIAEAASFSGENWLQADLSG    R. melioti FlaA 141  TT.TKSVVGSFVRE.GGTVSVKTIDYALNASKVLVDTRATGTKTGILDTAYTGLNANTVTVDINKGGVIT    R. lupini FlaA
     :.|:.|||||.||:.:|||||||||:|:|||:|.|::|..|.|||||:::.:|||.|||.
141  GPVTKSVVGGFVRDSSGAVSVKKVDYSLNTDTVLFD...TTGNTGILDKVY.NVSQASVTLPVNVNGTTS    R. melioti FlaA 209  QASVRAYSTDEMLSLGAKVDGANSNVAVGGGSASSRSTAAGLRVASTLRPPSPHQSLASLPPLTPPLK      R. lupini FlaA
     :..|||||||||.||::|:|||::|.|:|||||||::||:||||..|.::
207  EYTVGAYNVDDLIDASATFDGDYANVGAGALAGDYVKVQGSWVKAVDVAATGQE.................   R. melioti FlaA 279  LVLQLLPVTPSSSTKPTAAP.VQVNLTQSVLTMDVS.SMSSTDVGSYLTGVEKALTSLTSAGAELGSIKQ    R. lupini FlaA
     :|:.....|:.|.||:.|.|:.|||:|||:|||:|||::.|||:::.|:|
277  VVYDDGTTKWGVDTTVTGAPATNVAAPASIATIDITIAAQAGNLDALIAGVDEALTDMTSAAASLGSISS    R. melioti FlaA 347  RIDLQVDFASKLGDALAKGIGRLVDADMNEESTKLKALQTQQQLAIQSLSIANSDSQNILSLPR  410     R. lupini FlaA
     ||||||:...|:|||||.|.|||||||||||:|||||||||:||||||||||||||:|||.|
331  RIDLQSDFVNKLSDSIDSGVGRLVDADMNEESTRLKALQTQQQLAIQALSIANSDSQNVLSLFR  394     R. melioti FlaA
```

```
SCS02   ATGACGAGCATTCTCACCAACAACTCCGCAATGGCCGCCCTACTCCGGATCTCTTCCAGCATGGAAGACACGCAGAGCCGCATCTCCTCCG
SCS02   GCCTTCGGCGTTCGGCCTCCGACAAGCCTCCGAGTTGATACCGCCGACCACCATGGTCGACCACCAGCCCTTTCGGCCGTCCAGGACGCCCT
SCS02   CGGCCCTCGGCGCGCCAAGTTGATACCGCCTATTCCGGATCGGCAGTCGTTAAGGAAATCAAGAACAAACTGGTCACTGCTCAGGAA
SCS02   TCTTCTGCCACAaAAACGaAGATTCAGGGCGAAGTCAAGCAGCTTCAGGGCaTCGTTGATTCCGCTTCCTTCTCCGGTGAGAACTGGC
SCS02   TGCAGGCGGACC..TCAGCGGCGGACCGTCGTTCGTCGGCGCCAAGAGCGTCGTTCGTCCGTAGCCGTCAAGAAGTCAAGAAGTCGATTAC
SCS02   GCTCTGAATGCTTCAAGGTTCTGGTGGATGGCCGTGATCACCCAAGACCGGCCATTCTCGATACTGCTTATACCGGCTTAACGCGA...ACACGG
SCS02   TGACGGTTGATATCAACAAGGCGGCTCGTCAAGAAATGCTCTCCCTGGGTTAAGGGTAGCTGGGTAAGGGTAGCTGACGTGGGTGATGGCGC
SCS02   AAACAGCAACGTTGCTGTTCAAGAAATCGCGG.CTCCGCTTCGTCAAGGTCGGGTAAGCTGGGTAAGGGTAGCTGACGTGGGTGAACGCTCCTGCCG
SCS02   ACCGGCGCCACCGGTCAAGAAATCGCGC...CACCACGGCGGTCGGCTGCGCTCGGCGAACATCGTCGGCGATGTCGGCAGCTACCTCACGGGCGTGAAAAGG
SCS02   CCAACGTTTCGG......CCGGCCAGTCGCGCCCTCGGCCTTGCTCGGCGAACGCTGCAGACCTGTCAACAAGCTCTCGGACTCGATGA
SCS02   CTCTCACCAGCATGACCAGCGCTCGTCGACGCGGAACATGAACGAGGAGTCAGACCAGCCCTCAAGGCCTCGCCATCCAGGCCCTGTGTCG
SCS02   GTCGGGCGTCGGCCGTCTCGGCCGCGTCGTCGACGCGGACATGAACGAGGAGTCAGACCAGCCCTCAAGGCCTCGCCATCCAGGCCCTGTGTCG
SCS02   ATCGCCAACTCGGACTCGCAGAACGTCCTGTCGCTCTTCCGCTAA
```

FIG. 7B

```
ES01  ATGACGAGCATTCTCACCAACAACTCCGCAATGGCCGCCTTTCCGGAGTGCGCTCGATCTCTTCCAGCATGGAAGACACGCAGAGCCGCATCTCCTCCG
ES01  GCCTTCGCTCGGTTCGGCGCCAAGGCCGCCTACTGGTTGCGACCACCATGCCGCTCCGACAACCAGCCCTTTCGGCCGTCCAGACGCCCT
ES01  CGGCCTCGGCGCCGCCAAGGTTGATACCGCCTATTCCGGTATGAATCGGCGATGAAGTCGTTAAGGAAATCAAGGCCAAGCTCGTAGCTGCCACCGAA
ES01  GACGGCGTCGACAAGGCCAAGATCCAAGAGAATCACTCAGCTCAGAGACCAGCGTCGTCCGACGAGCATCGCCGACGTCCTTCCTTCTCCGGTGAGAACTGGC
ES01  TGCAGGCGGACC..TCAACGCGGGACCTTCCAAGGTTCGTGTGGATACCCGGACACAAGGTCTACAACGTCTCGCAGGCAAGCGTCACGC
ES01  GCTCTGAATGCTTCCAAGGTTCGGATACCCGGACACAAGGTCTACAACGTCTCGCAGGCAAGCGTCACGC
ES01  TGACGG......TCAACACCAACGGCGTCGAATCGCAGTCGTCAAGGTCGACGGTTGCTGCCTATTCGCTGGA.......GTCCCTCACCGAAGCCGGTGCGGAGTT
ES01  CCAGGGCAACTATGCTCTTCAGGCGTCAACAGCTACGTCAAGGTCGACggGGTTAAGGGTAGCGTCGACgCTGCGCCTCCATCACCGCATCA
ES01  ACACCAGTCGCTGGCAAGTTTGCCGCCGCTTACACCGCTTACACCCGCTGAAGCTGGTACTGCCAGCTGGTCGTGCCGGTGACgCCATCATGTCGACGGATGTGGCAGCTACCTCACGGGCGTGAAAAGG
ES01  GCGCCGGTCAGTAAACCTCACCCAGTCGGCTGAACTCGGCTGACCTGCGCATGACCTGGCTCCATCTCCTGCGCATGACCTGCGCATCGCATCGATCGATCGATGCGAATTCGTCAACAAGCTCTCGATCGA
ES01  CTCTCACCAGCTGACGAGCGCTGTCGACGCGCTCTCGACGCGCGGACATGAACGAGGAGTCCGCCTCAAGGCCCCTCAAGGCCCTCAAGGCCCTCAAGGCCCATCCAGGCCCTGTCG
ES01  GTCGGGCGTCGGCGTCGTCGACGCGGACATGAACGAGGAGTCCGCCTCTTCCGCTAA
ES01  ATCGCCAACTCGGACTCGCAGAACGTCCTGCTCGCTCTTCCGCTAA
```

FIG. 7C

```
ES02  ATGACGAGCATTCTCACCAACAACTCCGCAATGGCCGCGCTTTCCGGAGTGCGCTCGATCTCTTCCAGCATGGAAGACACGCAGAGCCGCATCTCCTCCG
ES02  GCCTTCGCGTCGGTTCGGCCTCCGACAACGCCTCCGACGCTCTGGTCGATTGCGACCACCATGCGCTCCGACAACCAGGCCCTTCGGCCGTCAGGACGCCCT
ES02  CGGCCTCGGCGCCAAGGTTGATACCGCCTATTCCGGTATGGAAGTCGTTAAGGAAATCAAGGCCAAGCTCGTAGCTGCCACCGAA
ES02  GACGCGTCGACAAGGCCAAGATCCAAGAGAATCACTCAGCTCGTCGACGAGCATCGACGAGCAGTCGTTCGTCCGTGACGGCCTTCCTTCTCCGGTGAGAACTGGC
ES02  TGCAGGCGGACC...TCAGCGGACGTTCTGGTGGATACCCGGCAACGGCCTCCGTCCGCGGAAGCGGTTCCGTAGCCGTCAAGACCATCGATTAC
ES02  GCTCTGAATGCTTCCAAGGTTCTGGTGGATATCCGGCATTCTCGATACTGCTTATACCGGCCTTAACGCGA...ACACGG
ES02  TGACGGTTGATATGCAACAAGGGCGTGATCAACAGTCACCCAGCCTACGTCGAAAATGCTCTCCCTCACCGAAGCCGGTGCGGAGTT
ES02  CCAGGGCAACTATGCTCTTCAGGGCGTCAAGAAATCGCC...CACCACGACGGCAGCTGGTACCATCACTGCAGACAGCTGGCAACGCTCCTGCCG
ES02  ACCGGCGCCACCGGTCAAGAAATCGCGC...CCGGCCAGTCGGTCGCGGCCTCGCGCCTCGCGCCCTGAATGGGTGCACCTGCAGCTGCCGCTCGATGCCCTGATCAGCGGTCGACGCCG
ES02  CCAACGTTTCGG......CCGGCCAGTCGGTCGCGGAACATCAACATCGTCCGGCATGACCTGCAGAGGAATTCGTCAACAAGCTCTCGACTCGATCGA
ES02  CTTTGACAGACATGACCAGCCGTCGCCTCGTCGACGCGGACATGAACGAGGAGTGACCCGCCCTCAAGGCCCTCCAGACCCAGCAGCAGCCTCGCCATCCAGCCCTGTCG
ES02  GTCGGGCGTCGGCCGTCTCGTCGGCAGAACGTCCTGCTCGCTCTTCGCT
ES02  ATCGCCAACTCGGACTCGCAGAACGTCCTGCTCGCTCTTCGCT
ES02  AA
```

FIG. 7D

1     CTGCAGCGTGCCCAGCTGTTCGTGGTGGTGATCGCGGCCGCGCTGGCCGCCGTCGCGGTC
61    GCCGCCGCCGGGCCGATCGAGTTCGTCGCCTTCGTCGTGCCGCAGATCGCCCTGCGGCTC
121   TGCGGCGGCAGCCGGCCGCCCCTGCTCGCCTCGGCGATGCTCGGCGCGCTGCTGGTGGTC
181   GGCGCCGACCTGGTCGCTCAGATCGTGGTGGCGCCGAAGGAGCTGCCGGTCGGCCTGCTC
241   ACCGCGATGATCGGCACCCCGTACCTGCTCTGGCTCCTGCTTCGGCGATCAAGAAAGGTG
301   AGCGGATGAACGCCCGCCTGCGTGGCGAGGGCCTGCACCTCGCGTACGGGGACCTGACCG
361   TGATCGACGGCCTCGACGTCGACGTGCACGACGGGCTGGTCACCACCATCATCGGGCCCA
421   ACGGGTGCGGCAAGTCGACGCTGCTCAAGGCGCTCGGCCGGCTGCTGCGCCCGACCGGCG
481   GGCAGGTGCTGCTGGACGGCCGCCGCATCGACCGGACCCCCACCCGTGACGTGGCCCGGG
541   TGCTCGGCGTGCTGCCGCAGTCGCCCACCGCGCCCGAAGGGCTCACCGTCGCCGACCTGG
601   TGATGCGCGGCCGGCACCCGCACCAGACCTGGTTCCGGCAGTGGTCGCGCGACGACGAGG
661   ACCAGGTCGCCGACGCGCTGCGCTGGACCGACATGCTGGCGTACGCGGACCGCCCGGTGG
721   ACGCCCTCTCCGGCGGTCAGCGCCAGCGCGCCTGGATCAGCATGGCGCTGGCCCAGGGCA
781   CCGACCTGCTGCTGCTGGACGAGCCGACCACCTTCCTCGACCTGGCCCACCAGATCGACG
841   TGCTGGACCTGGTCCGCCGGCTGCACGCCGAGATGGGCCGGACCGTGGTGATGGTGCTGC
901   ACGACCTGAGCCTGGCCGCCCGGTACGCCGACCGGCTGATCGCGATGAAGGACGGCCGGA
961   TCGTGGCGAGCGGGGCGCCGGACGAGGTGCTCACCCCGGCGCTGCTGGAGTCGGTCTTCG
1021  GGCTGCGCGCGATGGTGGTGCCCGACCCGGCGACCGGCACCCGCTGGTGATCCCCCTGC
1081  CGCGCCCCGCCACCTCGGTGCGGGCCTGAAATCGATGAGCGTGGTTGCTTCATCGGCCTG
1141  CCGAGCGATGAGAGTATGTGGGCGGTAGAGCGAGTCTCGAGGGGAGATGCCGCCGTGAC
                                                              V   T

1201  GTCCTCGTACATGCGCCTGAAAGCAGCAGCGATCGCCTTCGGTGTGATCGTGGCGACCGC
  3    S   S   Y   M   R   L   K   A   A   A   I   A   F   G   V   I   V   A   T   A

1261  AGCCGTGCCGTCACCCGCTTCCGGCAGGGAACATGACGGCGGCTATGCGGCCCTGATCCG
 23    A   V   P   S   P   A   S   G   R   E   H   D   G   G   Y   A   A   L   I   R

1321  CCGGGCCTCGTACGGCGTCCCGCACATCACCGCCGACGACTTCGGGAGCCTCGGTTTCGG
 43    R   A   S   Y   G   V   P   H   I   T   A   D   D   F   G   S   L   G   F   G

1381  CGTCGGGTACGTGCAGGCCGAGGACAACATCTGCGTCATCGCCGAGAGCGTAGTGACGGC
 63    V   G   Y   V   Q   A   E   D   N   I   C   V   I   A   E   S   V   V   T   A

1441  CAACGGTGAGCGGTCGCGGTGGTTCGGTGCGACCGGGCCGGACGACGCCGATGTGCGCAG
 83    N   G   E   R   S   R   W   F   G   A   T   G   P   D   D   A   D   V   R   S

*FIG. 13A*

```
1501 CGACCTCTTCCACCGCAAGGCGATCGACGACCGCGTCGCCGAGCGGCTCCTCGAAGGGCC
103   D  L  F  H  R  K  A  I  D  D  R  V  A  E  R  L  L  E  G  P

1561 CCGCGACGGCGTGCGGGCGCCGTCGGACGACGTCCGGGACCAGATGCGCGGCTTCGTCGC
123   R  D  G  V  R  A  P  S  D  D  V  R  D  Q  M  R  G  F  V  A

1621 CGGCTACAACCACTTCCTACGCCGCACCGGCGTGCACCGCCTGACCGACCCGGCGTGCCG
143   G  Y  N  H  F  L  R  R  T  G  V  H  R  L  T  D  P  A  C  R

1681 CGGCAAGGCCTGGGTGCGCCCGCTCTCCGAGATCGATCTCTGGCGTACGTCGTGGGACAG
163   G  K  A  W  V  R  P  L  S  E  I  D  L  W  R  T  S  W  D  S

1741 CATGGTCCGGGCCGGTTCCGGGGCGCTGCTCGACGGCATCGTCGCCGCGACGCCACCTAC
183   M  V  R  A  G  S  G  A  L  L  D  G  I  V  A  A  T  P  P  T

1801 AGCCGCCGGGCCCGCGTCAGCCCCGGAGGCACCCGACGCCGCCGCGATCGCCGCCGCCCT
203   A  A  G  P  A  S  A  P  E  A  P  D  A  A  A  I  A  A  A  L

1861 CGACGGGACGAGCGCGGGCATCGGCAGCAACGCGTACGGCCTCGGCGCGCAGGCCACCGT
223   D  G  T  S  A  G  I  G  S  N  A  Y  G  L  G  A  Q  A  T  V

1921 GAACGGCAGCGGGATGGTGCTGGCCAACCCGCACTTCCCGTGGCAGGGCGCCGCACGCTT
243   N  G  S  G  M  V  L  A  N  P  H  F  P  W  Q  G  A  A  R  F

1981 CTACCGGATGCACCTCAAGGTGCCCGGCCGCTACGACGTCGAGGGCGCGGCGCTGATCGG
263   Y  R  M  H  L  K  V  P  G  R  Y  D  V  E  G  A  A  L  I  G

2041 CGACCCGATCATCGGGATCGGGCACAACCGCACGGTCGCCTGGAGCCACACCGTCTCCAC
283   D  P  I  I  G  I  G  H  N  R  T  V  A  W  S  H  T  V  S  T

2101 CGCCCGCCGGTTCGTGTGGCACCGCCTGAGCCTCGTGCCCGGCGACCCCACCTCCTATTA
303   A  R  R  F  V  W  H  R  L  S  L  V  P  G  D  P  T  S  Y  Y

2161 CGTCGACGGCCGGCCCGAGCGGATGCGCGCCCGCACGGTCACGGTCCAGACCGGCAGCGG
323   V  D  G  R  P  E  R  M  R  A  R  T  V  T  V  Q  T  G  S  G
```

*FIG. 13A*
(CONTINUED)

```
2221 CCCGGTCAGCCGCACCTTCCACGACACCCGCTACGGCCCGGTGGCCGTGATGCCGGGCAC
343   P   V   S   R   T   F   H   D   T   R   Y   G   P   V   A   V   M   P   G   T

2281 CTTCGACTGGACGCCGGCCACCGCGTACGCCATCACCGACGTCAACGCGGGCAACAACCG
363   F   D   W   T   P   A   T   A   Y   A   I   T   D   V   N   A   G   N   N   R

2341 CGCCTTCGACGGGTGGCTGCGGATGGGCCAGGCCAAGGACGTCCGGGCGCTCAAGGCGGT
383   A   F   D   G   W   L   R   M   G   Q   A   K   D   V   R   A   L   K   A   V

2401 CCTCGACCGGCACCAGTTCCTGCCCTGGGTCAACGTGATCGCCGCCGACGCGCGGGGCGA
403   L   D   R   H   Q   F   L   P   W   V   N   V   I   A   A   D   A   R   G   E

2461 GGCCCTCTACGGCGATCATTCGGTCGTCCCCCGGGTGACCGGCGCGCTCGCTGCCGCCTG
423   A   L   Y   G   D   H   S   V   V   P   R   V   T   G   A   L   A   A   A   C

2521 CATCCCGGCGCCGTTCCAGCCGCTCTACGCCTCCAGCGGCCAGGCGGTCCTGGACGGTTC
443   I   P   A   P   F   Q   P   L   Y   A   S   S   G   Q   A   V   L   D   G   S

2581 CCGGTCGGACTGCGCGCTCGGCGCCGACCCCGACGCCGCGGTCCCGGGCATTCTCGGCCC
463   R   S   D   C   A   L   G   A   D   P   D   A   A   V   P   G   I   L   G   P

2641 GGCGAGCCTGCCGGTGCGGTTCCGCGACGACTACGTCACCAACTCCAACGACAGTCACTG
483   A   S   L   P   V   R   F   R   D   D   Y   V   T   N   S   N   D   S   H   W

2701 GCTGGCCAGCCCGGCCGCCCCGCTGGAAGGCTTCCCGCGGATCCTCGGCAACGAACGCAC
503   L   A   S   P   A   A   P   L   E   G   F   P   R   I   L   G   N   E   R   T

2761 CCCGCGCAGCCTGCGCACCCGGCTCGGGCTGGACCAGATCCAGCAGCGCCTCGCCGGCAC
523   P   R   S   L   R   T   R   L   G   L   D   Q   I   Q   Q   R   L   A   G   T

2821 GGACGGTCTGCCCGGCAAGGGCTTCACCACCGCCCGGCTCTGGCAGGTCATGTTCGGCAA
543   D   G   L   P   G   K   G   F   T   T   A   R   L   W   Q   V   M   F   G   N

2881 CCGGATGCACGGCGCCGAACTCGCCCGCGACGACCTGGTCGCGCTCTGCCGCCGCCAGCC
563   R   M   H   G   A   E   L   A   R   D   D   L   V   A   L   C   R   R   Q   P
```

FIG. 13A
(CONTINUED)

```
2941 GACCGCGACCGCCTCGAACGGCGCGATCGTCGACCTCACCGCGGCCTGCACGGCGCTGTC
 583    T   A   T   A   S   N   G   A   I   V   D   L   T   A   A   C   T   A   L   S

3001 CCGCTTCGATGAGCGTGCCGACCTGGACAGCCGGGGCGCGCACCTGTTCACCGAGTTCGC
 603    R   F   D   E   R   A   D   L   D   S   R   G   A   H   L   F   T   E   F   A

3061 CCTCGCGGGCGGAATCAGGTTCGCCGACACCTTCGAGGTGACCGATCCGGTACGCACCCC
 623    L   A   G   G   I   R   F   A   D   T   F   E   V   T   D   P   V   R   T   P

3121 GCGCCGTCTGAACACCACGGATCCGCGGGTACGGACGGCGCTCGCCGACGCCGTGCAACG
 643    R   R   L   N   T   T   D   P   R   V   R   T   A   L   A   D   A   V   Q   R

3181 GCTCGCCGGCATCCCCCTCGACGCGAAGCTGGGAGACATCCACACCGACAGCCGCGGCGA
 663    L   A   G   I   P   L   D   A   K   L   G   D   I   H   T   D   S   R   G   E

3241 ACGGCGCATCCCCATCCACGGTGGCCGCGGGGAAGCAGGCACCTTCAACGTGATCACCAA
 683    R   R   I   P   I   H   G   G   R   G   E   A   G   T   F   N   V   I   T   N

3301 CCCGCTCGTGCCGGGCGTGGGATACCCGCAGGTCGTCCACGGAACATCGTTCGTGATGGC
 703    P   L   V   P   G   V   G   Y   P   Q   V   V   H   G   T   S   F   V   M   A

3361 CGTCGAACTCGGCCCGCACGGCCCGTCGGGACGGCAGATCCTCACCTATGCGCAGTCGAC
 723    V   E   L   G   P   H   G   P   S   G   R   Q   I   L   T   Y   A   Q   S   T

3421 GAACCCGAACTCACCCTGGTACGCCGACCAGACCGTGCTCTACTCGCGGAAGGGCTGGGA
 743    N   P   N   S   P   W   Y   A   D   Q   T   V   L   Y   S   R   K   G   W   D

3481 CACCATCAAGTACACCGAGGCGCAGATCGCGGCCGACCCGAACCTGCGCGTCTACCGGGT
 763    T   I   K   Y   T   E   A   Q   I   A   A   D   P   N   L   R   V   Y   R   V

3541 GGCACAGCGGGGACGCTGACCCACGTCACGCCGGCTCGGCCCGTGCGGGGGCGCAGGGCG
 783    A   Q   R   G   R   *
```

*FIG. 13A*
(CONTINUED)

```
3601  CCGATCGTCTCTGCATCGCCGGTCAGCCGGGGCCTGCGTCGACCGGCGGCGGCCGGTCGA
3661  CGCCCGCGTCCCGGCGCAGCGACTGGCTGAAGCGCCAGGCGTCGGCGGCCCGGGGCAGGT
3721  TGTTGAACATCACGTACGCCGGGCCGCCGTCGAGGATGCCGGCGAGGTGTGCCAGCTCGG
3781  CATCCGTGTACACATGCCGGGCGCCGGTGATGCCGTGCAGCCGGTAATAGGCCATCGGCG
3841  TCAGACTGCGGCGCAGGAACGGGTCGGCGGCGTGGGTCAGGTCCAGCTCCTGGCACAAGC
3901  CCTCGACCACCTCGTCCGGCCACGGGCCGCGCGGCTCCCACAACAGCCGGACACCGGCCG
3961  GCCGGCGCGCTCGGGCGCAGAACTCACGCAGTCGCGCGATGGCGGGTTCGGTCGGCCGGA
4021  AACTCGCCGGGCACTGCAG
```

METHOD FOR CREATING POLYNUCLEOTIDE AND POLYPEPTIDE SEQUENCES

CROSS-REFERENCES TO RELATED APPLICATIONS

This application derives priority from U.S. Ser. No. 60/067,908, filed Dec. 8, 1997, which is incorporated by reference in its entirety for all purposes.

STATEMENT OF GOVERNMENT INTEREST

The invention described herein was made in the performance of work under a NASA contract, and is subject to the provisions of Public Law 96-517 (35 USC §202) in which the contractor has elected to retain title.

COPYRIGHT NOTICE

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

TECHNICAL FIELD

The invention resides in the technical field of genetics, and more specifically, forced molecular evolution of polynucleotides to acquire desired properties.

BACKGROUND

A variety of approaches, including rational design and directed evolution, have been used to optimize protein functions (1, 2). The choice of approach for a given optimization problem depends, in part, on the degree of understanding of the relationships between sequence, structure and function. Rational redesign typically requires extensive knowledge of a structure-function relationship. Directed evolution requires little or no specific knowledge about structure-function relationship; rather, the essential features is a means to evaluate the function to be optimized. Directed evolution involves the generation of libraries of mutant molecules followed by selection or screening for the desired function. Gene products which show improvement with respect to the desired property or set of properties are identified by selection or screening. The gene(s) encoding those products can be subjected to further cycles of the process in order to accumulate beneficial mutations. This evolution can involve few or many generations, depending on how far one wishes to progress and the effects of mutations typically observed in each generation. Such approaches have been used to create novel functional nucleic acids (3, 4), peptides and other small molecules (3), antibodies (3), as well as enzymes and other proteins (5, 6, 7). These procedures are fairly tolerant to inaccuracies and noise in the function evaluation (7).

Several publications have discussed the role of gene recombination in directed evolution (see WO 97/07205, WO 98/42727, U.S. Pat. No. 5,807,723, U.S. Pat. No. 5,721,367, U.S. Pat, No. 5,776,744 and WO 98/41645 U.S. Pat. No. 5,811,238, WO 98/41622, WO 98/41623, and U.S. Pat. No. 5,093,257).

A PCR-based group of recombination methods consists of DNA shuffling [5, 6], staggered extension process [89, 90] and random-priming recombination [87]. Such methods typically involve synthesis of significant amounts of DNA during assembly/recombination step and subsequent amplification of the final products and the efficiency of amplification decreases with gene size increase.

Yeast cells, which possess an-active system for homologous recombination, have been used for in vivo recombination. Cells transformed with a vector and partially overlapping inserts efficiently join the inserts together in the regions of homology and restore a functional, covalently-closed plasmid [91]. This method does not require PCR amplification at any stage of recombination and therefore is free from the size considerations inherent in this method. However, the number of crossovers introduced in one recombination event is limited by the efficiency of transformation of one cell with multiple inserts. Other in vivo recombination methods entail recombination between two parental genes cloned on the same plasmid in a tandem orientation. One method relies on homologous recombination machinery of bacterial cells to produce chimeric genes [92]. A first gene in the tandem provides the N-terminal part of the target protein, and a second provides the C-terminal part. However, only one crossover can be generated by this approach. Another in vivo recombination method uses the same tandem organization of substrates in a vector [93]. Before transformation into E. coli cells, plasmids are linearized by endonuclease digestion between the parental sequences. Recombination is performed in vivo by the enzymes responsible for double-strand break repair. The ends of linear molecules are degraded by a 5"3' exonuclease activity, followed by annealing of complementary single-strand 3' ends and restoration of the double-strand plasmid [94]. This method has similar advantages and disadvantages of tandem recombination on circular plasmid.

SUMMARY OF THE INVENTION

The invention provides methods for evolving a polynucleotide toward acquisition of a desired property. Such methods entail incubating a population of parental polynucleotide variants under conditions to generate annealed polynucleotides comprises heteroduplexes. The heteroduplexes are then exposed to a cellular DNA repair system to convert the heteroduplexes to parental polynucleotide variants or recombined polynucleotide variants. The resulting polynucleotides are then screened or selected for the desired property.

In some methods, the heteroduplexes are exposed to a DNA repair system in vitro. A suitable repair system can be prepared in the form of cellular extracts.

In other methods, the products of annealing including heteroduplexes are introduced into host cells. The heteroduplexes are thus exposed to the host cells' DNA repair system in vivo.

In several methods, the introduction of annealed products into host cells selects for heteroduplexes relative to transformed cells comprising homoduplexes. Such can be achieved, for example, by providing a first polynucleotide variant as a component of a first vector, and a second polynucleotide variant is provided as a component of a second vector. The first and second vectors are converted to linearized forms in which the first and second polynucleotide variants occur at opposite ends. In the incubating step, single-stranded forms of the first linearized vector reanneal with each other to form linear first vector, single-stranded forms of the second linearized vector reanneal with each other to form linear second vector, and single-stranded linearized forms of the first and second vectors anneal with each to form a circular heteroduplex bearing a nick in each strand. Introduction of the products into cells thus selects for cirular heteroduplexes relative to the linear first and second vector. Optionally, in the above methods, the first and second vectors can be converted to linearized forms by PCR. Alternatively, the first and second vectors can be converted to linearized forms by digestion with first and second restriction enzymes.

In some methods, polynucleotide variants are provided in double stranded form and are converted to single stranded form before the annealing step. Optionally, such conversion is by conducting asymmetric amplification of the first and second double stranded polynucleotide variants to amplify a first strand of the first polynucleotide variant, and a second strand of the second polynucleotide variant. The first and second strands anneal in the incubating step to form a heteroduplex.

In some methods, a population of polynucleotides comprising first and second polynucleotides is provided in double stranded form, and the method further comprises incorporating the first and second polynucleotides as components of first and second vectors, whereby the first and second polynucleotides occupy opposite ends of the first and second vectors. In the incubating step single-stranded forms of the first linearized vector reanneal with each other to form linear first vector, single-stranded forms of the second linearized vector reanneal with each other to form linear second vector, and single-stranded linearized forms of the first and second vectors anneal with each to form a circular heteroduplex bearing a nick in each strand. In the introducing step selects for transformed cells comprises the circular heteroduplexes relative to the linear first and second vector.

In some methods, the first and second polynucleotides are obtained from chromosomal DNA. In some methods, the polynucleotide variants encode variants of a polypeptide. In some methods, the population of polynucleotide variants comprises at least 20 variants. In some methods, the population of polynucleotide variants are at least 10 kb in length.

In some methods, the polynucleotide variants comprises natural variants. In other methods, the polynucleotide variants comprise variants generated by mutagenic PCR or cassette mutagenesis. In some methods, the host cells into which heteroduplexes are introduced are bacterial cells. In some methods, the population of variant polynucleotide variants comprises at least 5 polynucleotides having at least 90% sequence identity with one another.

Some methods further comprise a step of at least partially demethylating variant polynucleotides. Demethylation can be achieved by PCR amplification or by passaging variants through methylation-deficient host cells.

Some methods include a further step of sealing one or more nicks in heteroduplex molecules before exposing the heteroduplexes to a DNA repair system. Nicks can be sealed by treatment with DNA ligase.

Some methods further comprise a step of isolating a screened recombinant polynucleotide ariant. In some methods, the polynucleotide variant is screened to produce a recombinant protein or a secondary metabolite whose production is catalyzed thereby.

In some methods, the recombinant protein or secondary metabolite is formulated with a carrier to form a pharmaceutical composition.

In some methods, the polynucleotide variants encode enzymes selected from the group consisting of proteases, lipases, amylases, cutinases, cellulases, amylases, oxidases, peroxidases and phytases. In other methods, the polynucleotide variants encode a polypeptide selected from the group consisting of insulin, ACTH, glucagon, somatostatin, somatotropin, thymosin, parathyroid hormone, pigmentary hormones, somatomedin, erthropoietin, luteinizing hormone, chorionic gonadotropin, hyperthalmic releasing factors, antidiuretic hormones, thyroid stimulating hormone, relaxin, interferon, thrombopoietic (TPO), and prolactin.

In some methods, each polynucleotide in the population of variant polynucleotides encodes a plurality of enzymes forming a metabolic pathway.

BRIEF DESCRIPTION OF THE DRAWINGS

FIG. 5 shows the amino acid sequences of the FlaA from *R. lupini* (SEQ ID NO: 1) and *R. meliloti* (SEQ ID NO:2).

FIGS. 7A, B, C and D show the DNA sequences of four mosaic flaA genes created by in vitro heteroduplex formation followed by in vivo repair ((a) is SEQ ID NO:3, (b) is SEQ ID NO:4, (c) is SEQ ID NO:5 and (d) is SEQ ID NO:6).

FIGS. 13A, B, C, D and E show the DNA sequence of *A.utahensis* ECB deacylase gene mutant M-15 genes created by in vitro heteroduplex formation followed by in vivo repair (SEQ ID NO:7).

DEFINITIONS

Figure 1:
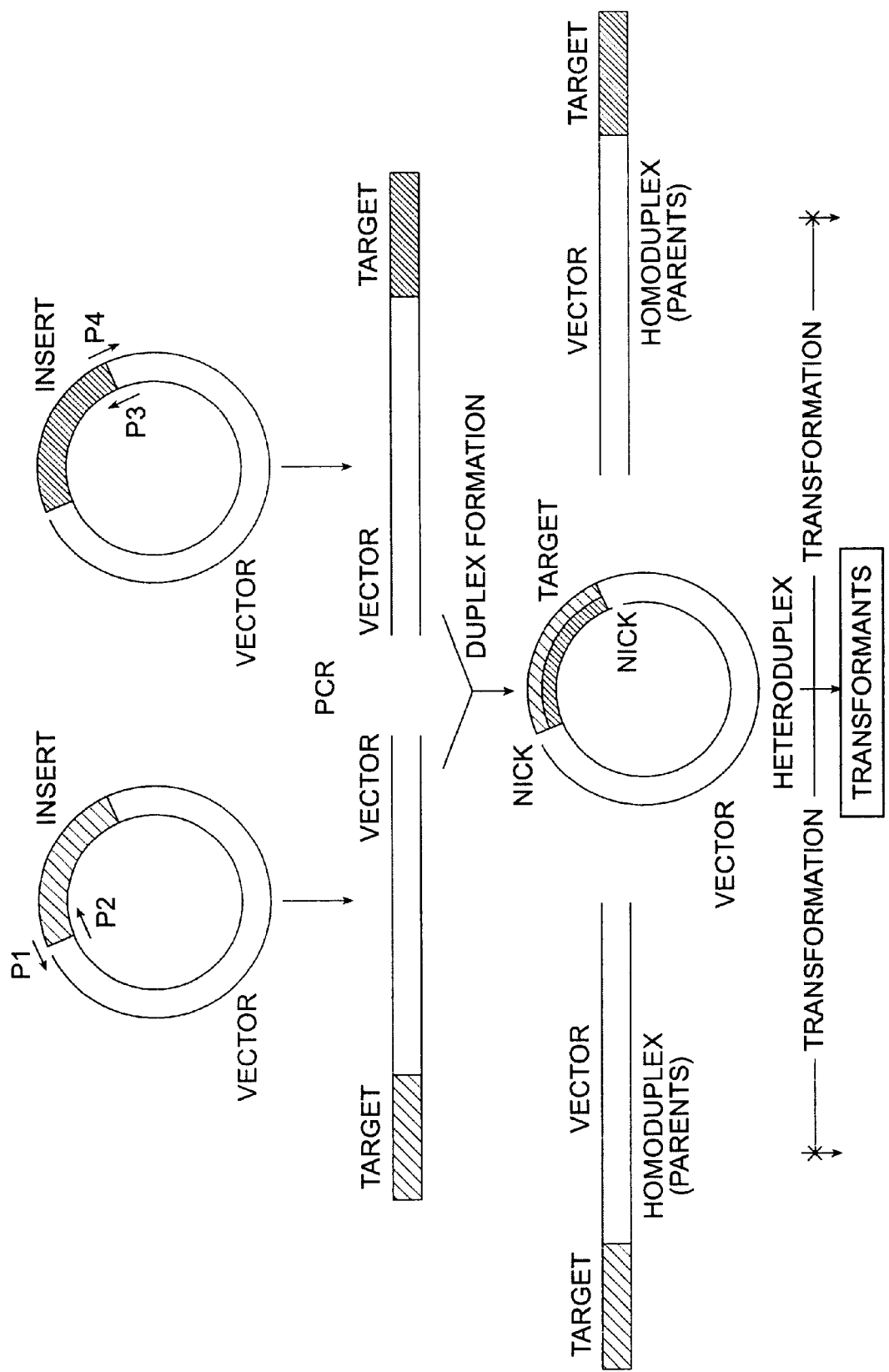
FIG. 1 illustrates the process of heteroduplex formation using polymerase chain reaction (PCR) with one set of primers for each different sequence to amplify the target sequence and vector.

Screening is, in general, a two-step process in which one first physically separates the cells and then determines which cells do and do not possess a desired property. Selection is a form of screening in which identification and physical separation are achieved simultaneously by expression of a selection marker, which, in some genetic circumstances, allows cells expressing the marker to survive while other cells die (or vice versa). Exemplary screening members include luciferase, βgalactosidase and green fluorescent protein. Selection markers include drug and toxin resistance genes. Although spontaneous selection can and does occur in the course of natural evolution, in the present methods selection is performed by man.

An exogenous DNA segment is one foreign (or heterologous) to the cell or homologous to the cell but in a position within the host cell nucleic acid in which the element is not ordinarily found. Exogenous DNA segments are expressed to yield exogenous polypeptides.

The term gene is used broadly to refer to any segment of DNA associated with a biological function. Thus, genes include coding sequences and/or the regulatory sequences required for their expression. Genes also include nonexpressed DNA segments that, for example, form recognition sequences for other proteins.

The term "wild-type" means that the nucleic acid fragment does not comprise any mutations. A "wild-type" protein means that the protein will be active at a level of activity found in nature and typically will comprise the amino acid sequence found in nature. In an aspect, the term "wild type" or "parental sequence" can indicate a starting or reference sequence prior to a manipulation of the invention.

"Substantially pure" means an object species is the predominant species present (i.e., on a molar basis it is more abundant than any other individual macromolecular species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species. Solvent species, small molecules (<500 Daltons), and elemental ion species are not considered macromolecular species.

Percentage sequence identity is calculated by comparing two optimally aligned sequences over the window of comparison, determining the number of positions at which the identical nucleic acid base occurs in both sequences to yield the number of matched positions, dividing the number of matched positions by the total number of positions in the window of comparison. Optimal alignment of sequences for aligning a comparison window can be conducted by computerized implementations of algorithms GAP, BESTFIT, FASTA, and TFASTA in the Wisconsin Genetics Software Package Release 7.0, Genetics Computer Group, 575 Science Dr., Madison, Wis.

The term naturally-occurring is used to describe an object that can be found in nature as distinct from being artificially produced by man. For example, a polypeptide or polynucleotide sequence that is present in an organism (including viruses) that can be isolated from a source in nature and which has not been intentionally modified by man in the laboratory is naturally-occurring. Generally, the term naturally-occurring refers to an object as present in a non-pathological (undiseased) individual, such as would be typical for the species.

A nucleic acid is operably linked when it is placed into a functional relationship with another nucleic acid sequence. For instance, a promoter or enhancer is operably linked to a coding sequence if it increases the transcription of the coding sequence. Operably linked means that the DNA sequences being linked are typically contiguous and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

A specific binding affinity between, for example, a ligand and a receptor, means a binding affinity of at least $1 \times 10^6$ $M^{-1}$.

The term "cognate" as used herein refers to a gene sequence that is evolutionarily and functionally related between species. For example but not limitation, in the human genome, the human CD4 gene is the cognate gene to the mouse CD4 gene, since the sequences and structures of these two genes indicate that they are highly homologous and both genes encode a protein which functions in signaling T cell activation through MHC class II-restricted antigen recognition.

The term "heteroduplex" refers to hybrid DNA generated by base pairing between complementary single strands derived from the different parental duplex molecules, whereas the term "homoduplex" reters to double-stranded DNA generated by base pairing between complementary single strands derived from the same parental duplex molecules.

The term "nick" in duplex DNA refers to the absence of a phosphodiester bond between two adjacent nucleotides on one strand. The term "gap" in duplex DNA refers to an absence of one or more nucleotides in one strand of the duplex. The term "loop" in duplex DNA refers to one or more unpaired nucleotides in one strand.

A mutant or variant sequence is a sequence showing substantial variation from a wild type or reference sequence that differs from the wild type or reference sequence at one or more positions.

DETAILED DESCRIPTION

I. General

The invention provides methods of evolving a polynucleotide toward acquisition of a desired property. The substrates for the method are a population of at least two polynucleotide variant sequences that contain regions of similarity with each other but, which also have point(s) or regions of divergence. The substrates are annealed in vitro at the regions of similarity. Annealing can regenerate initial substrates or can form heteroduplexes, in which component strands originate from different parents. The products of annealing are exposed to enzymes of a DNA repair, and optionally a replication system, that repairs unmatched pairings. Exposure can be in vivo as when annealed products are transformed into host cells and exposed to the hosts DNA repair system. Alternatively, exposure can be in vitro, as when annealed products are exposed to cellular extracts containing functional DNA repair systems. Exposure of heteroduplexes to a DNA repair system results in DNA repair at bulges in the heteroduplexes due to DNA mismatching. The repair process differs from homologous recombination in promoting nonreciprocal exchange of diversity between strands. The DNA repair process is typically effected on both component strands of a heteroduplex molecule and at any particular mismatch is typically random as to which strand is repaired. The resulting population can thus contain recombinant polynucleotides encompassing an essentially random reassortment of points of divergence between parental strands. The population of recombinant polynucleotides is then screened for acquisition of a desired property. The property can be a property of the polynucleotide per se, such as capacity of a DNA molecule to bind to a protein or can be a property of an expression product thereof, such as mRNA or a protein.

II. Substrates For Shuffling

The substrates for shuffling are variants of a reference polynucleotide that show some region(s) of similarity with the reference and other region(s) or point(s) of divergence. Regions of similarity should be sufficient to support annealing of polynucleotides such that stable heteroduplexes can be formed. Variants forms often show substantial sequence identity with each other (e.g., at least 50%, 75%, 90% or 99%). There should be at least sufficient diversity between substrates that recombination can generate more diverse products than there are starting materials. Thus, there must be at least two substrates differing in at least two positions. The degree of diversity depends on the length of the substrate being recombined and the extent of the functional change to be evolved. Diversity at between 0.1–25% of positions is typical. Recombination of mutations from very closely related genes or even whole sections of sequences from more distantly related genes or sets of genes can enhance the rate of evolution and the acquisition of desirable new properties. Recombination to create chimeric or mosaic genes can be useful in order to combine desirable features of two or more parents into a single gene or set of genes, or to create novel functional features not found in the parents. The number of different substrates to be combined can vary widely in size from two to 10, 100, 1000, to more than $10^5$, $10^7$, or $10^9$ members.

The initial small population of the specific nucleic acid sequences having mutations may be created by a number of different methods. Mutations may be created by error-prone PCR. Error-prone PCR uses low-fidelity polymerization conditions to introduce a low level of point mutations randomly over a long sequence. Alternatively, mutations can be introduced into the template polynucleotide by oligonucleotide-directed mutagenesis. In oligonucleotide-directed mutagenesis, a short sequence of the polynucleotide is removed from the polynucleotide using restriction enzyme digestion and is replaced with a synthetic polynucleotide in which various bases have been altered from the original sequence. The polynucleotide sequence can also be altered by chemical mutagenesis. Chemical mutagens include, for example, sodium bisulfite, nitrous acid, hydroxylamine, hydrazine or formic acid. Other agents which are analogues of nucleotide precursors include nitrosoguanidine, 5-bromouracil, 2-aminopurine, or acridine. Generally, these agents are added to the PCR reaction in place of the nucleotide precursor thereby mutating the sequence. Intercalating agents such as proflavine, acriflavine, quinacrine and the like can also be used. Random mutagenesis of the polynucleotide sequence can also be achieved by irradiation with X-rays or ultraviolet light. Generally, plasmid DNA or DNA fragments so mutagenized are introduced into E. coli and propagated as a pool or library of mutant plasmids.

Alternatively the small mixed population of specific nucleic acids can be found in nature in the form of different alleles of the same gene or the same gene from different related species (i.e., cognate genes). Alternatively, substrates can be related but nonallelic genes, such as the immunoglobulin genes. Diversity can also be the result of previous recombination or shuffling. Diversity can also result from resynthesizing genes encoding natural proteins with alternative codon usage.

The starting substrates encode variant forms of sequences to be evolved. In some methods, the substrates encode variant forms of a protein for which evolution of a new or modified property is desired. In other methods, the substrates can encode variant forms of a plurality of genes constituting a multigene pathway. In such methods, variation can occur in one or any number of the component genes. In other methods, substrates can contain variants segments to be evolved as DNA or RNA binding sequences. In methods, in which starting substrates containing coding sequences, any essential regulatory sequences, such as a promoter and polyadenylation sequence, required for expression may also be present as a component of the substrate. Alternatively, such regulatory sequences can be provided as components of vectors used for cloning the substrates.

The starting substrates can vary in length from about 50, 250, 1000, 10,000, 100,000, $10^6$ or more bases. The starting substrates can be provided in double- or single-stranded form. The starting substrates can be DNA or RNA and analogs thereof. If DNA, the starting substrates can be genomic or cDNA. If the substrates are RNA, the substrates are typically reverse-transcribed to cDNA before heteroduplex formation. Substrates can be provided as cloned fragments, chemically synthesized fragments or PCR amplification products. Substrates can derive from chromosomal, plasmid or viral sources. In some methods, substrates are provided in concatemeric form.

III. Procedures for Generating Heteroduplexes

Heteroduplexes are generated from double stranded DNA substrates, by denaturing the DNA substrates and incubating under annealing conditions. Hybridization conditions for heteroduplex formation are sequence-dependent and are different in different circumstances. Longer sequences hybridize specifically at higher temperatures. Generally, hybridization conditions are selected to be about 25° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium.

Exemplary conditions for denaturation and renaturation of double stranded substrates are as follows. Equimolar concentrations (~1.0–5.0 nM) of the substrates are mixed in 1×SSPE buffer (180 mM NaCl, 1.0 mM EDTA, 10 mM NaH$_2$PO$_4$, pH 7.4) After heating at 96° C. for 10 minutes, the reaction mixture is immediately cooled at 0° C. for 5 minutes; The mixture is then incubated at 68° C. for 2–6 hr. Denaturation and reannealing can also be carried out by the addition and removal of a denaturant such as NaOH. The process is the same for single stranded DNA substrates, except that the denaturing step may be omitted for short sequences.

By appropriate design of substrates for heteroduplex formation, it is possible to achieve selection for heteroduplexes relative to reformed parental homoduplexes. Homoduplexes merely reconstruct parental substrates and effectively dilute recombinant products in subsequent screening steps. In general, selection is achieved by designing substrates such that heteroduplexes are formed in open-circles, whereas homoduplexes are formed as linear molecules. A subsequent transformation step results in substantial enrichment (e.g., 100-fold) for the circular heteroduplexes.

FIG. 1 shows a method in which two substrate sequences in separate vectors are PCR-amplified using two different sets of primers (P1, P2 and P3, P4). Typically, first and second substrates are inserted into separate copies of the same vector. The two different pairs of primers initiate amplification at different points on the two vectors. FIG. 1 shows an arrangement in which the P1/P2 primer pairs initiates amplification at one of the two boundaries of the vector with the substrate and the P1/P2 primer pair initiates replication at the other boundary in a second vector. The two primers in each primer pair prime amplification in opposite directions around a circular plasmid. The amplification products generated by this amplification are double-stranded linearized vector molecules in which the first and second substrates occur at opposite ends of the vector. The amplification products are mixed, denatured and annealed. Mixing and denaturation can be performed in either order. Reannealing generates two linear homoduplexes, and an open circular heteroduplex containing one nick in each strand, at the initiation point of PCR amplification. Introduction of the amplification products into host cells selects for the heteroduplexes relative to the homoduplexes because the former transform much more efficiently than the latter.

It is not essential in the above scheme that amplification is initiated at the interface between substrate and the rest of the vector. Rather, amplification can be initiated at any points on two vectors bearing substrates provided that the amplification is initiated at different points between the vectors. In the general case, such amplification generates two linearized vectors in which the first and second substrates respectively occupy different positions relative to the remainder of the vector. Denaturation and reannealing generator heteroduplexes similar to that shown in FIG. 1, except that the nicks occur within the vector component rather than at the interface between plasmid and substrate. Initiation of amplification outside the substrate component of a vector has the advantage that it is not necessary to design primers specific for the substrate borne by the vector.

Although FIG. 1 is exemplified for two substrates, the above scheme can be extended to any number of substrates. For example, an initial population of vector bearing substrates can be divided into two pools. One pool is PCR-amplified from one set of primers, and the other pool from another. The amplification products are denatured and annealed as before. Heteroduplexes can form containing one strand from any substrate in the first pool and one strand from any substrate in the second pool. Alternatively, three or more substrates cloned into multiple copies of a vector can be subjected to amplification with amplification in each vector starting at a different point. For each substrate, this process generates amplification products varying in how flanking vector DNA is divided on the two sides of the substrate. For example, one amplification product might have most of the vector on one side of the substrate, another amplification product might have most of the vector on the other side of the substrate, and a further amplification product might have an equal division of vector sequence flanking the substrate. In the subsequent annealing step, a strand of substrate can form a circular heteroduplex with a strand of any other substrate, but strands of the same substrate can only reanneal with each other to form a linear homoduplex. In a still further variation, multiple substrates can be performed by performing multiple iterations of the scheme in FIG. 1. After the first iteration, recombinant polynucleotides in a vector, undergo heteroduplex formation with a third substrate incorporated into a further copy of the vector. The vector bearing the recombinant polynucleotides and the vector bearing the third substrate are separately PCR amplified from different primer pairs. The amplification products are then denatured and annealed. The process can be repeated further times to allow recombination with further substrates.

Figure 2:
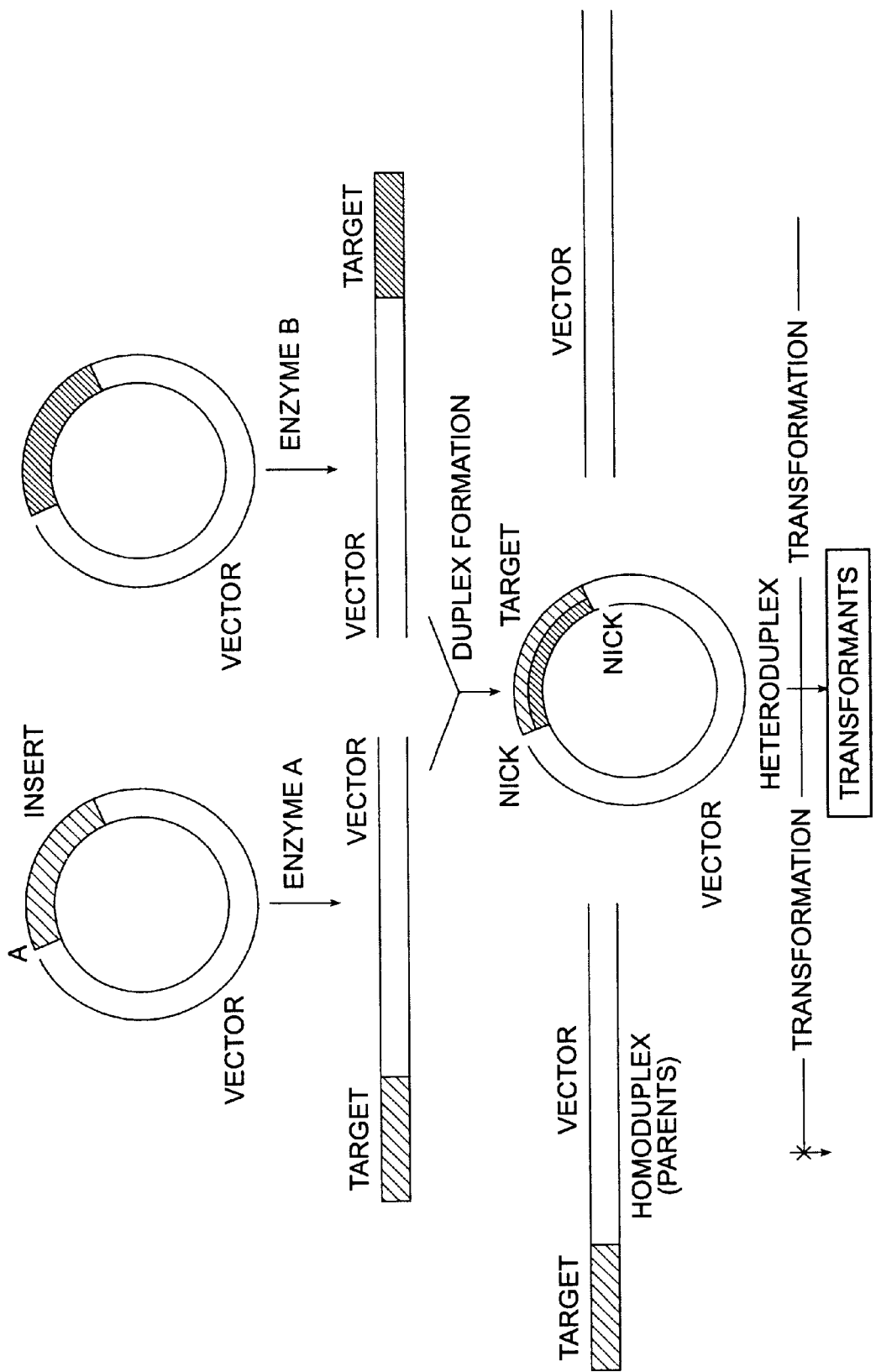
FIG. 2 illustrates the process of heteroduplex formation using restriction enzymes to linearize the target sequences and vector.

An alternative scheme for heteroduplex formation is shown in FIG. 2. Here, first and second substrates are incorporated into separate copies of a vector. The two copies are then respectively digested with different restriction enzymes. FIG. 2 shows an arrangement in which, the restriction enzymes cut at opposite boundaries between substrates and vector, but all that is necessary is to use two different restriction enzymes that cut at different places. Digestion generates linearized first and second vector bearing first and second substrates, the first and second substrates occupying different positions relative to the remaining vector sequences. Denaturation and reannealing generates open circular heteroduplexes and linear homoduplexes. The scheme can be extended to recombination between more than two substrates using analogous strategies to those described with respect to FIG. 1. In one variation, two pools of substrates are formed, and each is separately cloned into vector. The two pools are then cute with different enzymes, and annealing proceeds as for two substrates. In another variation, three or more substrates can be cloned into three or more copies of vector, and the three or more result molecules cut with three or more enzymes, cutting at three or more sites. This generates three different linearized vector forms differing in the division of vector sequences flanking the substrate moiety in the vectors. Alternatively, any number of substrates can be recombined pairwise in an iterative fashion with products of one round of recombination annealing with a fresh substrate in each round.

Figure 3:
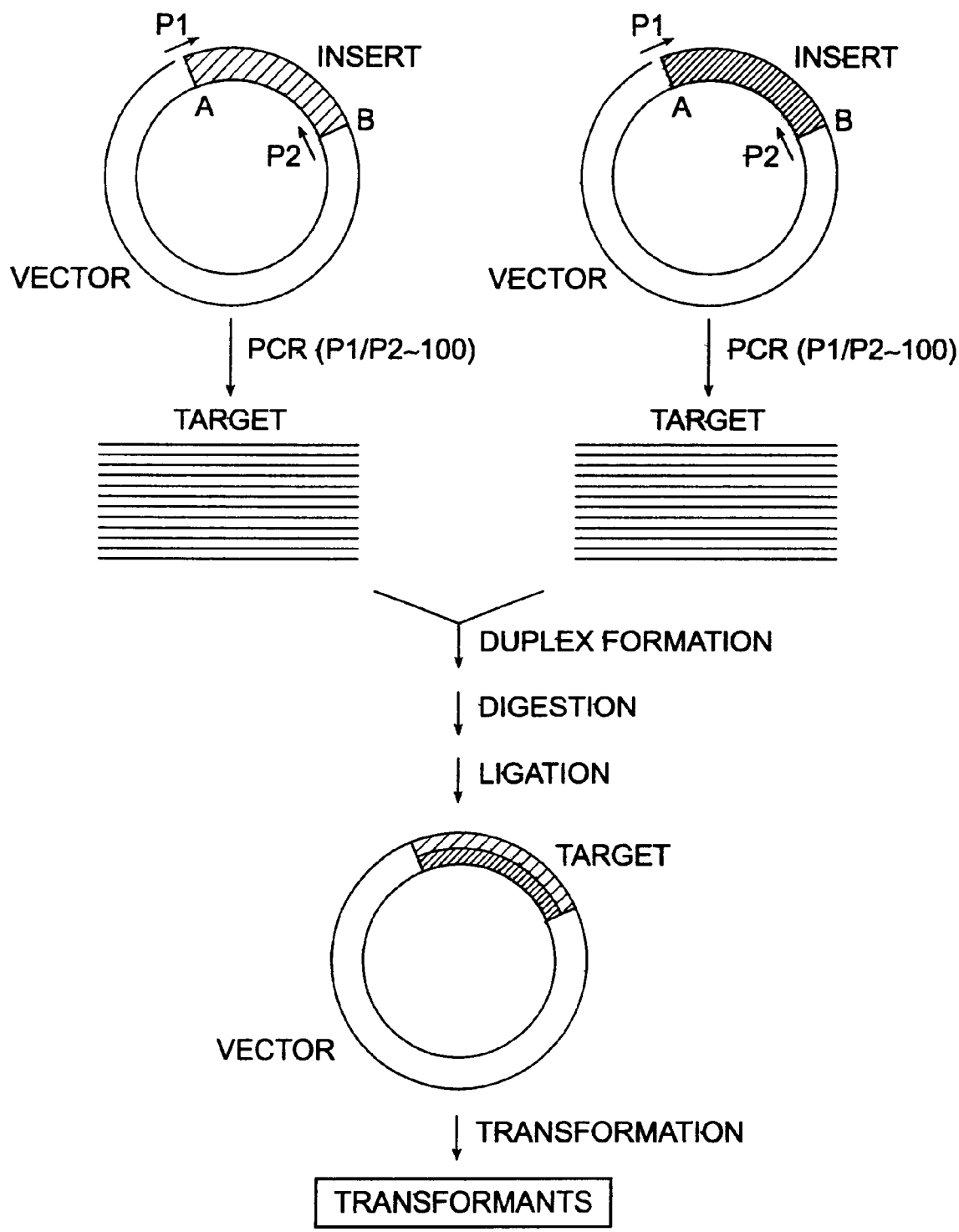
FIG. 3 illustrates a process of heteroduplex formation using asymmetric or single primer polymerase chain reaction (PCR) with one set of primers for each different sequence to amplify the target sequence and vector.

In a further variation, heteroduplexes can be formed from substrates molecules in vector-free form, and the heteroduplexes subsequently cloned into vectors. Such can be achieved by asymmetric amplification of first and second substrates as shown in FIG. 3. Asymmetric or single primer PCR amplifies only one strand of a duplex. By appropriate selection of primers, opposite strands can be amplified from two different substrates. On reannealing amplification products, heteroduplexes are formed from opposite strands of the two substrates. Because only one strand is amplified from each substrate, reannealing does not reform homoduplexes (other than for small quantities of unamplified substrate). The process can be extended to allow recombination of any number of substrates using analogous strategies to those described with respect to FIG. 1. For example, substrates can be divided into two pools, and each pool subject to the same asymmetric amplification, such that amplification products of one pool can only anneal with amplification products of the other pool, and not with each other. Alternatively, shuffling can proceed pairwise in an iterative manner, in which recombinants formed from heteroduplexes of first and second substrates, are subsequently subjected to heteroduplex formation with a third substrate. Point mutations can also be introduced at a desired level during PCR amplification.

Figure 4:
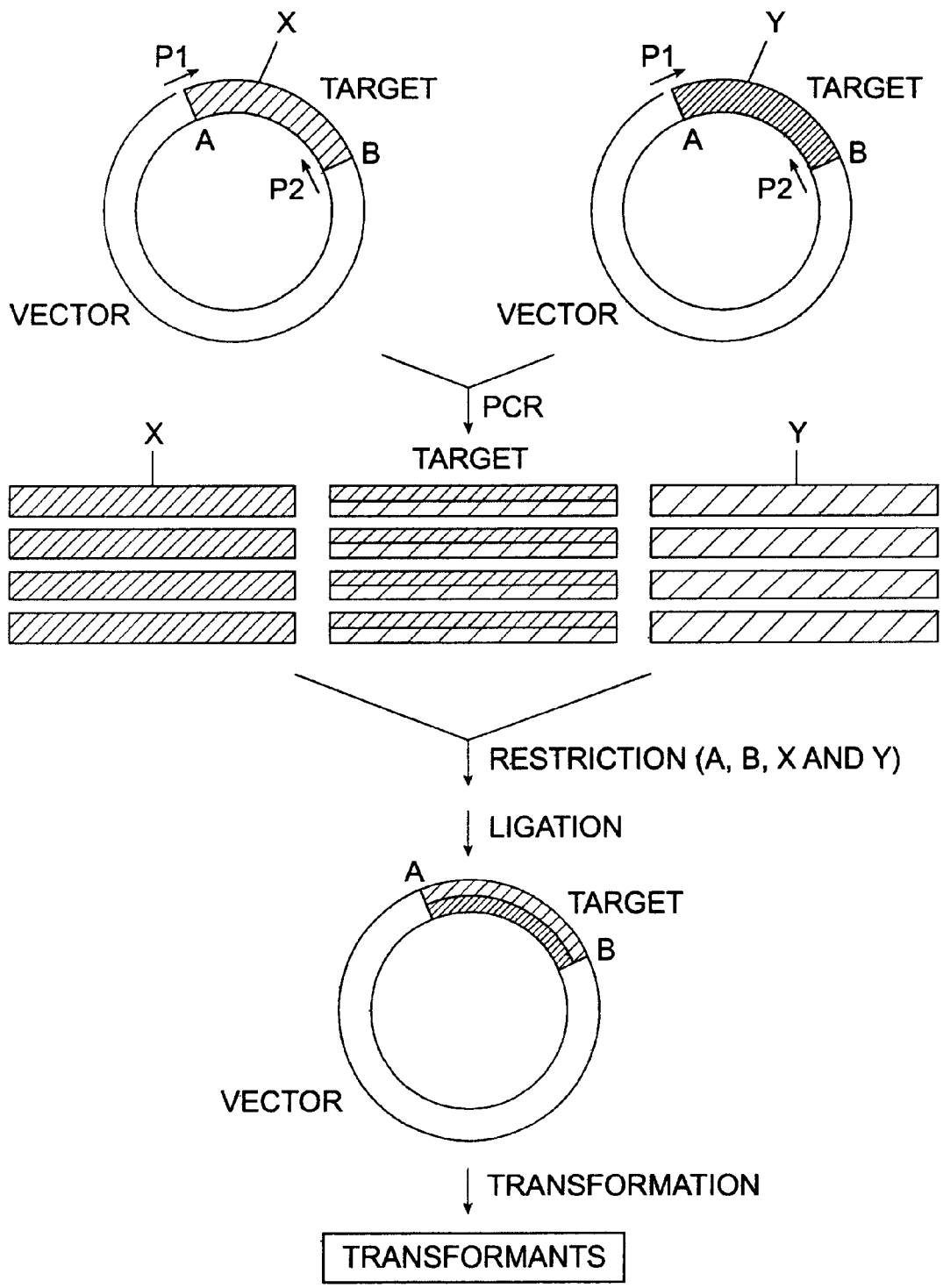
FIG. 4 illustrates heteroduplex recombination using unique restriction enzymes (X and Y) to remove the homoduplexes.

FIG. 4 shows another approach of selecting for heteroduplexes relative to homoduplexes. First and second substrates are:isolated by PCR amplification from separate vectors. The substrates are denatured and allowed to anneal forming both heteroduplexes and reconstructed homoduplexes. The products of annealing are digested with restriction enzymes X and Y. X has a site in the first substrate but not the second substrate, and vice versa for Y. Enzyme X cuts reconstructed homoduplex from the first substrate and enzyme Y cuts reconstructed homoduplex from the second substrate. Neither enzyme cuts heteroduplexes. Heteroduplexes can effectively be separated from restriction fragments of homoduplexes by further cleavage with enzymes A and B having sites proximate to the ends of both the first and second substrates, and ligation of the products into vector having cohesive ends compatible with ends resulting from digestion with A and B. Only heteroduplexes cut with A and B can ligate with the vector. Alternatively, heteroduplexes can be separated from restriction fragments of homoduplexes by size selection on gels. The above process can be generalized to N substrates by cleaving the mixture of heteroduplexes and homoduplexes with N enzymes, each one of which cuts a different substrate and no other substrate. Heteroduplexes can be formed by directional cloning. Two substrates for heteroduplex formation can be obtained by PCR amplification of chromosomal DNA and joined to opposite ends of a linear vector. Directional cloning can be achieved by digesting the vector with two different enzymes, and digesting or adapting first and second substrates to be respectively compatible with cohesive ends of only of the two enzymes used to cut the vector. The first and second substrates can thus be ligated at opposite ends of a linearized vector fragment. This scheme can be extended to any number of substrates by using principles analogous to those described for FIG. 1. For example, substrates can be divided into two pools before ligation to the vector. Alternatively, recombinant products formed by heteroduplex formation of first and second substrates, can subsequently undergo heteroduplex formation with a third substrate.

IV. Vectors and Transformation

In general, substrates are incorporated into vectors either before or after the heteroduplex formation step. A variety of cloning vectors typically used in genetic engineering are suitable.

The vectors containing the DNA segments of interest can be transferred into the host cell by standard methods, depending on the type of cellular host. For example, calcium chloride transformation is commonly utilized for prokaryotic cells, whereas calcium phosphate treatment. Lipofection, or electroporation may be used for other cellular hosts. Other methods used to transform mammalian cells include the use of Polybrene, protoplast fusion, liposomes, electroporation, and microinjection, and biolisitics (see, generally, Sambrook et al., supra). Viral vectors can also be packaged in vitro and introduced by infection. The choice of vector depends on the host cells. In general, a suitable vector has an origin of replication recognized in the desired host cell, a selection maker capable of being expressed in the intended host cells and/or regulatory sequences to support expression of genes within substrates being shuffled.

V. Types of Host Cells

In general any type of cells supporting DNA repair and replication of heteroduplexes introduced into the cells can be used. Cells of particular interest are the standard cell types commonly used in genetic engineering, such as bacteria, particularly, $E.\ coli$ (16, 17). Suitable $E.\ coli$ strains include $E.\ coli$ mutS, mutL, dam$^-$, and/or recA$^+$, $E.coli$ XL-10-Gold ([Tet$^r$Δ(mcrA)183 Δ(mcrCB-hsdSMR-mrr)173 endA1 supE44 thi-1 recA1 gyrA96 relA1 lac Hte] [F'proAB lacI$^q$ZΔM15 Tn10 (Tet$^r$) Amy Cam$^r$]), $E.\ coli$ES1301 mutS [Genotype: lacZ53, mutS201:Tn5, thyA36, rha-5, metB1, deoC, IN(rrnD-rrnE)] (20, 24, 28–42). Preferred $E.\ coli$ strains are $E.\ coli$ SCS 110 [Genotype: rpsl, (Str$^r$), thr, leu, enda, thi-1, lacy, galk, galt, ara tona, tsx, dam, dcm, supE44, Δ(lac-proAB), [F, traD36, proA$^+$B$^+$lacI$^q$ZΔM15], which have normal cellular mismatch repair systems (17). This strain type repairs mismatches and unmatches in the heteroduplex with little strand-specific preference. Further, because this strain is dam$^-$ and dcm$^-$, plasmid isolated from the strain is unmethylated and therefore particularly amenable for further rounds of DNA duplex formation/mismatch repair (see below). Other suitable bacterial cells include gram-negative and gram-positive, such as *Bacillus, Pseudomonas*, and *Salmonella*.

Eukaryotic organisms are also able to carry out mismatch repair (43–48). Mismatch repair systems in both prokaryotes and eukaryotes are thought to play an important role in the maintenance of genetic fidelity during DNA replication, Some of the genes that play important roles in mismatch repair in prokaryotes, particularly mutS and mutL, have homologs in eukaryotes. in the outcome of genetic recombinations, and in genome stability. Wild-type or mutant S. cerevisiae has been shown to carry out mismatch repair of heteroduplexes (49–56), as have COS-1 monkey cells (57). Preferred strains of yeast are Picchia and Saccharomyces. Mammalian cells have been shown to have the capacity to repair G-T to G-C base pairs by a short-patch mechanism (38, 58–63). Mammalian cells (e.g., mouse, hamster, primate, human), both cell lines and primary cultures can also be used. Such cells include stem cells, including embryonic stem cells, zygotes, fibroblasts, lymphocytes, Chinese hamster ovary (CHO), mouse fibroblasts (NIH3T3), kidney, liver, muscle, and skin cells. Other eucaryotic cells of interest include plant cells, such as maize, rice, wheat, cotton, soybean, sugarcane, tobacco, and arabidopsis; fish, algae, fungi (aspergillus, podospora, neurospora), insect (e.g., baculo lepidoptera) (see, Winnacker, "From Genes to Clones," VCH Publishers, New York, (1987), which is incorporated herein by reference).

In vivo repair occurs in a wide variety of prokaryotic and eukaryotic cells. Use of mammalian cells is advantage in certain application in which substrates encode polypeptides that are expressed only in mammalian cells or which are intended for use in mammalian cells. However, bacterial and yeast cells are advantageous for screening large libraries due to the higher transformation frequencies attainable in these strains.

V. In Vitro DNA Repair Systems

As an alternative to introducing annealed products into host cells, annealed products can be exposed a DNA repair system in vitro. The DNA repair system can be obtained as extracts from repair-competent *E. coli*, yeast or any other cells (64–67). Repair-competent cells are lysed in appropriate buffer and supplemented with nucleotides. DNA is incubated in this cell extract and transformed into competent cells for replication.

VI. Screening and Selection

After introduction of annealed products into host cells, the host cells are typically cultured to allow repair and replication to occur and optionally, for genes encoded by polynucleotides to be expressed. The recombinant polynucleotides can be subject to further rounds of recombination using the heteroduplex procedures described above, or other shuffling methods described below. However, whether after one cycle of recombination or several, recombinant polynucleotides are subjected to screening or selection for a desired property. In some instances, screening or selection in performed in the same host cells that are used for DNA repair. In other instances, recombinant polynucleotides, their expression products or secondary metabolites produced by the expression products are isolated from such cells and screened in vitro. In other instances, recombinant polynucleotides are isolated from the host cells in which recombination occurs and are screened or selected in other host cells. For example, in some methods, it is advantageous to allow DNA repair to occur in a bacterial host strain, but to screen an expression product of recombinant polynucleotides in eucaryotic cells. The recombinant polynucleotides surviving screening or selection are sometimes useful products in themselves. In other instances, such recombinant polynucleotides are subjected to further recombination with each other or other substrates. Such recombination can be effected by the heteroduplex methods described above or any other shuffling methods. Further round(s) of recombination are followed by further rounds of screening or selection on an iterative basis. Optionally, the stringency of selection can be increased at each round.

The nature of screening or selection depends on the desired property sought to be acquired. Desirable properties of enzymes include high catalytic activity, capacity to confer resistance to drugs, high stability, the ability to accept a wider (or narrower) range of substrates, or the ability to function in nonnatural environments such as organic solvents. Other desirable properties of proteins include capacity to bind a selected target, secretion capacity, capacity to generate an immune response to a given target, lack of immunogenicity and toxicity to pathogenic microorganisms. Desirable properties of DNA or RNA polynucleotides sequences include capacity to specifically bind a given protein target, and capacity to regulate expression of operably linked coding sequences. Some of the above properties, such as drug resistance, can be selected by plating cells on the drug. Other properties, such as the influence of a regulatory sequence on expression, can be screened by detecting appearance of the expression product of a reporter gene linked to the regulatory sequence. Other properties, such as capacity of an expressed protein to be secreted, can be screened by FACS™, using a labelled antibody to the protein. Other properties, such as immunogenicity or lack thereof, can be screened by isolating protein from individual cells or pools of cells, and analyzing the protein in vitro or in a laboratory animal.

VII. Variations

1. Demethylation

Most cell types methylate DNA in some manner, with the pattern of methylation differing between cells types. Sites of methylation include 5-methylcytosine ($m^5C$), N4-methylcytosine ($m^4C$) and $N^6$-methyladenine ($m^6A$), 5-hydroxymethylcytosine ($hm^5C$) and 5-hydroxymethyluracil ($hm^5U$). In *E. coli*, methylation is effected by Dam and Dcm enzymes. The methylase specified by the dam gene methylates the N6-position of the adenine residue in the sequence GATC, and the methylase specified by the dcm gene methylates the C5-position of the internal cytosine residue in the sequence CCWGG. DNA from plants and mammal is often subject to CG methylation meaning that CG or CNG sequences are methylated. Possible effects of methylated on cellular repair are discussed by references 18–20.

In some methods, DNA substrates for heteroduplex formation are at least partially demethylated on one or both strands, preferably the latter. Demethylation of substrate DNA promotes efficient and random repair of the heteroduplexes. In heteroduplexes formed with one strand dam-methylated and one strand unmethylated, repair is biased to the unmethylated strand, with the methylated strand serving as the template for correction. If neither strand is methylated, mismatch repair occurrs, but showes insignificant strand preference (23, 24).

Demethylation can be performed in a variety of ways. In some methods, substrate DNA is demethylated by PCR-amplification. In some instances, DNA demethylation is accomplished in one of the PCR steps in the heteroduplex formation procedures described above. In other methods, an additional PCR step is performed to effect demethylation. In other methods, demethylation is effected by passaging substrate DNA through methylation deficient host cells (e.g. an *E. coli* dam⁻dcm⁻ strain). In other methods, substrate DNA is demethylated in vitro using a demethylating enzymes. Demethylated DNA is used for heteroduplex formation using the same procedures described above. Heteroduplexes are subsequently introduced into DNA-repair-proficient but restriction-enzyme-defective cells to prevent degradation of the unmethylated heteroduplexes.

2. Sealing Nicks

Several of the methods for heteroduplex formation described above result in circular heteroduplexes bearing nicks in each strand. These nicks can be sealed before introducing heteroduplexes into host cells. Sealing can be effected by treatment with DNA ligase under standard ligating conditions. Ligation forms a phosphodiester bond to link two adjacent bases separated by a nick in one strand of double helix of DNA. Sealing of nicks increases the frequency of recombination after introduction of heteroduplexes into host cells.

3. Error Prone PCR Attendant To Amplification

Several of the formats described above include a PCR amplification step. Optionally, such a step can be performed under mutagenic conditions to induce additional diversity between substrates.

VIII. Other Shuffling Methods

The methods of heteroduplex formation described above can be used in conjunction with other shuffling methods. For example, one can perform one cycle of heteroduplex shuffling, screening or selection, followed by a cycle of shuffling by another method, followed by a further cycle of screening or selection. Other shuffling formats are described by WO 95/22625; U.S. Pat. No. 5,605,793; U.S. Pat. No. 5,811,238; WO 96/19256; Stemmer, *Science* 270, 1510 (1995); Stemmer et al., *Gene*, 164, 49–53 (1995); Stemmer, *Bio/Technology*, 13, 549–553 (1995); Stemmer, *Proc. Natl. Acad. Sci.* USA 91, 10747–10751 (1994); Stemmer, *Nature*

370, 389–391 (1994); Crameri et al., *Nature Medicine*, 2(1):1–3, (1996); Crameri et al., *Nature Biotechnology* 14, 315–319 (1996); WO 98/42727; WO 98/41622; WO 98/05764 and WO 98/42728, WO 98/27230 (each of which is incorporated by reference in its entirety for all purposes).

IX. Protein Analogs

Proteins isolated by the methods also serve as lead compounds for the development of derivative compounds. The derivative compounds can include chemical modifications of amino acids or replace amino acids with chemical structures. The analogs should have a stabilized electronic configuration and molecular conformation that allows key functional groups to be presented in substantially the same way as a lead protein. In particular, the non-peptic compounds have spatial electronic properties which are comparable to the polypeptide binding region, but will typically be much smaller molecules than the polypeptides, frequently having a molecular weight below about 2 CHD and preferably below about 1 CHD. Identification of such non-peptic compounds can be performed through several standard methods such as self-consistent field (CSF) analysis, configuration interaction (CHI) analysis, and normal mode dynamics analysis. Computer programs for implementing these techniques are readily available. See Rein et al., *Computer-Assisted Modeling of Receptor-Ligand Interactions* (Alan Liss, New York, 1989).

IX. Pharmaceutical Compositions

Polynucleotides, their expression products, and secondary metabolites whose formation is catalyzed by expression products, generated by the above methods are optionally formulated as pharmaceutical compositions. Such a composition comprises one or more active agents, and a pharmaceutically acceptable carrier. A variety of aqueous carriers can be used, e.g., water, buffered water, phosphate-buffered saline (PBS), 0.4% saline, 0.3% glycine, human albumin solution and the like. These solutions are sterile and generally free of particulate matter. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride and sodium is selected primarily based on fluid volumes, viscosities, and so forth, in accordance with the particular mode of administration selected.

EXAMPLES

Example 1

Novel *Rhizobium Flaa* Genes from Recombination of *Rhizobium Lupini* Flaa And *Rhizobium Meliloti* FlaA Bacterial flagella have a helical filament, a proximal hook and a basal body with the flagellar motor (68). This basic design has been extensively examined in *E. coli* and *S. typhimurium* and is broadly applicable to many other bacteria as well as some archaea. The long helical filaments are polymers assembled from flagellin subunits, whose molecular weights range between 20,000 and 65,000, depending on the bacterial species (69). Two types of flagellar filaments, named plain and complex, have been distinguished by their electron microscopically determined surface structures (70). Plain filaments have a smooth surface with faint helical lines, whereas complex filaments exhibit a conspicuous helical pattern of alternating ridges and grooves. These characteristics of complex flagellar filaments are considered to be responsible for the brittle and (by implication) rigid structure that enables them to propel bacteria efficiently in viscous media (71–73). Whereas flagella with plain filaments can alternate between clockwise and counter clockwise rotation (68), all known flagella with complex filaments rotate only clockwise with intermittent stops (74). Since this latter navigation pattern is found throughout bacteria and archaea, it has been suggested that complex flagella may reflect the common background of an ancient, basic motility design (69).

Differing from plain bacterial flagella in the fine structure of their filaments dominated by conspicuous helical bands and in their fragility, the filaments are also resistant against heat decomposition (72). Schmitt et al. (75) showed that bacteriophage 7-7-1 specifically adsorbs to the complex flagella of *R. lupini* H 13-3 and requires motility for a productive infection of its host. Though the flagellins from *R. meliloti* and *R. lupini* are quite similar, bacteriophage 7-7-1 does not infect *R.meliloti*. Until now complex flagella have been observed in only three species of soil bacteria: *Pseudomonas rhodos* (73), *R.meliloti* (76), and *R. lupini* H13-3 (70, 72). Cells of *R.lupini* H13-3 posses 5 to 10 peritrichously inserted complex flagella, which were first isolated and analyzed by high resolution electron microscopy and by optical diffraction (70).

Maruyama et al. (77) further found that a higher content of hydrophobic amino acid residues in the complex filament may be one of the main reasons for the unusual properties of complex flagella. By measuring mass per unit length and obtaining three-dimensional reconstruction from electron micrographs, Trachtenberg et al. (73, 78) suggested that the complex filaments of *R. lupini* are composed of functional dimers. FIG. 6 shows the comparison between the deduced amino acid sequence of the *R. lupini* H13-3 FlaA and the deduced amino acid sequence of the *R. meliloti* FlaA. Perfect matches are indicated by vertical lines, and conservative exchanges are indicated by colons. The overall identity is 56%. The *R.lupini* flaA and *R.meliloti* flaA were subjected to in vitro heteroduplex formation followed by in vivo repair in order to create novel FlaA molecules and structures.

Figure 6A:
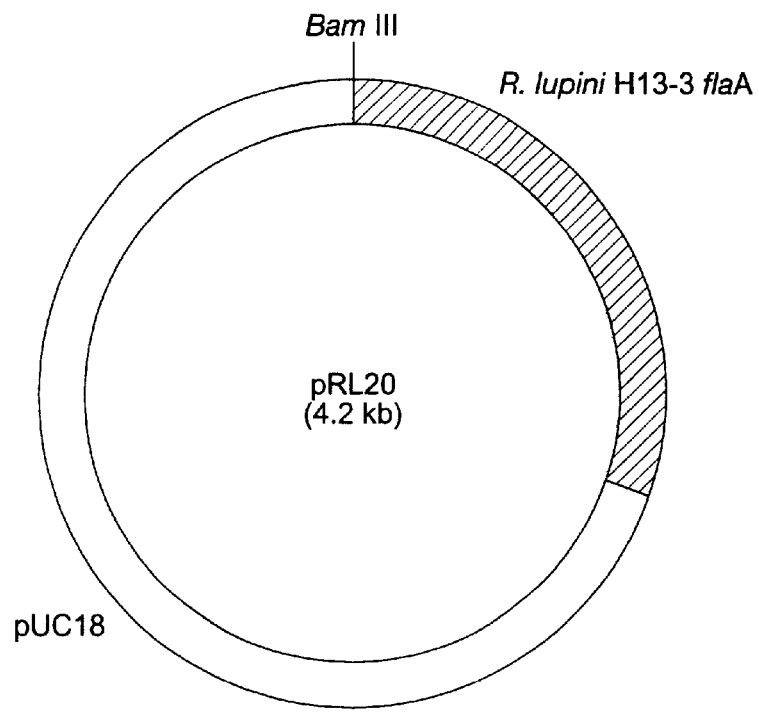
FIG. 6 shows the locations of the unique restriction sites utilized to linearize pRL20 and pRM40.
Figure 6B:
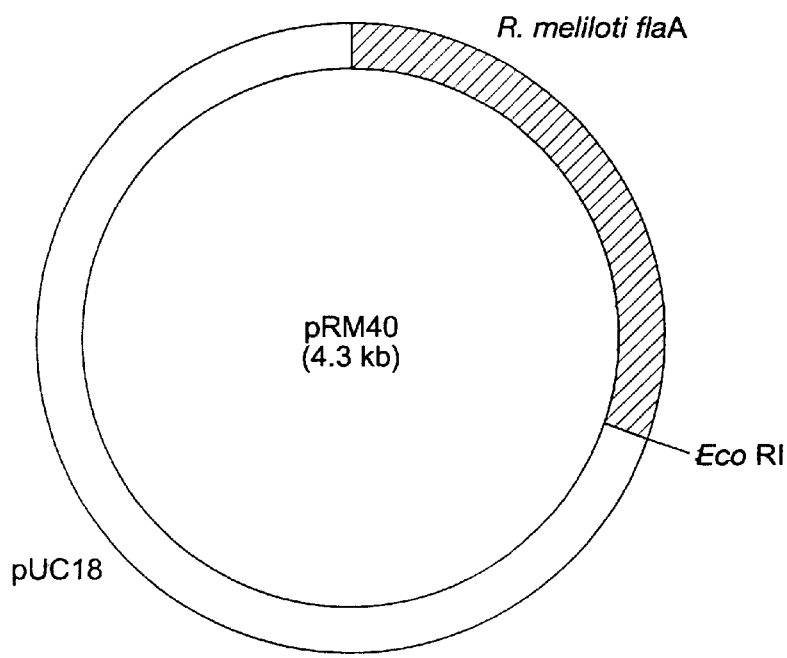

A. Methods pRL20 containing *R. lupini* H-13-3 flaA gene and pRM40 containing *R.meliloti* flaA gene are shown in FIGS. 6A and 6B. These plasmids were isolated from *E. coli* SCS110 (free from dam- and dcm-type methylation). About 3.0 pg. of unmethylated pRL20 and pRM40 DNA were digested with Bam HI and Eco RI, respectively, at 37° C. for 1 hour. After agarose gel separation, the linearized DNA was purified with Wizard PCR Prep kit (Promega, Wis., USA). Equimolar concentrations (2.5 nM) of the linearized unmethylated pRL20 and pRM40 were mixed in 1×SSPE buffer (180 mM NaCl, 1 mM EDTA, 10 mM NaH2PO4, pH 7.4). After heating at 96° C. for 10 minutes, the reaction mixture was immediately cooled at 0° C. for 5 minutes. The mixture was incubated at 68° C. for 2 hour for heteroduplexes to form.

One microliter of the reaction mixture was used to transform 50μ of *E. coli* ES 1301 mutS, *E. coli* SCS110 and *E. coli* JM109 competent cells. The transformation efficiency with *E. coli* JM109 competent cells was about seven times higher than that of *E. coli* SCS110 and ten times higher than that of *E. coli* ES1301 mutS, although the overall transformation efficiencies were 10–200 times lower than those of control transformations with the close, covalent and circular pUC19 plasmid.

Two clones were selected at random from the E. coli SCS110 transformants and two from E. coli ES1301 mutS transformants, and plasmid DNA was isolated from these four clones for further DNA sequencing analysis.

B. Results

Figure 8:
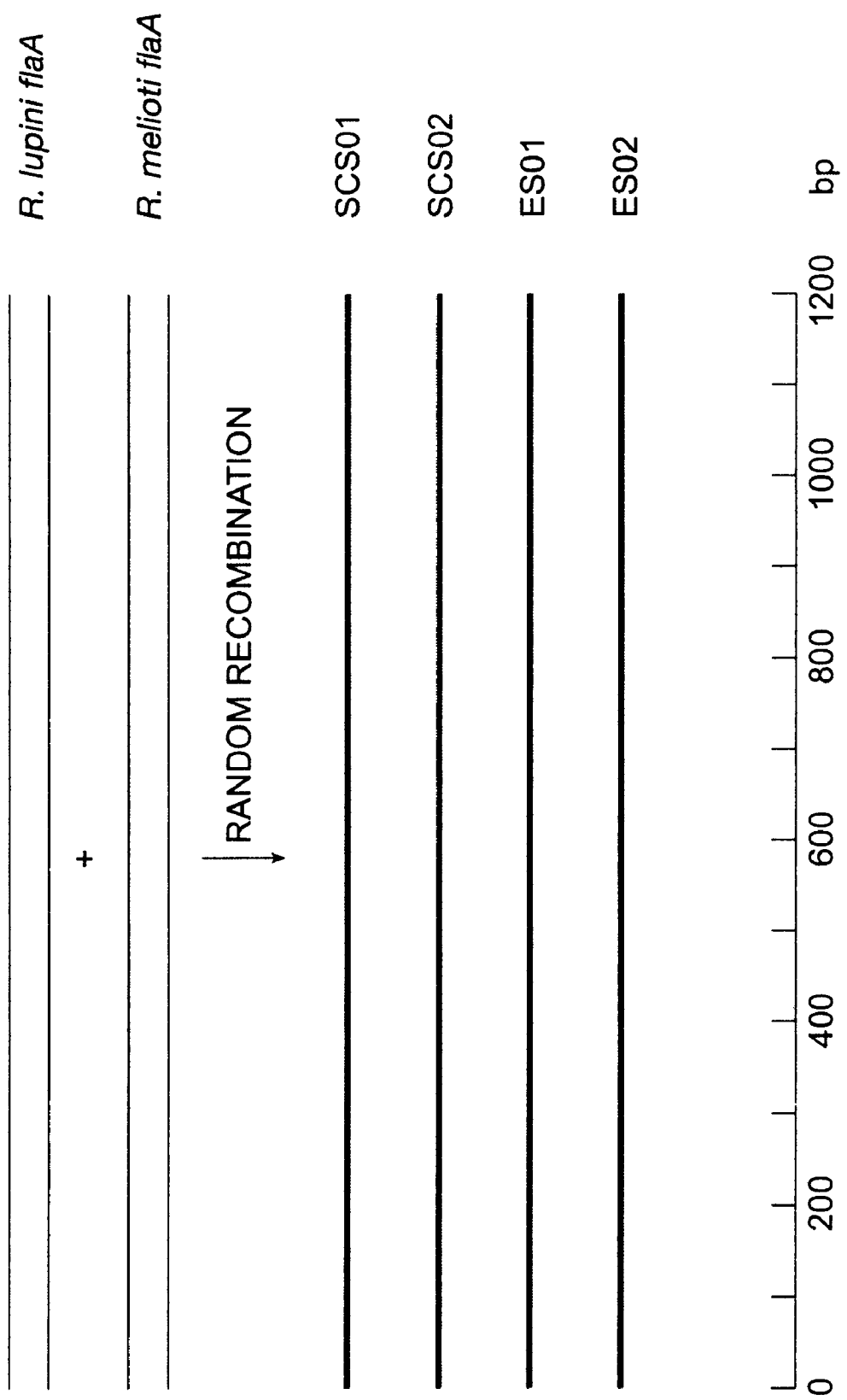
FIG. 8 illustrates how the heteroduplex repair process created mosaic flaA genes containing sequence information from both parent genes.

FIG. 7 shows (a) the sequence of SCS01 (clone#1 from E. coli SCS110 transformant library), (b) the sequence of SCS02 (clone #2 from E. coli SCS110 transformant library), (c) the sequence of ES01 (clone #1 from E. coli ES1301 transformant library), and (d) the sequence of ES02 (clone #2 from E. coli ES1301 transformant library). All four sequences were different from wild-type R. lupini flaA and R. meliloti flaA sequences. Clones SCS02, ES01 and ES02 all contain a complete open-reading frame, but SCS01 was truncated. FIG. 8 shows that recombination mainly occurred in the loop regions (unmatched regions). The flaA mutant library generated from R. meliloti flaA and R. lupini flaA can be transformed into E. coli SCS110, ES1301, XL10-Gold and JM109, and transformants screened for functional FlaA recombinants.

Example 2

Directed Evolution of ECB Deacylase for Variants with Enhanced Specific Activity Streptomyces are among the most important industrial microorganisms due to their ability to produce numerous important secondary metabolites (including many antibiotics) as well as large amounts of enzymes. The approach described here can be used with little modification for directed evolution of native Streptomyces enzymes, some or all of the genes in a metabolic pathways, as well as other heterologous enzymes expressed in Streptomyces.

New antifungal agents are critically needed by the large and growing numbers of immune-compromised AIDS, organ transplant and cancer chemotherapy patients who suffer opportunistic infections. Echinocandin B (ECB), a lipopeptide produced by some species of Aspergillus, has been studied extensively as a potential antifungal. Various antifungal agents with significantly reduced toxicity have been generated by replacing the linoleic acid side chain of A. nidulans echinocandin B with different aryl side chains (79–83). The cyclic hexapeptide ECB nucleus precursor for the chemical acylation is obtained by enzymatic hydrolysis of ECB using Actinoplanes utahensis ECB deacylase. To maximize the conversion of ECB into intact nucleus, this reaction is carried out at pH 5.5 with a small amount of miscible organic solvent to solubilize the ECB substrate. The product cyclic hexapeptide nucleus is unstable at pH above 5.5 during the long incubation required to fully deacylate ECB (84). The pH optimum of ECB deacylase, however, is 8.0–8.5 and its activity is reduced at pH 5.5 and in the presence of more than 2.5% ethanol (84). To improve production of ECB nucleus it is necessary to increase the activity of the ECB deacylase under these process-relevant conditions.

Relatively little is known about ECB deacylase. The enzyme is a heterodimer whose two subunits are derived by processing of a single precursor protein (83). The 19.9 kD α-subunit is separated from the 60.4 kD β-subunit by a 15-amino acid spacer peptide that is removed along with a signal peptide and another spacer peptide in the native organism. The polypeptide is also expressed and processed into functional enzyme in Streptomyces lividans, the organism used for large-scale conversion of ECB by recombinant ECB deacylase. The three-dimensional structure of the enzyme has not been determined, and its sequence shows so little similarity to other possibly related enzymes such as penicillin acylase that a structural model reliable enough to guide a rational effort to engineer the ECB deacylase will be difficult to build. We therefore decided to use directed evolution (85) to improve this important activity.

Protocols suitable for mutagenic PCR and random-priming recombination of the 2.4 kb ECB deacylase gene (73% G+C) have been described recently (86). Here, we further describe the use of heteroduplex recombination to generate new ECB deacylase with enhanced specific activity.

In this case, two Actinoplanes utahensis ECB deacylase mutants, M7-2 and M16, which show higher specific activity at pH 5.5 and in the presence of 10% MeOH were recombined using technique of the in vitro heteroduplex formation and in vivo mismatch repair.

Figure 12:
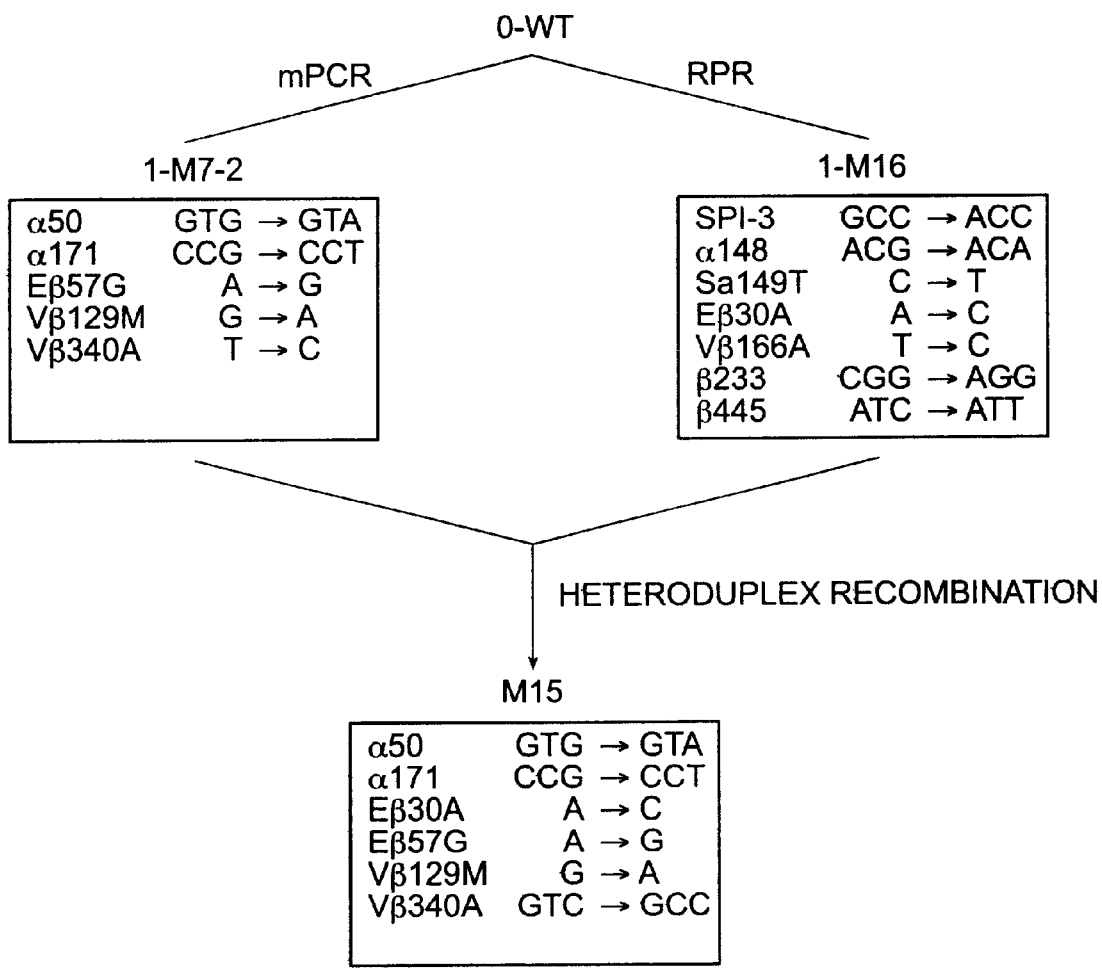
FIG. 12. Positions of DNA base changes and amino acid substitutions in recombined ECB deacylase Mutant 15 with respect to parental sequences of Mutant 7-2 and Mutant 16.

FIG. 12 shows the physical maps of plasmids pM7-2 and pM16 which contain the genes for the M7-2 and M16 ECB deacylase mutants. Mutant M7-2 was obtained through mutagenic PCR performed directly on whole Streptomyces lividans cells containing wild-type ECB deacylase gene, expressed from plasmid pSHP150-2*. Streptomyces with pM7-2 show 1.5 times the specific activity of cells expressing the wild-type ECB deacylase (86). Clone pM16 was obtained using the random-priming recombination technique as described (86, 87). It shows 2.4 times specific activity of the wild-type ECB deacylase clone.

Figure 9A:
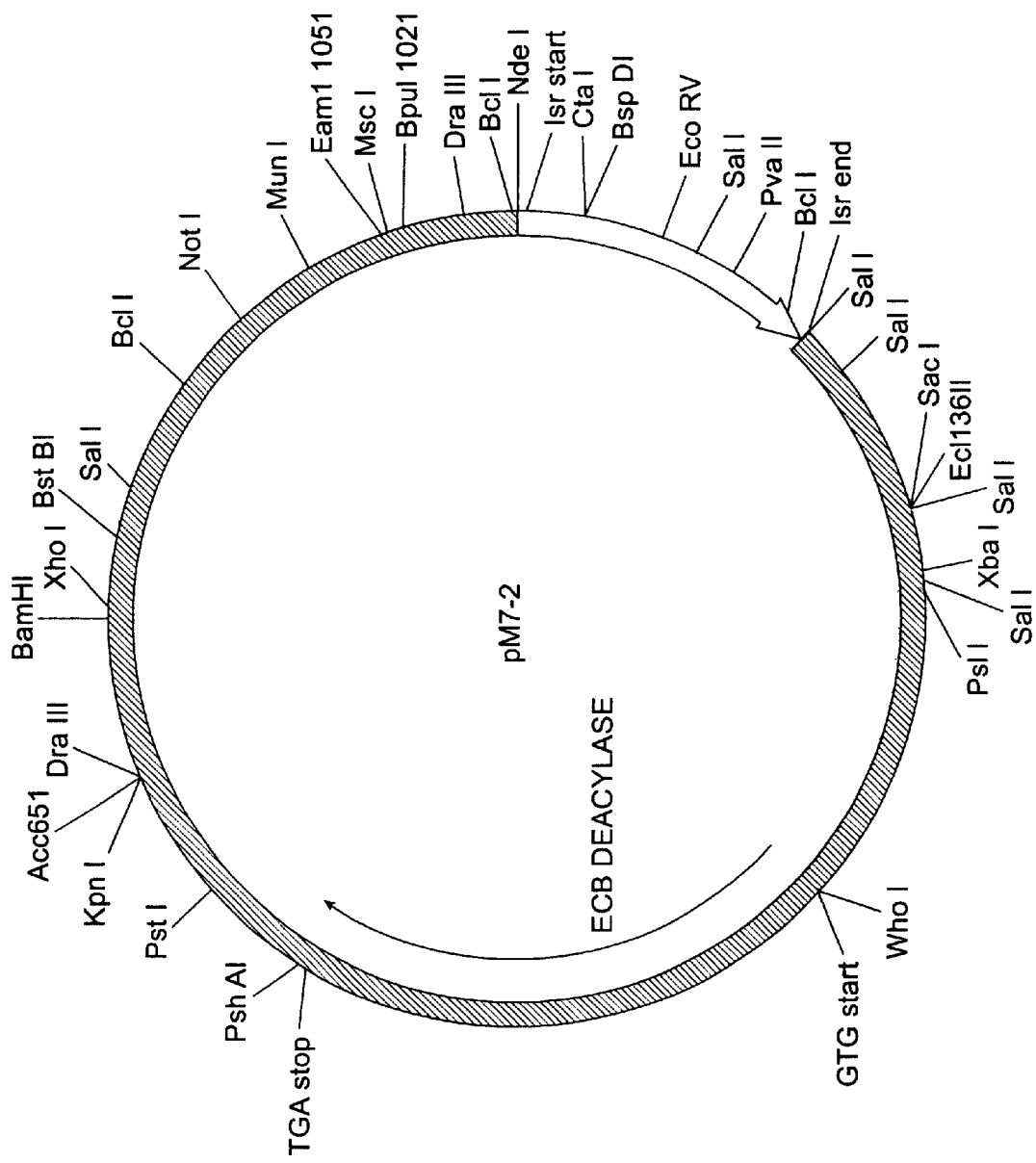
FIG. 9 shows the physical maps of *Actinoplanes utahensis* ECB deacylase mutants with enhanced specific activity ((a) is pM7-2 for Mutant 7-2, and (b) is pM16 for Mutant 16).
Figure 9B:
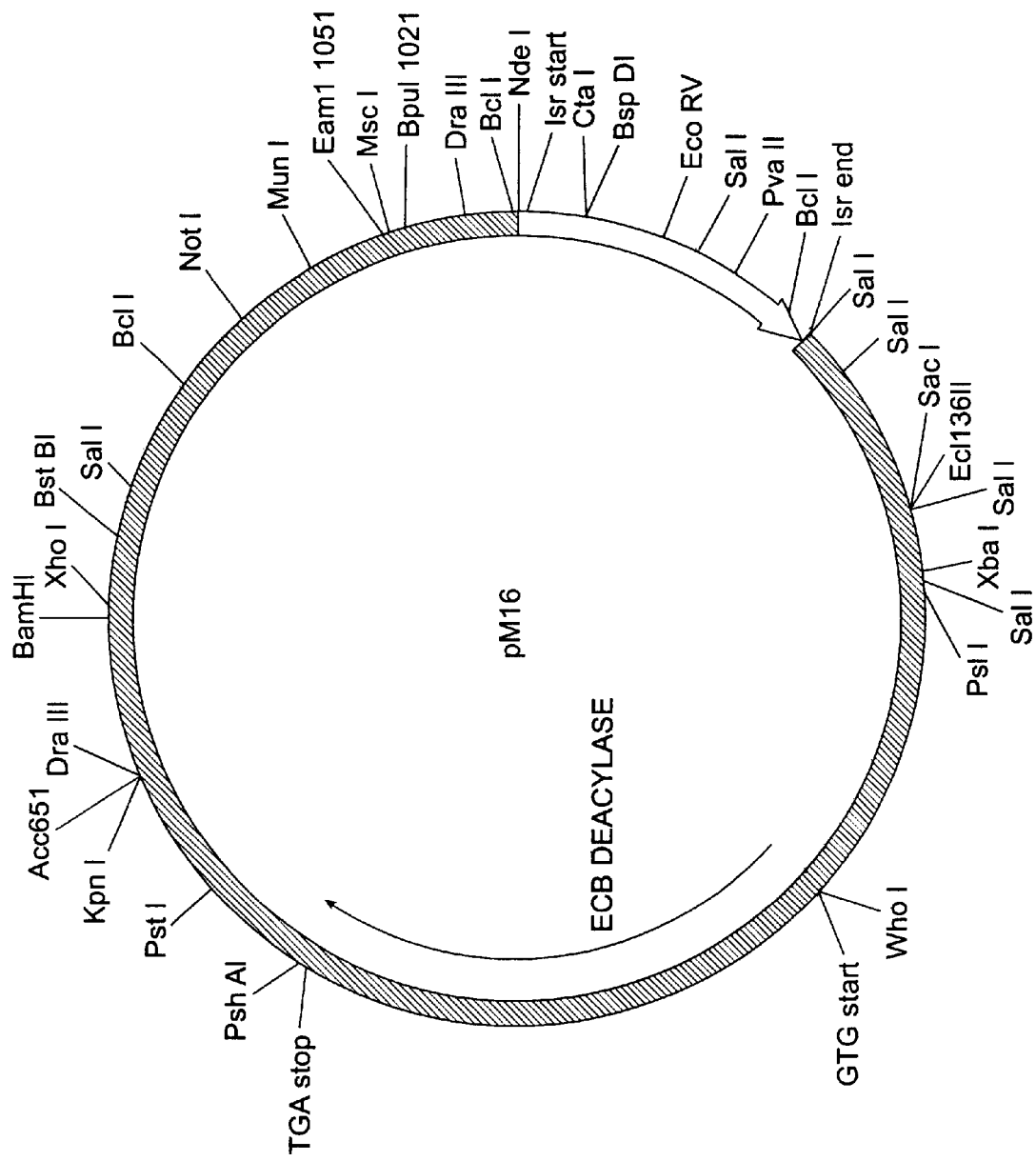
Figure 10:
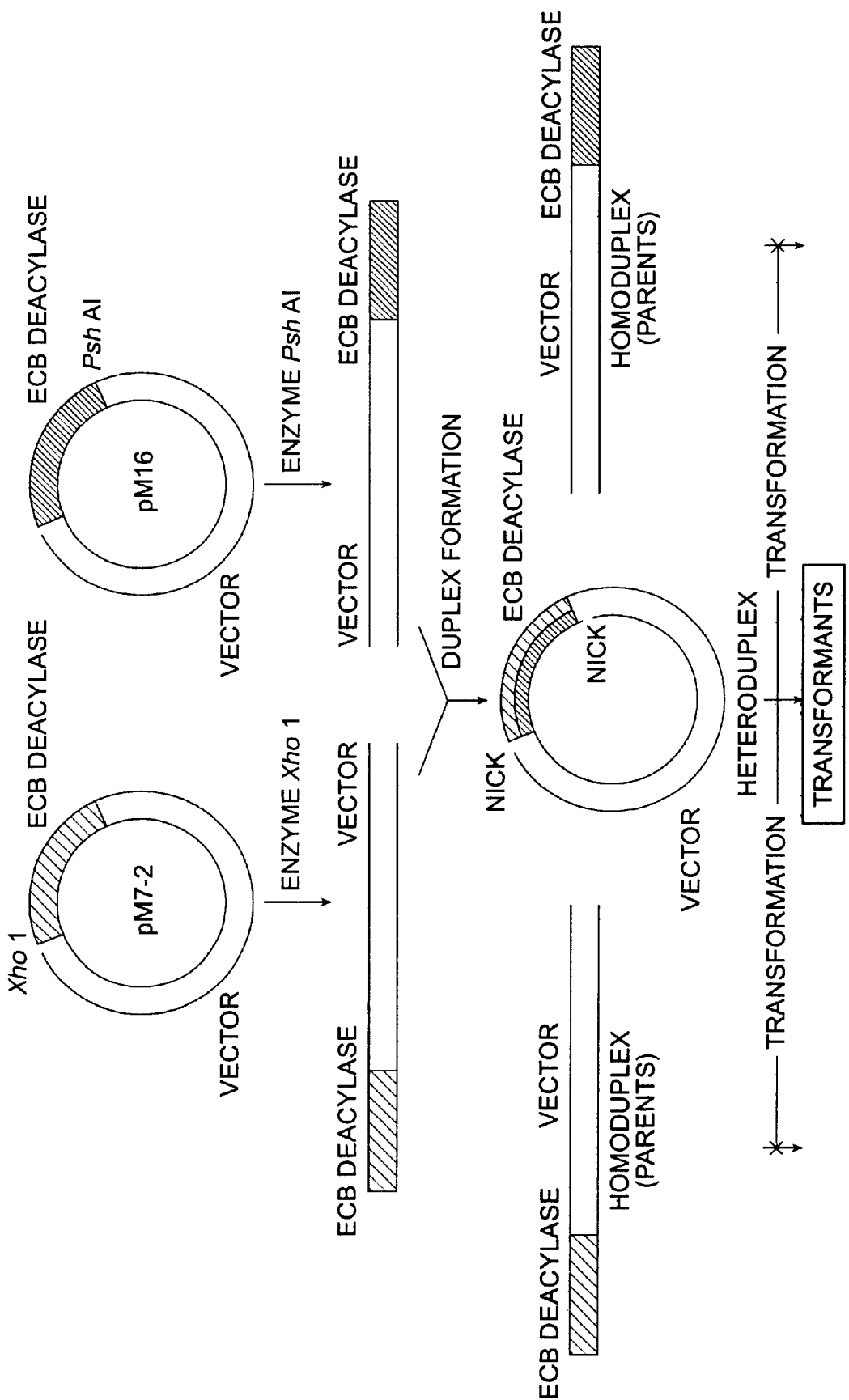
FIG. 10 illustrates the process used for Example 2 to recombine mutations in Mutant 7-2 and Mutant 16 to yield ECB deacylase recombinant with more enhanced specific activity.

A. Methods:

M7-2 and M16 plasmid DNA (pM7-2 and pM16) (FIG. 9) were purified from E. coli SCS210 (in separate reactions). About 5.0 µg of unmethylated M7-2 and M16 DNA were digested with Xho I and Psh AI, respectively, at 37° C. for 1 hour (FIG. 10). After agarose gel separation, the linearized DNA was purified using a Wizard PCR Prep Kit (Promega, Wis., USA). Equimolar concentrations (2.0 nM) of the linearized unmethylated pM7-2 and pM16 DNA were mixed in 1×SSPE buffer (1×SSPE: 180 mM NaCl, 1.0 mM EDTA, 10 mM $NaH_2PO_4$, pH 7.4). After heating at 96° C. for 10 minutes, the reaction mixture is immediately cooled at 0° C. for 5 minutes. The mixture was incubated at 68° C. for 3 hours to promote formation of heteroduplexes.

One microliter of the reaction mixture was used to transform 50 µl of E.coli ES1301 mutS, SCS110 and JM109 competent cells. All transformants from E. coli ES1301 mutS were pooled and E. coli SCS110 were pooled. A plasmid pool was isolated from each pooled library, and this pool was used to transform S. lividans TK23 protoplasts to form a mutant library for deacylase activity screening. Transformants from the S. lividans TK23 libraries were screened for ECB deacylase activity with an in situ plate assay. Transformed protoplasts were allowed to regenerate on R2YE agar plates for 24 hr at 30° C. and to develop in the presence of thiostrepton for 48 hours. When the colonies grew to the proper size, 6 ml of 0.7% agarose solution containing 0.5 mg/ml ECB in 0.1 M sodium acetate buffer (pH 5.5) was poured on top of each R2YE-agar plate and allowed to develop for 18–24 hr at 30° C. Colonies surrounded by a clearing zone larger than that of a control colony containing wild-type plasmid pSHP150–2*, were selected for further characterization.

Selected transformants were inoculated into 20 ml medium containing thiostrepton and grown aerobically at 30° C. for 48 hours, at which point they were analyzed for ECB deacylase activity using HPLC. 100 µl of whole broth was used for a reaction at 30° C. for 30 minutes in 0.1 M NaAc buffer (pH 5.5) containing 10% (v/v) MeOH and 200 µg/ml of ECB substrate. The reactions were stopped by adding 2.5 volumes of methanol, and 20 µl of each sample were analyzed by HPLC on a 100×4.6 mm polyhydroxyethyl aspartamide column (PolyLC Inc., Columbia, Md., USA) at room temperature using a linear acetonitrile gradient starting with 50:50 of A:B (A=93% acetonitrile, 0.1% phosphoric acid; B=70% acetonitrile, 0.1% phosphoric acid) and ending with 30:70 of A:B in 22 min at a flow rate of 2.2 ml/min. The areas of the ECB and ECB nucleus peaks were calculated and subtracted from the areas of the corresponding peaks from a sample culture of S. lividans containing pIJ702* in order to estimate the ECB deacylase activity.

2.0 ml pre-cultures of positive mutants were used to inoculate 50-ml medium and allowed to grow at 30° C. for 96 hr. The supernatants were further concentrated to 1/30 their original volume using an Amicon filtration unit (Beverly, Mass., USA) with molecular weight cutoff of 10 kD. The resulting enzyme samples were diluted with an equal volume of 50 mM $KH_2PO4$ (pH 6.0) buffer and were applied to Hi-Trap ion exchange column (Pharmacia Biotech, Piscataway, N.J., USA). The binding buffer was 50 mM $KH_2PO_4$ (pH 6.0), and the elution buffer was 50 mM $KH_2PO_4$ (pH 6.0) containing 1.0 M NaCl. A linear gradient from 0 to 1.0 M NaCl was applied in 8 column volumes with a flow rate of 2.7 ml/min. The ECB deacylase fraction eluting at 0.3 M NaCl was concentrated and the buffer was exchanged for 50 MM $KH_2PO_4$ (pH 6.0) using Centricon-10 units. Enzyme purity was verified by SDS-PAGE using Coomassie Blue stain, and the concentration was determined using the Bio-Rad Protein Assay Reagent (Hercules, Calif., USA).

A modified HPLC assay was used to determine the activities of the ECB deacylase mutants on ECB substrate (84). Four µg of each purified ECB deacylase mutant was used for activity assay reaction at 30° C. for 30 minutes in 0.1 M NaAc buffer (pH 5.5) containing 10% (v/v) MeOH and different concentrations of ECB substrate. Assays were performed in duplicate. The reactions were stopped by adding 2.5 volumes of methanol, and the HPLC assays were carried out as described above. The absorbance values were recorded, and the initial rates were calculated by least-squares regression of the time progress curves from which the Km and the kcat were calculated.

Activities as a function of pH were measured for the purified ECB deacylases at 30° C. at different pH values: 5, 5.5 and 6 (0.1 M acetate buffer); 7, 7.5, 8 and 8.5 (0.1 M phosphate buffer); 9 and 10 (0.1 M carbonate buffer) using the HPLC assay. Stabilities of purified ECB deacylases were were determined at 30° C. in 0.1 M NaAc buffer (pH 5.5) containing 10% methanol. Samples were withdrawn at different time intervals, and the residual activity was measured in the same buffer with the HPLC assay described above.

B. Results

Figure 11:
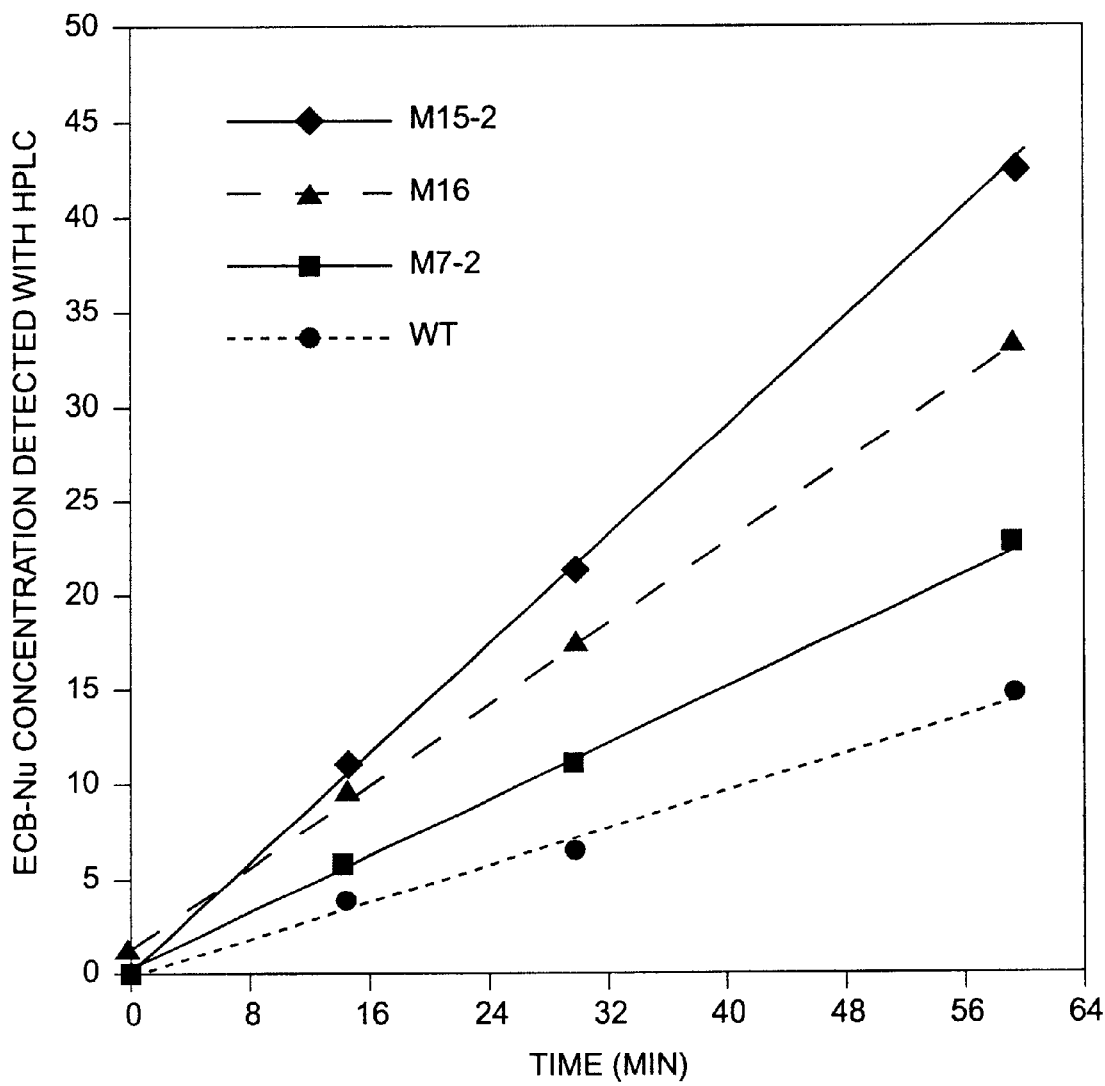
FIG. 11 Specific activities of wild-type ECB deacylase and improved mutants Mutant 7-2, Mutant 16 and recombined Mutant 15.

FIG. 11 shows that after one round of applying this heteroduplex repair technique on the mutant M7-2 and M16 genes, one mutant (M15) from about 500 original transformants was found to possess 3.1 times the specific activity of wild-type. Wild type and evolved M15 ECB deacylases were purified and their kinetic parameters for deacylation of ECB were determined by HPLC. The evolved deacylases M15 has an increased catalytic rate constant, $k_{cat}$ by 205%. The catalytic efficiency ($k_{cat}/K_m$) of M20 is enhanced by a factor of 2.9 over the wild-type enzyme.

Initial rates of deacylation with the wild type and M15 at different pH values from 5 to 10 were determined at 200 µg/ml of ECB. The recombined M15 is more active than wild type at pH 5–8. Although the pH dependence of the enzyme activity in this assay is not strong, there is a definite shift of 1.0–1.5 units in the optimum to lower pH, as compared to wild type.

The time courses of deactivation of the purified ECB deacylase mutant M15 was measured in 0.1 M NaAc (pH 5.5) at 30° C. No significant difference in stability was observed between wild type and mutant M15.

The DNA mutations with respect to the wild type ECB deacylase sequence and the positions of the amino acid substitutions in the evolved variants M7-2, M16 and M15 are summarized in FIG. 12.

The heteroduplex recombination technique can recombine parent sequences to create novel progeny. Recombination of the M7-2 and M16 genes yielded M15, whose activity is higher than any of its parents (Fid. 13). Of the six base substitutions in M15, five (at positions α50, α71, β57, β129 and β340) were inherited from M7-2, and the other one (β30) came from M16.

This approach provides an alternative to existing methods of DNA recombination and is particularly useful in recombining large genes or entire operons. This method can be used to create recombinant proteins to improve their properties or to study structure-function relationship.

Example 3

Novel Thermostable *Bacillus Subtilis* Subtilisin E Variants

This example demonstrates the use in vitro heteroduplex formation followed by in vivo repair for combining sequence information from two different sequences in order to improve the thermostability of *Bacillus subtilis* subtilisin E.

Figure 14:
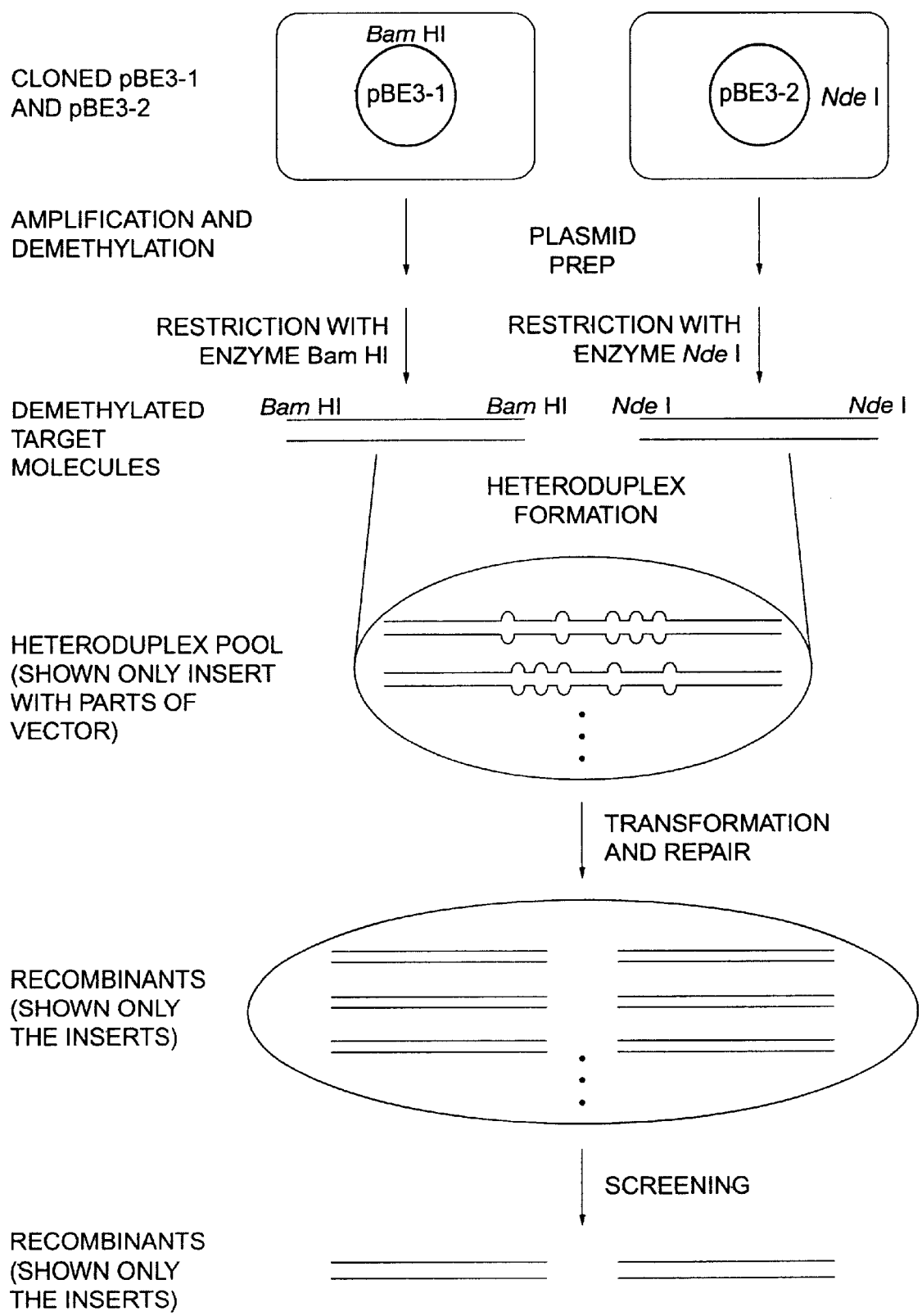
FIG. 14 illustrates the process used for Example 3 to recombine mutations in RC1 and RC2 to yield thermostable subtilisin E.
Figure 15:
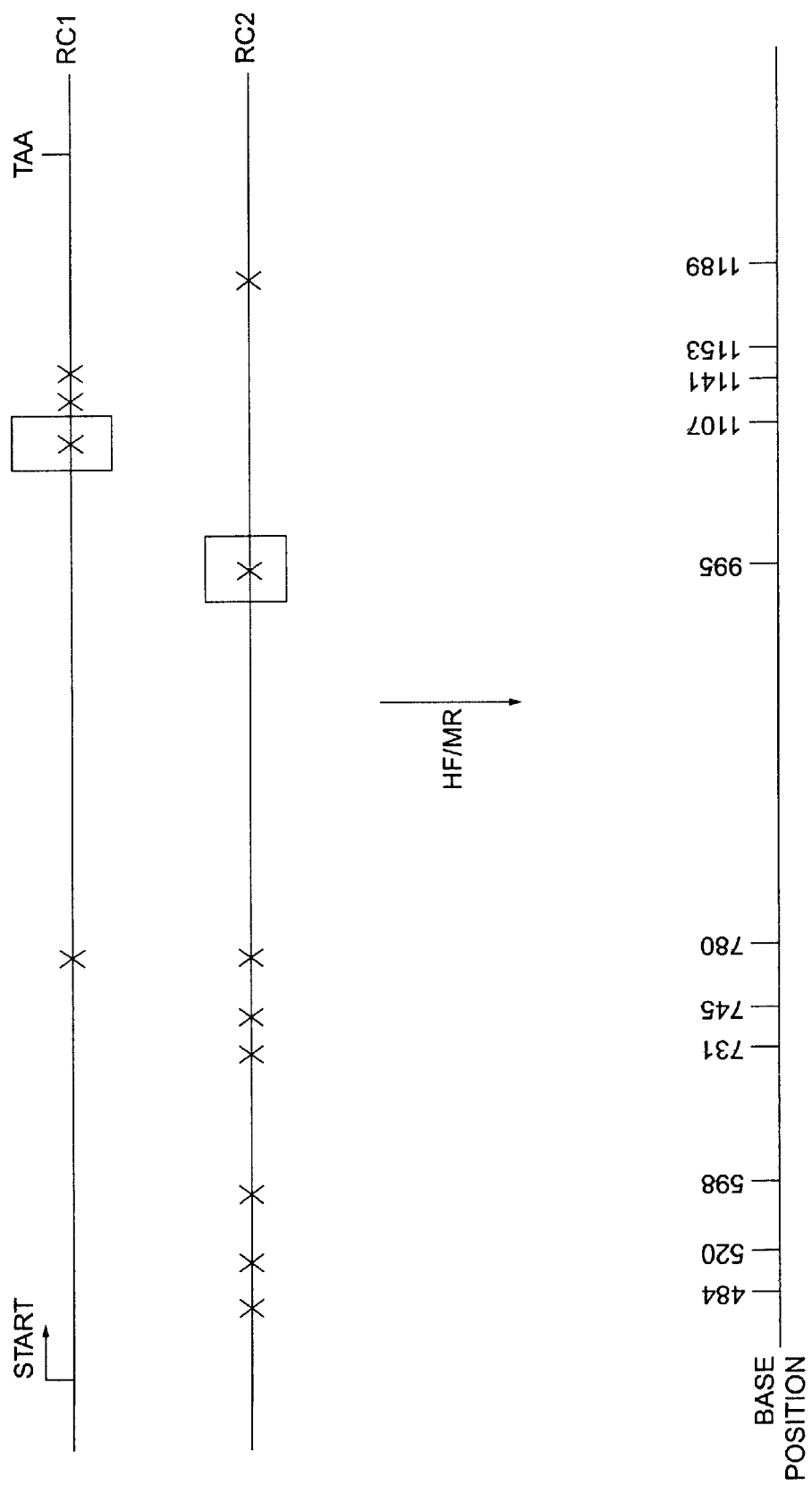
FIG. 15 illustrates the sequences of RC1 and RC2 and the ten clones picked randomly from the transformants of the reaction products of duplex formation as described in Example 3. The x's correspond to base positions that differ between RC1 and RC2. The mutation at 995 corresponds to amino acid substitution at 181, while that at 1107 corresponds to an amino acid substitution at 218 in the subtilisin protein sequence.

Genes RC1 and RC2 encode thermostable *B. sublilis* subtilisin E variants (88). The mutations at base positions 1107 in RC1 and 995 in RC2 (FIG. 14), giving rise to amino acid substitutions Asn218/Ser (N218S) and Asn181/Asp (N181 ID), lead to improvements in subtilisin E thermostability; the remaining mutations, both synonymous and nonsynonymous, have no detectable effects on thermostability. At 65° C., the single variants N181D and N218S have approximately 3-fold and 2-fold longer half-lives, respectively, than wild subtilisin E, and variants containing both mutations have half-lives that are 8-fold longer (88). The different half-lives in a population of subtilisin E variants can therefore be used to estimate the efficiency by which sequence information is combined. In particular, recombination between these two mutations (in the absence of point mutations affecting thermostability) should generate a library in which 25% of the population exhibits the thermos/ability of the double mutant. Similarly, 25% of the population should exhibit wild-type like stability, as N181D and N218S are eliminated at equal frequency. We used the fractions of the recombined population as a diagnostic A. Methods The strategy underlying this example is shown in FIG. 15.

Subtilisin E thermostable mutant genes RC1 and RC2 (FIG. 14) are 986-bp fragments including 45 nt of subtilisin E prosequence, the entire mature sequence and 113 nt after the stop codon. The genes were cloned between Bam HI and Nde I in *E. coli*/*B. subtilis* shuttle vector pBE3, resulting in pBE3-1 and pBE3-2, respectively. Plasmid DNA pBE3-1 and pBE3-2 was isolated from *E.coli* SCS110.

About 5.0 µg of ummethylated pBE3-1 and pBE3-2 DNA were digested with Bam HI and Nde I, respectively, at 37° C. for 1 hour. After agarose gel separation, equimolar concentrations (2.0 nM) of the linearized unmethylated pBE3-1 and pBE3-2 were mixed in 1×SSPE buffer (180 mM NaCl, 1.0 mM EDTA, 10 mM NaH$_2$PO$_4$, pH 7.4). After heating at 96° C. for 10 minutes, the reaction mixture was immediately cooled at 0° C. for 5 min. The mixture was incubated at 68° C. for 2 hr for heteroduplexes to form.

One microliter of the reaction mixture was used to transform 50 μl of E. coli ES 1301 mutS, E. coli SCS110 and E. coli HB101 competent cells.

The transformation efficiency with E. coli HB101 competent cells was about ten times higher than that of E. coli SCS110 and 15 times higher than that of E. coli ES1301 mutS. But in all these cases, the transformation efficiencies were 10–250 times lower than that of the transformation with closed, covalent and circular control pUC19 plasmids.

Five clones from E. coli SCS110 mutant library and five from E. coli ES1301 mutS library were randomly chosen, and plasmid DNA was isolated using a QIAprep spin plasmid miniprep kit for further DNA sequencing analysis.

About 2,000 random clones from E. coli HB101 mutant library were pooled and total plasmid DNA was isolated using a QIAGEN-100 column. 0.5–4.0 μg of the isolated plasmid was used to transform Bacillus subtilis DB428 as described previously (88).

About 400 transformants from the Bacillus subtilis DB428 library were subjected to screening. Screening was performed using the assay described previously (88), on succinyl-Ala-Ala-Pro-Phe-p-nitroanilide. B. subtilis DB428 containing the plasmid library were grown on LB plates containing kanamycin (20 μg/ml) plates. After 18 hours at 37° C. single colonies were picked into 96-well plates containing 200 μl SG/kanamycin medium per well. These plates were incubated with shaking at 37° C. for 24 hours to let the cells to grow to saturation. The cells were spun down, and the supernatants were sampled for the thermostability assay.

Two replicates of 96-well assay plates were prepared for each growth plate by transferring 10 μl of supernatant into the replica plates. The subtilisin activities were then measured by adding 100 μl of activity assay solution (0.2 mM succinyl-Ala-Ala-Pro-Phe-p-nitroanilide, 100 mM Tris-HCl, 10 mM CaCl$_2$, pH 8.0, 37° C.). Reaction velocities were measured at 405 nm to over 1.0 min in a ThermoMax microplate reader (Molecular Devices, Sunnyvale Calif.). Activity measured at room temperature was used to calculate the fraction of active clones (clones with activity less than 10% of that of wild type were scored as inactive). Initial activity ($A_i$) was measured after incubating one assay plate at 65° C. for 10 minutes by immediately adding 100 μl of prewarmed (37° C.) assay solution (0.2 mM succinyl-Ala-Ala-Pro-Phe-p-nitroanilide, 100 mM Tris-HCl, pH 8.0, 10 mM CaCl$_2$, pH 8.0) into each well. Residual activity (Ar) was measured after 40 minute incubation.

B. Results

In vitro heteroduplex formation and in vivo repair was carried out as described above. Five clones from E. coli SCS110 mutant library and five from E. coli ES1301 mutS libraries were selected at random and sequenced. FIG. 14 shows that four out of the ten clones were different from the parent genes. The frequency of occurrence of a particular point mutation from parent RC1 or RC2 in the resulting genes ranged from 0% to 50%, and the ten point mutations in the heteroduplex have been repaired without strong strand-specific preference.

Since none of the ten mutations locates within the dcm site, the mismatch repair appears generally done via the E. coli long-patch mismatch repair systems. The system repairs different mismatches in a strand-specific manner using the state of N6-methylation of adenine in GATC sequences as the major mechanism for determining the strand to be repaired. With heteroduplexes methylated at GATC sequences on only one DNA strand, repair was shown to be highly biased to the unmethylated strand, with the methylated strand serving as the template for correction. If neither strand was methylated, mismatch repair occurred, but showed little strand preference (23, 24). These results shows that it is preferable to demethylate the DNA to be recombined to promote efficient and random repair of the heteroduplexes.

Figure 16:
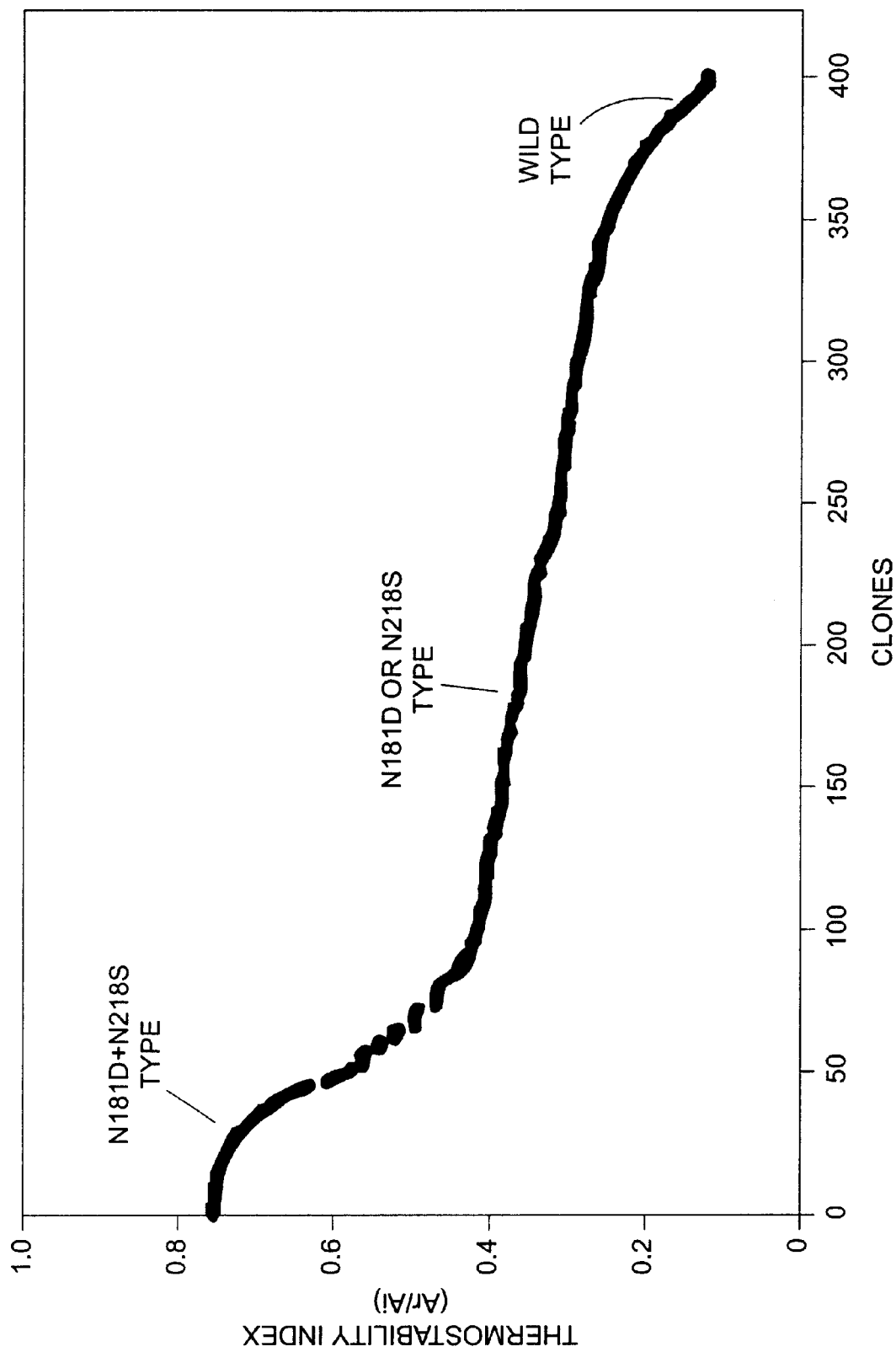
FIG. 16 shows the results of screening 400 clones from the library created by heteroduplex formation and repair for initial activity ($A_i$) and residual activity ($A_r$). The ratio $A_i/A_r$ was used to estimate the enzymes' thermostability. Data from active variants are sorted and plotted in descending order. Approximately 12.9% of the clones exhibit a phenotype corresponding to the double mutant containing both the N181D and the N218S mutations.

The rates of subtilisin E thermo-inactivation at 65° C. were estimated by analyzing the 400 random clones from the Bacillus subtilis DB428 library. The thermostabilities obtained from one 96-well plate are shown in FIG. 16, plotted in descending order. About 12.9% of the clones exhibited thermostability comparable to the mutant with the N181D and N218S double mutations. Since this rate is only half of that expected for random recombination of these two markers, it indicates that the two mismatches at positions 995 and 1107 within the heteroduplexes have been repaired with lower position randomness.

Sequence analysis of the clone exhibiting the highest thermostability among the screened 400 transformants from the E. coli SCS110 heteroduplex library confirmed the presence of both N181D and N218S mutations. Among the 400 transformants from the B.sublilis DB428 library that were screened, approximately 91% of the clones expressed N18ID- and/or N218S-type enzyme stabilities, while about 8.0% of the transformants showed only wild-type subtilisin E stability.

Less than 1.0% inactive clone was found, indicating that few new point mutations were introduced in the recombination process. This is consistent with the fact that no new point mutations were identified in the ten sequenced genes (FIG. 14). While point mutations may provide useful diversity for some in vitro evolution applications, they can also be problematic for recombination of beneficial mutations, especially when the mutation rate is high.

Example 4

Optimizing Conditions for the Heteroduplex Recombination.

We have found that the efficiency of heteroduplex recombination can differ considerably from gene to gene [17,57]. In this example, we investigate and optimize a variety of parameters that improve recombination efficiency. DNA substrates used in this example were site-directed mutants of green fluorescent protein from Aequorea victoria. The GFP mutants had a stop codon(s) introduced at different locations along the sequence that abolished their fluorescence. Fluorescent wild type protein could be only restored by recombination between two or more mutations. Fraction of fluorescent colonies was used as a measure of recombination efficiency.

A. Methods

About 2–4 μg of each parent plasmid was used in one recombination experiment. One parent plasmid was digested with Pst I endonuclease another parent with EcoRI. Linearized plasmids were mixed together and 20×SSPE buffer was added to the final concentration 1×(180 mM NaCl, 1 mM EDTA, 10 mM NaH$_2$PO$_4$, pH 7.4). The reaction mixture was heated at 96° C. for 4 minutes, immediately transferred on ice for 4 minutes and the incubation was continued for 2 hours at 68° C.

Target genes were amplified in a PCR reaction with primers corresponding to the vector sequence of pGFP plasmid. Forward primer: 5'-CCGACTGGAAAGC GGGCAGTG-3', reverse primer 5'-CGGGGCTGGCTT AACTATGCGG-3'. PCR products were mixed together and purified using Qiagen PCR purification kit. Purified products were mixed with 20×SSPE buffer and hybridized as described above. Annealed products were precipitated with ethanol or purified on Qiagen columns and digested with EcoRI and PstI enzymes. Digested products were ligated into PstI and EcoRI digested pGFP vector.

dUTP was added into PCR reaction at final concentrations 200 μM, 40 μM, 8 μM, 1.6 μM, 0.32 μM. PCR reaction and subsequent cloning procedures were performed as described above.

Recombinant plasmids were transformed into XL10 *E. coli* strain by a modified chemical transformation method. Cells were plated on ampicillin containing LB agar plates and grown overnight at 37° C., followed by incubation at room temperature or at 4° C. until fluorescence developed.

B. Results.

1. Effect of Ligation on Recombination Efficiency.

Two experiments have been performed to test the effect of breaks in the DNA heteroduplex on the efficiency of recombination. In one experiment heteroduplex plasmid was treated with DNA ligase to close all existing single-strand breaks and was transformed in identical conditions as an unligated sample (see Table 1). The ligated samples show up to 7-fold improvement in recombination efficiency over unligated samples.

In another experiment, dUTP was added into PCR reaction to introduce additional breaks into DNA upon repair by uracyl N-glycosylase in the host cells. Table 2 shows that dUMP incorporation significantly suppressed recombination, the extent of suppression increasing with increased dUTP concentration.

2. Effect of Plasmid Size on the Efficiency of Heteroduplex Formation.

Plasmid size was a significant factor affecting recombination efficiency. Two plasmids pGFP (3.3 kb) and a *Bacillus* shuttle vector pCT1 (about 9 kb) were used in preparing circular heteroduplex-like plasmids following traditional heteroduplex protocol. For the purpose of this experiment (to study the effect of plasmid size on duplex formation), both parents had the same sequences. While pGFP formed about 30–40% of circular plasmid, the shuttle vector yielded less than 10% of this form.

Increase in plasmid size decreases concentration of the ends in the vicinity of each and makes annealing of very long (>0.8 kb) ends that are single-stranded more difficult. This difficulty is avoided by the procedure shown in FIG. 3, in which heteroduplex formation occurs between substrates in vector-free form, and, heteroduplexes are subsequently inserted into a vector.

3. Efficiency of Recombination vs. Distance Between Mutations

A series of GFP variants was recombined pairwise to study the effect of distance between mutations on the efficiency of recombination. Parental genes were amplified by PCR, annealed and ligated back into pGFP vector. Heteroduplexes were transformed into XL10 *E. coli* strain.

The first three columns in Table 3 show the results of three independent experiments and demonstrate the dependence of recombination efficiency on the distance between mutations. As expected recombination becomes less and less efficient for very close mutations.

However, it is still remarkable that long-patch repair has been able to recombine mutations separated by only 27 bp.

The last line in Table 3 represents recombination between one single and one double mutants. Wild type GFP could only be restored in the event of double crossover with each individual crossover occurring in the distance of 99 bp only, demonstrating the ability of this method to recombine multiple, closely-spaced mutations.

4. Elimination of the Parental Double Strands From Heteroduplex Preparations.

Annealing of substrates in vector-free form offers size-advantages relative to annealing of substrates as components of vectors, but does not allow selection for heteroduplexes relative to homoduplexes simply by transformation into host. Asymmetric PCR reactions with only one primer for each parent seeded with appropriate amount of previously amplified and purified gene fragment were run for 100 cycles, ensuring a 100-fold excess of one strand over another. Products of these asymmetrical reactions were mixed and annealed together producing only a minor amount of nonrecombinant duplexes. The last column in Table 3 shows the recombination efficiency obtained from these enriched heteroduplexes. Comparison of the first three columns with the fourth one demonstrates the improvement achieved by asymmetric synthesis of the parental strands.

While the foregoing invention has been described in some detail for purposes of clarity and understanding, it will be clear to one skilled in the art from a reading of this disclosure that various changes in form and detail can be made without departing from the true scope of the invention. All publications and patent documents cited in this application are incorporated by reference in their entirety for all purposes to the same extent as if each individual publication or patent document were so individually denoted.

REFERENCES

1. Shao, Z. and Arnold, F. H. 1996. Engineering new functions and altering existing functions. Curr. Opin. Struct. Biol. 6:513–518.

2. Kuchner, O and Arnold, F. H. 1997. Directed evolution of enzyme catalysts. Trends in Biotechnol. 15:523–530.

3. Abelson, J. N. (ed.) 1996. Combinatorial chemistry. Methods in Enzymol. 267, Academic Press, Inc. San Diego.

4. Joyce, G. F. 1992. Directed molecular evolution. Scientific American 267:90–97.

5. Stemmer, W. P. C. 1994a. Rapid evolution of a protein in vitro by DNA shuffling. Nature 370:389–391.

6. Stemmer, W. P. C. 1994b. DNA shuffling by random fragmentation and reassembly: in vitro recombination for molecular evolution. Proc. Nati. Acad. Sci. USA 91:10747–10751.

7. Moore, J. C. and Arnold, F. H. 1996. Directed evolution of a para-nitrobenzyl esterase for aqueous-organic solvents. Nature Biotech. 14:458–467.

8. Holland, J. H. 1975. Adaptation in natural and artificial systems. The University Press, Ann Arbor.

9. Goldberg, D. E. 1989. Genetic algorithms in search, optimization and machine learning. Addison-Wesley. Reading.

10. Eigen, M. 1971. Self-organization of matter and the evolution of biological macromolecules. Naturwissenschaften 58:465–523.

11. Rechenberg, L. 1973. Evolutions strategie: Optimierung technischer Systeme nach Prinzipien der biologischen Evolution. Fronimann-Holzboog, Stuttgart.

12. Brady, R. M. 1985. Optimization strategies gleaned from biological evolution. Nature 317:804–806.

13. Muhlenbein, H. 1991. The parallel genetic algorithm as function optimizer. Parallel Computing 17:619–632.

14. Pal, K. F. 1993. Genetic algorithms for the traveling salesman problem-based on a heuristic crossover operation. Bio. Cybem. 69:539–546.

15. Pal, K. F. 1995. Genetic algorithm with local optimization. Bio.Cybem. 73:335–341.

16. Cami, B., P. Chambon, P. Kourilsky. 1984. Correction of complex heteroduplexes made of mouse H-2 gene sequences in *E. coli* K-12. Proc. Natl. Acad. Sci. USA 81:503–507.

17. Westmoreland, J, G. Porter, M. Radman and M. A. Resnick. 1997. Highly mismatched molecules resembling recombination intermediates efficiently transform mismatch repair proficient *E. coli*. Genetics 145:29–38.

18. Kramer, B., W. Kramer and H.-J. Fritz. 1984. Different base/base mismatches are corrected with different efficiencies by the methyl-directed DNA mismatch-repair system of *E. coli*. Cell 38:879–887.

19. Lu, A.-L., S. Clark and P. Modrich. 1983. Methyl-affected repair of DNA base pair mismatches in vitro. Proc. Natl. Acad. Sci. USA 80:4639–4643.

20. Carraway, M. and Marinus, M. G. 1993. Repair of heteroduplex DNA molecules with multibase loops in *Escherichia coli*. J Bacteriol. 175:3972–3980.

21. Cooper, D. L., Lahue, R. S. and Modrich, P. 1993. Methyl-directed mismatch repair is bidirectional. J. Biol. Chem. 268:11823–11829.

22. Au, K. G., Welsh, K. and Modrich, P. 1992. Initiation of methyl-directed mismatch repair. J. Biol. Chem. 267:12142–12148.

23. Meselson, M. 1988. Methyl-directed repair of DNA mismatches, p. 91–113. In K. B. Low (ed.), Recombination of the Genetic Material. Academic Press, Inc., San Diego, Calif.

24. Fishel, R. A., Siegel, E. C. and Kolodner, R. 1986. Gene conversion in *Escherichia coli*. Resolution of heteroallelic mismatched nucleotides by co-repair. J. Mol. Biol. 188:147–157.

25. Pukkila, P. J., J. Peterson, G. Herman, P. Modrich, and M. Meselson. 1983. Effects of high levels of DNA adenine methylation on methyl-directed mismatch repair in *Escherichia coli*. Genetics 104:571–582.

26. Radman, M., R. E. Wagner, B. W. Glickman, and M. Meselson. 1980. DNA methylation, mismatch correction and genetic stability, p. 121–130. In M. Alacevic (ed.) Process in Environmental Mutagenesis. Elsevier/North-Holland Biochemical Press, Amsterdam.

27. Sambrook, J., Fritsch, E. F. and Maniatis, T. 1989. Molecular cloning: A Laboratory Manual. 2nd ed. Cold Spring Harbor Laboratory Press, Cold Spring Harbor, N.Y.

28. Allen, D. J., Makhov, A., Grilley, M.,.Taylor, J., Thresher, R., Modrich, P. and Griffith, J. D. MutS mediates heteroduplex loop formation by a translocation mechanism. 1997. EMBO J. 16: 4467–4476.

30. Tsai-Wu, J. J. and Lu, A. L. 1994. *Escherichia coli* mutY-dependent mismatch repair involves DNA polymerase I and a short repair tract. Mol. Gen. Genet. 244:444–450.

31. Worth, L. Jr., Clark, S., Radman, M. and Modrich, P. 1994. Mismatch repair proteins MutS and MutL inhibit RecA-catalyzed strand transfer between diverged DNAs. Proc. Nati. Acad. Sci. USA 91:3238–3241.

32. Fox, M. S., Radicella, J. P. and Yamamoto, K. 1994. Some features of base pair mismatch repair and its role in the formation of genetic recombinants. Experientia 50:253–260.

33. Radicella, J. P., Clark, E. A., Chen, S. and Fox, M. S. 1993. Patch length of localized repair events: role of DNA polymerase I in mutY-dependent mismatch repair. J. Bacteriol. 175: 7732–7736.

34. Kraczkiewicz-Dowjat, A. and Fishel, R. 1990. RecB-recC-dependent processing of heteroduplex DNA stimulates recombination of an adjacent gene in *Escherichia coli*. J. Bacteriol. 172:172–178.

35. Radman, M. 1989. Mismatch repair and the fidelity of genetic recombination. Genome 31: 68–73.

36. Raposa, S. and Fox, M. S. 1987. Some features of base pair mismatch and heterology repair in *Escherichia coli*. Genetics 117:381–390.

37. Jones, M., Wagner, R. and Radman, M. 1987. Mismatch repair and recombination in *E. coli*. Cell 50:621–626.

38. Langle-Rouault, F., Maenhaut-Michel, G. and Radman, M. 1987. GATC sequences, DNA nicks and the MutH function in *Escherichia coli* mismatch repair. EMBO J. 6:1121–1127

39. Glazer, P. M., Sarkar, S. N., Chisholm, G. E. and Summers, W. C. 1987. DNA mismatch repair detected in human cell extracts. Mol. Cell. Biol. 7:218–224

40. Laengle-Rouault, F., Maenhaut-Michel, G. and Radman M. 1986. GATC sequence and mismatch repair in *Escherichia coli*. EMBO J. 5:2009–2013.

41. Bauer, J., Krammer, G. and Knippers, R. 1981. Asymmetric repair of bacteriophage T7 heteroduplex DNA. Mol. Gen. Genet. 181:541–547.

42. Wildenberg, J. and Meselson, M. 1975. Mismatch repair in heteroduplex DNA. Proc. Natl. Acad. Sci. USA 72:2202–2206.

43. Kirkpatrick, D. T. and Petes, T. D. 1997. Repair of DNA loops involves DNA-mismatch and nucleotide-excision repair proteins. Nature 387: 929–31.

44. Leung, W., Malkova, A. and Haber, J. E. 1997. Gene targeting by linear duplex DNA frequently occurs by assimilation of a single strand that is subject to preferential mismatch correction. Proc. Natl. Acad. Sci. USA 94: 6851–6856.

45. Hunter, N. and Borts, R. H. 1997. Mlh1 is unique among mismatch repair proteins in its ability to promote crossing-over during meiosis. Genes Dev. 11:0890–9369.

46. Alani, E., Lee, S., Kane, M. F., Griffith, J. and Kolodner, R. D. 1997. *Saccharomyces cerevisiae* MSH2, a mispaired base recognition protein, also recognizes Holliday junctions in DNA. J. Mol. Biol. 265:289–301.

47. Varlet, I., Canard, B., Brooks, P., Cerovic, G. and Radman, M. 1996. Mismatch repair in *Xenopus* egg extracts: DNA strand breaks act as signals rather than excision points. Proc. Natl. Acad. Sci. USA 93:10156–10161.

48. Nicolas, A. and Petes, T. D. 1994. Polarity of meiotic gene conversion in fungi: contrasting views. Experientia 50:242–52.

49. Bishop, D. K., J. Andersen, and R. D. Kolodner. 1989. Specificity of mismatch repair following transformation of *Saccharomyces cerevisiae* with heteroduplex plasmid DNA. Proc. Natl. Acad. Sci. USA 86:3713–3717.

50. Kramer, B., W. Kramer, M. S. Williamson, and S. Fogel. 1989. Heteroduplex DNA correction in *Saccharomyces cerevisiae* is mismatch specific and requires functional PMS genes Mol. Cell. Biol. 9:4432–4440.

51. Baynton, K., Bresson-Roy, A. and Fuchs, R. P. 1998. Analysis of damage tolerance pathways in *Saccharomyces cerevisiae*: a requirement for Rev3 DNA polymerase in translation synthesis. Mol. Cell. Biol. 18: 960–966.

52. Alani, E., Reenan, R. A. and Kolodner, R. D. 1994. Interaction between mismatch repair and genetic recombination in *Saccharomyces cerevisiae*. Genetics 137:19–39.

54. Bishop, D. K., Williamson, M. S., Fogel, S. and Kolodner, R. D. 1987.The role of heteroduplex correction in gene conversion in *Saccharomyces cerevisiae*. Nature 328:362–364.

55. Bishop, D. K. and Kolodner, R. D. 1986. Repair of heteroduplex plasmid DNA after transformation into *Saccharomyces cerevisiae*. Mol. Cell Biol. 6:3401–3409.

56. White, J. H., Lusnak, K. and Fogel, S. 1985. Mismatch-specific post-meiotic segregation frequency in yeast suggests a heteroduplex recombination intermediate. Nature 315: 350–352.

57. Abastado, J.-P., B. Cami, T. H. Dinh, J. Igoler and P. Kourilsky. 1984. Processing of complex heteroduplexes in *E. coli* and Cos-1 monkey cells. Proc. Natl. Acad. Sci. USA 81:5792–5796.

58. Brown, T. C. and J. Jiricny. 1987. A specific mismatch repair event protects mammalian cells from loss of 5-methylcytosine. Cell 50:945–950.

59. Sibghat-Ullah, and R-S, Day. 1993. DNA-substrate sequence specificity of human G:T mismatch repair activity. Nucleic Acids Res. 21:1281–1287.

60. Miller, E. M., Hough, H. L., Cho, J. W. and Nickoloff, J. A. 1997. Mismatch repair by efficient nick-directed, and less efficient mismatch-specific, mechanisms in homologous recombination intermediates in Chinese hamster ovary cells. Genetics 147: 743–753.

61. Deng, W. P. and Nickoloff, J. A. 1994. Mismatch repair of heteroduplex DNA intermediates of extrachromosomal recombination in mammalian cells. Mol. Cell Biol. 14:400–406.

62. Thomas, D. C., Roberts, J. D. and Kunkel, T. A. 1991. Heteroduplex repair in extracts of human HeLa cells. J. Biol. Chem. 266:3744–51.

63. Folger, K. R., Thomas, K. and Capecchi, M. R. 1985. Efficient correction of mismatched bases in plasmid heteroduplexes injected into cultured mammalian cell nuclei. Mol. Cell. Biol. 5:70–74.

64. Fang, W., Wu, J. Y. and Su, M. J. 1997. Methyl-directed repair of mismatched small heterologous sequences in cell extracts from *Escherichia coli*. J. Biol. Chem. 272: 22714–22720.

65. Smith, J. and Modrich, P. 1997. Removal of polymerase-produced mutant sequences from PCR products. Proc. Natl. Acad. Sci. U S A 94: 6847–50.

66. Su, S. S., Grilley, M., Thresher, R., Griffith, J. and Modrich, P. 1989. Gap formation is associated with methyl-directed mismatch correction under conditions of restricted DNA synthesis. Genome 31:104–11.

67. Muster-Nassal, C. and Kolodner, R. 1986. Mismatch correction catalyzed by cell-free extracts of *Saccharomyces cerevisiae*. Proc. Natl. Acad. Sci. USA 83:7618–7622.

68. Macnab, R. M. 1992. Genetic and biogenesis of bacterial flagella. Annul Rev. Genet. 26:131–158.

69. Wilson, D. R. and Beveridge, T. J. 1993. Bacterial flagellar filaments and their component flagellins. Can. J. Microbiol. 39:451–472.

70. Schmitt, R., Raskal, A. and Mayer, F. 1974. Plain and complex flagella of *Pseudomonas rhodos*: analysis of fine structure and composition. J. Bacteriol. 117:844–857.

71. Gotz, R., Limmer, N., Ober, K. and Schmitt, R. 1982. Motility and chemotaxis in two strains of *Rhizobium* with complex flagella. J. Gen. Microbiol. 128:789–798.

72. Schmitt, R., Bamberger1., Acker G. and Mayer, F. 1974. Fine structure analysis of the complex flagella of *Rhizobium lupini* H13-3. Arch. Microbiol. 100:145–162.

73. Trachtenberg, S., DeRosier, D. J. and Macnab, R. M. 1987. Three-dimensional structure of the complex flagellar filament of *Rhizobium lupini* and its relation to the structure of the plain filaments. J. Mol. Biol. 195:603–620, 74. Gotz, R. and Schmitt, R. 1987. *Rhizobium meliloti* swims by unidirectional intennittent rotation of right-handed flagellar helices. J. Bacteriol. 169:3146–3150.

75. Lotz, W., Acker, G. and Schmitt, R. 1977. Bacteriophage 7-7-1 adsorbs to the complex flagella of *Rhizobium lupini* H13-3. J. Gen. Virol. 34:9–17.

76. Krupski, G.,Gotz, F., Ober, K., Pleicr, E. and Schmitt, R. 1985. Structure of complex flagellar filaments in *Rhizobium meliloti*. J. Bacteriol. 162:361–366.

77. Maruyama, M., Lodderstaedt, G. and Schmitt, R. 1978. Purification and, biochemical 15 properties of complex flagella isolated from *Rhizobium lupini* H13-3. Biochem. Biophys. Acta 535:110–124.

78. Trachtenberg, S., DeRosier, D. J., Aizawa, S.-I. and Macnab, R. M. 1986. Pairwise perturbation of flagellin subunits. The structural basis for the differences between plain and complex bacterial flagellar filaments. J. Mol. Biol. 190:569–576.

79. Gordee, R. S., Zeckner, D. J., Ellis, L. F., Thakkar, A. L. and Howard, L. C. 1984. In vitro and in vivo anti-Candida activity and toxicity of LY121019. J. Antibiotics 37:1054–1065.

80. Debono, M., Willard, K. E., Kirst, H. A., Wind, J. A., Crouse, G. D., Tao, E. V., Vicenzi, J. T., Counter, F. T., Ott, J. L., Ose, E. E. and Omura, S. 1989. Synthesis of new analogs of echinocandin B by enzymatic deacylation and chemical reacylation of the echinocandin B peptide: synthesis of the antifungal agent cilofungin (LY121019). J. Antibiotics 42(3): 389–397.

81. Debono, M. and Gordee, R. S. 1994. Antibiotics that inhibit fungal cell-wall development. Annu. Rev. Microbiol. 48: 471–497.

82. Debono, M., Turner, W. W., Lagrandeur, L., Burkhardt, F. J., Nissen, J. S., Nichols, K. K., Rodriguez, M. J., Zweifel, M. J., Zeckner, D. J., Gordee, R. S., Tang. J. and Parr, T. R. 1995. Semisynthetic chemical modification of the antifungal lipopeptide echinocandin B (ECB): structure-activity studies of the lipophilic and geometric parameters of polyarylated acyl analogs of ECB. J. Med. Chem. 38(17): 3271–3281.

83. Yeh, W. K. 1997. Evolving enzyme technology for pharmaceutical applications: case studies. J. Ind. Microbiol. Biotechnol. 19(5–6): 334–343.

84. Boeck, L. D., Fukuda, D., Abbott, B. J. and M. Debono. 1989. Deacylation of echinocandin B by *Actinoplanes utahensis*. J. Antibiotics 42(3): 382–388

85. Arnold, F. H. 1998. Design by directed evolution. Accts. Chem. Res. 31:125–131.

86. Shao, Z., Callahan, M. and Arnold, F. H. 1998. Directed enzyme evolution of *Actinoplane utahensis* ECB deacylase in *Streptomyces lividans* for enhanced specific activity. Manuscript submitted.

87. Shao, Z., Zhao, H., Giver, L. and Arnold, F. H. 1998. Random-priming in vitro recombination: an effective tool for directed evolution. Nucleic Acids Res. 26 (2): 681–683.

88. Zhao, H. and Arnold, FH, 1997. Functional and nonfunctional mutations distinguished by random recombination of homologous genes. Proc. Natl. Acad. Sci. USA 94:7997–8000.

89. Zhao, H., Giver, L., Shao, Z., Affholter, J. A., and Arnold, F. H. 1998. Molecular evolution by staggered extension process (StEP) in vitro recombination. Nat. Biotechnol. 16: 258–261.

90. Judo, M. S. B., Wedel, A. B. and Wilson, C. 1998. Stimulation and suppression of PCR-mediated recombination. Nucleic Acids Res. 26: 1819–1825.

91. Okkels, J. S. 1997. Method for preparing polypeptide variants. PCT application WO 97/07205.

92. Gray, G. L. 1992. Hybrid prokaryotic polypeptides produced by in vivo homologous recombination. U.S. Pat. No. 5,093,257.

93. Weber, H. and Weissmann, C. 1983. Formation of genes coding for hybrid proteins by recombination between related, cloned genes in E. coli. Nucl. Acids Res. 11:5661–5669.

94. Maryon, E. and Carroll, D. 1991. Characterization of recombination intermediates from DNA injected into Xenopus laevis oocytes: evidence for a nonconservative mechanism of homologous recombination. Mol. Cell. Biol. 11:3278–3287.

What is claimed is:

1. A method for evolving a polynucleotide toward acquisition of a desired functional property, comprising
   (a) incubating a population of parental polynucleotide variants having sufficient diversity that recombination between the parental polynucleotide variants can generate more recombinated-polynucleotides than there are parental polynucleotide variants under conditions to generate annealed polynucleotides comprising heteroduplexes;
   (b) exposing the heteroduplexes to one or more enzymes of a DNA repair system in vitro to convert the heteroduplexes to parental polynucleotide variants or recombined polynucleotide variants;
   (c) screening or selecting the recombined polynucleotide variants for the desired functional property.

2. The method of claim 1, wherein the DNA repair system comprises cellular extracts.

3. The method of claim 1, wherein the cells are bacterial cells.

4. The method of claim 1 further comprising introducing the products of step (b) into cells.

5. The method of claim 4, wherein the introducing step selects for transformed cells receiving recombinant polynucleotides resulting from resolution of heteroduplexes in step (b) relative to transformed cells receiving polynucleotides resulting from resolution of homoduplexes in step (b).

6. A method for evolving a polynucleotide toward acquisition of a desired functional property, comprising
   (a) incubating a population of parental polynucleotide variants having sufficient diversity that recombination between the parental polynucleotide variants can generate more recombined polynucleotides than there are parental polynucleotide variants under conditions to generate annealed polynucleotides comprising heteroduplexes;
   (b) introducing the annealed polynucleotides into cells having a DNA repair system and propagating the cells under conditions to select for cells receiving heteroduplexes relative to cells receiving homoduplexes, and to convert the heteroduplexes to parental polynucleotide variants or recombined polynucleotide variants;
   (c) screening or selecting the recombined polynucleotide variants for the desired functional property.

7. The method of claim 6, wherein the heteroduplexes are exposed to the cellular DNA repair system in vitro.

8. A method for evolving a polynucleotide toward acquisition of a desired functional property, comprising
   (a) incubating first and second pools of parental polynucleotide variants having sufficient diversity that recombination between the parental polynucleotide variants can generate more recombined polynucleotides than there are parental polynucleotide variants under conditions whereby a strand from any polynucleotide variant in the first pool can anneal with a strand from any polynucleotide in the second pool to generate annealed polynucleotides comprising heteroduplexes;
   (b) exposing the heteroduplexes to a DNA repair system to convert the heteroduplexes to parental polynucleotide variants or recombined polynucleotide variants;
   (c) screening or selecting the recombined polynucleotide variants for the desired functional property.

9. The method of claim 8, further comprising introducing the heteroduplexes into cells, whereby the heteroduplexes are exposed to the DNA repair system of the cells in vivo.

10. The method of claim 9, wherein the annealed polynucleotides further comprise homoduplexes and the introducing step selects for transformed cells receiving heteroduplexes relative to transformed cells receiving homoduplexes.

11. The method of claim 10, 6, or 5, wherein a first polynucleotide variant is provided as a component of a first vector, and a second polynucleotide variant is provided as a component of a second vector, and the method further comprises converting the first and second vectors to linearized forms in which the first and second polynucleotide variants occur at opposite ends, whereby in the incubating step single-stranded forms of the first linearized vector reanneal with each other to form linear first vector, single-stranded forms of the second linearized vector reanneal with each other to form linear second vector, and single-stranded linearized forms of the first and second vectors anneal with each to form a circular heteroduplex bearing a nick in each strand, and the introducing step selects for transformed cells receiving the circular heteroduplexes or recombinant polynucleotides derived therefrom relative to the linear first and second vector.

12. The method of claim 11, wherein the first and second vectors are converted to linearized forms by PCR.

13. The method of claim 11, wherein the first and second vectors are converted to linearized forms by digestion with first and second restriction enzymes.

14. The method of claim 10, 6 or 5, wherein the population of polynucleotides comprises first and second polynucleotides provided in double stranded form, and the method further comprises incorporating the fist and second polynucleotides as components of first and second vectors, whereby the first and second polynucleotides occupy opposite ends of the first and second vectors, whereby in the incubating step single-stranded forms of the first linearized vector reanneal with each other to form linear first vector, single-stranded forms of the second linearized vector reanneal with each other to form linear second vector, and single-stranded linearized forms of the first and second vectors anneal with each to form a circular heteroduplex bearing a nick in each strand, and the introducing step selects for transformed cells receiving the circular heteroduplexes or recombinant polynucleotides derived therefrom relative to the linear first and second vector.

15. The method of claim 10, 6 or 5, further comprising sealing nicks in the heteroduplexes to form covalently-closed circular heteroduplexes before the introducing step.

16. The method of claim 1, 6 or 8, wherein the population of polynucleotide variants are provided in double stranded form, and the method further comprising converting the double stranded polynucleotides to single stranded polynucleotides before the annealing step.

17. The method of claim 1, 6 or 8 wherein the converting step comprises:

conducting asymmetric amplification of the first and second double stranded polynucleotide variants to amplify a first strand of the first polynucleotide variant, and a second strand of the second polynucleotide variant, whereby the first and second strands anneal in the incubating step to form a heteroduplex.

18. The method of claim 17, wherein the first and second double-stranded polynucleotide variants are provided in vector-free form, and the method further comprises incorporating the heteroduplex into a vector.

19. The method of claim 18, wherein the first and second polynucleotides are from chromosomal DNA.

20. The method of claim 1, 6 or 8, further comprising repeating steps (a)–(c) whereby the incubating step in a subsequent cycle is performed on recombinant variants from a previous cycle.

21. The method of claim 1, 6 or 8, wherein the polynucleotide variants encode a polypeptide.

22. The method of claim 1, 6 or 8, wherein the population of polynucleotide variants comprises at least 20 variants.

23. The method of claim 1, 6 or 8, wherein the population of polynucleotide variants are at least 10 kb in length.

24. The method of claim 1, 6 or 8, wherein the population of polynucleotide variants comprises natural variants.

25. The method of claim 1, 6 or 8, wherein the population of polynucleotides comprises variants generated by mutagenic PCR.

26. The method of claim 1, 6 or 8, wherein the population of polynucleotide variants comprises variants generated by site directed mutagenesis.

27. The method of claim 1, 6 or 8, further comprising at least partially demethylating the population of variant polynucleotides.

28. The method of claim 27, whether the at least partially demethylating step is performed by PCR amplification of the population of variant polynucleotides.

29. The method of claim 27, wherein the at least partially demethylating step is performed by amplification of the population of variant polynucleotides in host cells.

30. The method of claim 29, wherein the host cells are defective in a gene encoding a methylase enzyme.

31. The method of claim 27, wherein the population of variant polynucleotides are double stranded polynucleotides and only one strand of each polynucleotide is at least partially demethylated.

32. The method of claim 1, 6 or 8, wherein the population of variant polynucleotide variants comprises at least 5 polynucleotides having at least 90% sequence identity with one another.

33. The method of claim 1, 6 or 8, further comprising isolating a screened recombinant variant.

34. The method of claim 33, further comprising expressing a screened recombinant variant to produce a recombinant protein.

35. The method of claim 34, further comprising formulating the recombinant protein with a carrier to form a pharmaceutical composition.

36. The method of claim 1, 6 or 8, wherein the polynucleotide variants encode enzymes selected from the group consisting of proteases, lipases, amylases, cutinases, cellulases, amylases, oxidases, peroxidases and phytases.

37. The method of claim 1, 6 or 8, wherein the polynucleotide variants encode a polypeptide selected from the group consisting of insulin, ACTH, glucagon, somatostatin, somatotropin, thymosin, parathyroid hormone, pigmentary hormones, somatomedin, erythropoietin, luteinizing hormone, chorionic gonadotropin, hyperthalnic releasing factors, antidiuretic hormones, thyroid stimulating hormone, relaxin, interferon, thrombopoietin (TPO), and prolactin.

38. The method of claim 1, 6 or 8, wherein the polynucleotide variants encode a plurality of enzymes forming a metabolic pathway.

39. The method of claim 1, 6 or 8, wherein the polynucleotide variants are in concatemeric form.

40. The method of claim 39, wherein the functional property is an enzymatic activity.

41. The method of claim 1, 6 or 8, wherein the at least two polynucleotide variants differ at between 0.1–25% of positions.

42. The method of claim 1, 6 or 8, wherein the functional property is an enzymatic activity.

* * * * *

UNITED STATES PATENT AND TRADEMARK OFFICE
CERTIFICATE OF CORRECTION

PATENT NO. : 6,537,746 B2
DATED : March 25, 2003
INVENTOR(S) : Frances Arnold, Zhixin Shao and Alexander Volkov It is certified that error appears in the above-identified patent and that said Letters Patent is hereby corrected as shown below:

<u>Title page,</u>
Item [73], Assignee: should be -- California Institute of Technology --

Signed and Sealed this

Sixteenth Day of September, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,537,746 B2
DATED : March 25, 2003
INVENTOR(S) : Arnold et al.

It is certified that error appears in the above-identified patent and that said Letters Patent is hereby corrected as shown below:

Column 51,
Line 32, replace "recombinated" with -- recombined --.

Column 53,
Line 12, replace "fist" with -- first --.

Signed and Sealed this

Sixth Day of April, 2004

JON W. DUDAS
*Acting Director of the United States Patent and Trademark Office*

SEQUENCE LISTING

<160> NUMBER OF SEQ ID NOS: 11

<210> SEQ ID NO 1
<211> LENGTH: 410
<212> TYPE: PRT
<213> ORGANISM: Rhizobium lupini
<220> FEATURE:
<223> OTHER INFORMATION: flagellin A (FlaA)

<400> SEQUENCE: 1

```
Met Ala Ser Val Leu Thr Asn Ile Asn Ala Met Ser Ala Leu Gln Thr
 1               5                  10                  15

Leu Arg Ser Ile Ser Ser Asn Met Glu Asp Thr Gln Ser Arg Ile Ser
             20                  25                  30

Ser Gly Met Arg Val Gly Ser Ala Ser Asp Asn Ala Ala Tyr Trp Ser
         35                  40                  45

Ile Ala Thr Thr Met Arg Ser Asp Asn Ala Ser Leu Ser Ala Val Gln
     50                  55                  60

Asp Ala Ile Gly Leu Gly Ala Ala Lys Val Asp Thr Ala Ser Ala Gly
 65                  70                  75                  80

Met Asp Ala Val Ile Asp Val Val Lys Gln Ile Lys Asn Lys Leu Val
                 85                  90                  95

Thr Ala Gln Glu Ser Ser Ala Asp Lys Thr Lys Ile Gln Gly Glu Val
            100                 105                 110

Lys Gln Leu Gln Glu Gln Leu Lys Gly Ile Val Asp Ser Ala Ser Phe
        115                 120                 125

Ser Gly Glu Asn Trp Leu Lys Gly Asp Leu Ser Thr Thr Thr Thr Lys
    130                 135                 140

Ser Val Val Gly Ser Phe Val Arg Glu Gly Gly Thr Val Ser Val Lys
145                 150                 155                 160

Thr Ile Asp Tyr Ala Leu Asn Ala Ser Lys Val Leu Val Asp Thr Arg
                165                 170                 175

Ala Thr Gly Thr Lys Thr Gly Ile Leu Asp Thr Ala Tyr Thr Gly Leu
            180                 185                 190

Asn Ala Asn Thr Val Thr Val Asp Ile Asn Lys Gly Gly Val Ile Thr
        195                 200                 205

Gln Ala Ser Val Arg Ala Tyr Ser Thr Asp Glu Met Leu Ser Leu Gly
    210                 215                 220

Ala Lys Val Asp Gly Ala Asn Ser Asn Val Ala Val Gly Gly Gly Ser
225                 230                 235                 240

Ala Ser Ser Arg Ser Thr Ala Ala Gly Leu Arg Val Ala Ser Thr Leu
                245                 250                 255

Arg Pro Pro Ser Pro His Gln His Gln Ser Leu Ala Ser Leu Pro Pro
```

```
                      260                 265                 270
Leu Thr Pro Pro Leu Lys Leu Val Leu Gln Leu Leu Pro Val Thr Pro
            275                 280                 285
Ser Ser Ser Thr Lys Pro Thr Ala Ala Pro Val Gln Val Asn Leu Thr
    290                 295                 300
Gln Ser Val Leu Thr Met Asp Val Ser Met Ser Ser Thr Asp Val
305                 310                 315                 320
Gly Ser Tyr Leu Thr Gly Val Glu Lys Ala Leu Thr Ser Leu Thr Ser
                325                 330                 335
Ala Gly Ala Glu Leu Gly Ser Ile Lys Gln Arg Ile Asp Leu Gln Val
            340                 345                 350
Asp Phe Ala Ser Lys Leu Gly Asp Ala Leu Ala Lys Gly Ile Gly Arg
        355                 360                 365
Leu Val Asp Ala Asp Met Asn Glu Glu Ser Thr Lys Leu Lys Ala Leu
    370                 375                 380
Gln Thr Gln Gln Gln Leu Ala Ile Gln Ser Leu Ser Ile Ala Asn Ser
385                 390                 395                 400
Asp Ser Gln Asn Ile Leu Ser Leu Phe Arg
                405                 410

<210> SEQ ID NO 2
<211> LENGTH: 394
<212> TYPE: PRT
<213> ORGANISM: Rhizobium meliloti
<220> FEATURE:
<223> OTHER INFORMATION: flagellin A (FlaA)

<400> SEQUENCE: 2

Met Thr Ser Ile Leu Thr Asn Asn Ser Ala Met Ala Ala Leu Ser Thr
  1               5                  10                  15
Leu Arg Ser Ile Ser Ser Ser Met Glu Asp Thr Gln Ser Arg Ile Ser
                 20                  25                  30
Ser Gly Leu Arg Val Gly Ser Ala Ser Asp Asn Ala Ala Tyr Trp Ser
             35                  40                  45
Ile Ala Thr Thr Met Arg Ser Asp Asn Gln Ala Leu Ser Ala Val Gln
         50                  55                  60
Asp Ala Leu Gly Leu Gly Ala Ala Lys Val Asp Thr Ala Tyr Ser Gly
 65                  70                  75                  80
Met Glu Ser Ala Ile Glu Val Val Lys Glu Ile Lys Ala Lys Leu Val
                 85                  90                  95
Ala Ala Thr Glu Asp Gly Val Asp Lys Ala Lys Ile Gln Glu Glu Ile
            100                 105                 110
Thr Gln Leu Lys Asp Gln Leu Thr Ser Ile Ala Glu Ala Ala Ser Phe
        115                 120                 125
Ser Gly Glu Asn Trp Leu Gln Ala Asp Leu Ser Gly Gly Pro Val Thr
    130                 135                 140
Lys Ser Val Val Gly Gly Phe Val Arg Asp Ser Ser Gly Ala Val Ser
145                 150                 155                 160
Val Lys Lys Val Asp Tyr Ser Leu Asn Thr Asp Thr Val Leu Phe Asp
                165                 170                 175
Thr Thr Gly Asn Thr Gly Ile Leu Asp Lys Val Tyr Asn Val Ser Gln
            180                 185                 190
Ala Ser Val Thr Leu Pro Val Asn Val Asn Gly Thr Thr Ser Glu Tyr
        195                 200                 205
Thr Val Gly Ala Tyr Asn Val Asp Asp Leu Ile Asp Ala Ser Ala Thr
```

```
            210                 215                 220
Phe Asp Gly Asp Tyr Ala Asn Val Gly Ala Gly Ala Leu Ala Gly Asp
225                 230                 235                 240

Tyr Val Lys Val Gln Gly Ser Trp Val Lys Ala Val Asp Val Ala Ala
                245                 250                 255

Thr Gly Gln Glu Val Val Tyr Asp Asp Gly Thr Thr Lys Trp Gly Val
                260                 265                 270

Asp Thr Thr Val Thr Gly Ala Pro Ala Thr Asn Val Ala Ala Pro Ala
                275                 280                 285

Ser Ile Ala Thr Ile Asp Ile Thr Ile Ala Ala Gln Ala Gly Asn Leu
                290                 295                 300

Asp Ala Leu Ile Ala Gly Val Asp Glu Ala Leu Thr Asp Met Thr Ser
305                 310                 315                 320

Ala Ala Ala Ser Leu Gly Ser Ile Ser Ser Arg Ile Asp Leu Gln Ser
                325                 330                 335

Asp Phe Val Asn Lys Leu Ser Asp Ser Ile Asp Ser Gly Val Gly Arg
                340                 345                 350

Leu Val Asp Ala Asp Met Asn Glu Glu Ser Thr Arg Leu Lys Ala Leu
                355                 360                 365

Gln Thr Gln Gln Gln Leu Ala Ile Gln Ala Leu Ser Ile Ala Asn Ser
370                 375                 380

Asp Ser Gln Asn Val Leu Ser Leu Phe Arg
385                 390

<210> SEQ ID NO 3
<211> LENGTH: 1201
<212> TYPE: DNA
<213> ORGANISM: Artificial Sequence
<220> FEATURE:
<223> OTHER INFORMATION: Description of Artificial Sequence:SCS01 mosaic
      flaA gene created by in vitro heteroduplex
      formation followed by in vivo repair

<400> SEQUENCE: 3
atggcaagcg ttctcacaaa cattaacgca atgtctgctc ttcagacgct gcgttcgatt     60
tcttccaaca tggaagacac ccagagccgt atttccagcg gcatgcgcgt tggttcgget    120 tccgacaacg ccgcttattg gtctatcgcg accaccatgc gctcggacaa tgcctcgctt    180
tccgctgttc aggatgcaat tggcctcggt gccgccaagg tcgataccgc ttcggcgggt    240
atggatgcgg ttatcgatgt tgtaaagcag atcaagaaca aactggtcac tgccaccgaa    300
gacggcgtcg acaaggccaa gatccaagaa gaaatcactc agctcaagga ccagctgacg    360
agcatcgccg acgcggcttc cttctccggt gaaaactggc tcaagggcga tctttccacg    420
acgacaacca aatcagtggt tggctccttc gttcgtgaag gcggtaccgt atcggtcaag    480
accatcgatt acgctctgaa tgcttccaag gttctggtgg atacccgcgc aacgggcacc    540
aagaccggca ttctggacaa ggtctacaac gtctcgcagg caagcgtcac gctgacggtc    600
aacaccaacg gcgtcgaatc ccaggcctcc gtccgcgcct attcgctgga gtccctcacc    660
gaagccggtg cggagttcca gggcaactat gctcttcagg gcggtaacag ctacgtcaag    720
gtcgaaaacg tctgggttcg agctgagacc gcatcaacac cagtcgctgg caagtttgcc    780
gccgcttaca ccgccgctga agctggtact gcagctgctg ccggtgacgc catcatcgtc    840
gacgaaacca cagcggcgc cggtgcaggt aaacctcacc cagtcggtcc tgaccatgga    900
tgtcagctcg atgagctcga cggatgtcgg cagctacctc acgggcgtgg aaaaggctct    960
```

```
caccagcctg acgagcgctg gcgctgaact cggctctatc aaacagcgca tcgatctgca   1020
ggttgatttt gcttccaagc tgggcgacgc tctcgcaaaa ggtattggcc gtctcgttga   1080
tgctgacatg aatgaagagt ccactaagct taaggctctt cagacgcagc agcagctggc   1140
tatccagtcg ctctccatcg caaacagcga ctcgcagaac attctgtcgc tgttccgtta   1200
a                                                                   1201
```

<210> SEQ ID NO 4
<211> LENGTH: 1229
<212> TYPE: DNA
<213> ORGANISM: Artificial Sequence
<220> FEATURE:
<223> OTHER INFORMATION: Description of Artificial Sequence:SCS02 mosaic
      flaA gene created by in vitro heteroduplex
      formation followed by in vivo repair

<400> SEQUENCE: 4

```
atgacgagca ttctcaccaa caactccgca atggccgcgc tttccggagt gcgctcgatc    60
tcttccagca tggaagacac gcagagccgc atctcctccg gccttcgcgt cggttcggcc   120
tccgacaacg ccgcctactg gtcgattgcg accaccatgc gctccgacaa ccaggccctt   180
tcggccgtcc aggacgccct cggcctcggc gccgccaagg ttgataccgc ctattccggt   240
atggaatcgg cgatcgaagt cgttaaggaa atcaagaaca aactggtcac tgctcaggaa   300
tcttctgccg acaaaacgaa gattcagggc gaagtcaagc agcttcagga gcagttgaag   360
ggcatcgttg attccgcttc cttctccggt gagaactggc tgcaggcgga cctcagcggc   420
ggcgccgtca ccaagagcgt cgtcggctcg ttcgtccgtg acggaagcgg ttccgtagcc   480
gtcaagaagg tcgattacgc tctgaatgct tccaaggttc tggtggatac ccgcgcaacg   540
ggcaccaaga ccggcattct cgatactgct tataccggcc ttaacgcgaa cacggtgacg   600
gttgatatca caagggcgg cgtgatcacc caggcctccg tccgcgccta ttccacggac   660
gaaatgctct ccctcggcgc aaaggtcgat ggcgcaaaca gcaacgttgc tgttggcggc   720
ggctccgctt cgtcaaggtc gacggcagct gggttaaggg tagcgtcgac gctgcggcct   780
ccatcaccgc atcaaccggc gccaccggtc aagaaatcgc cgccaccacg acggcagctg   840
gtaccatcac tgcagacagc tgggtcgtcg atgtcggcaa cgctcctgcc gccaacgttt   900
cggccggcca gtcggtcgcg aacatcaaca tcgtcggaat gggctcgacg gatgtcggca   960
gctacctcac gggcgtggaa aagctctcca ccagcatgac cagcgctgcc gcctcgctcg   1020
gctccatctc ctcgcgcatc gacctgcaga gcgaattcgt caacaagctc tcggactcga   1080
tcgagtcggg cgtcggccgt ctcgtcgacg cggacatgaa cgaggagtcg acccgcctca   1140
aggccctgca gacccagcag cagctcgcca tccaggccct gtcgatcgcc aactcggact   1200
cgcagaacgt cctgtcgctc ttccgctaa                                      1229
```

<210> SEQ ID NO 5
<211> LENGTH: 1228
<212> TYPE: DNA
<213> ORGANISM: Artificial Sequence
<220> FEATURE:
<223> OTHER INFORMATION: Description of Artificial Sequence:ES01 mosaic
      flaA gene created by in vitro heteroduplex
      formation followed by in vivo repair

<400> SEQUENCE: 5

```
atgacgagca ttctcaccaa caactccgca atggccgcgc tttccggagt gcgctcgatc    60
tcttccagca tggaagacac gcagagccgc atctcctccg gccttcgcgt cggttcggcc   120
```

```
tccgacaacg ccgcctactg gtcgattgcg accaccatgc gctccgacaa ccaggccctt      180
tcggccgtcc aggacgccct cggcctcggc gccgccaagg ttgataccgc ctattccggt      240
atggaatcgg cgatcgaagt cgttaaggaa atcaaggcca agctcgtagc tgccaccgaa      300
gacggcgtcg acaaggccaa gatccaagaa gaaatcactc agctcaagga ccagctgacg      360
agcatcgccg acgcggcttc cttctccggt gagaactggc tgcaggcgga cctcagcggc      420
ggcgccgtca ccaagagcgt cgtcggctcg ttcgtccgtg acggaagcgg ttccgtagcc      480
gtcaagacca tcgattacgc tctgaatgct tccaaggttc tggtggatac ccgcgacacg      540
gtcggcgata ccggcattct ggacaaggtc tacaacgtct cgcaggcaag cgtcacgctg      600
acggtcaaca ccaacggcgt cgaatcgcag catacggttg ctgcctattc gctggagtcc      660
ctcaccgaag ccggtgcgga gttccagggc aactatgctc ttcagggcgg taacagctac      720
gtcaaggtcg acgcagctg ggttaagggt agcgtcgacg ctgcggcctc catcaccgca      780
tcaacaccag tcgctggcaa gtttgccgcc gcttacaccg ccgctgaagc tggtactgca      840
gctgctgccg gtgacgccat catcgtcgac gaaaccaaca gcggcgccgg tgcaggtaaa      900
cctcacccag tcggtcctga ccatggatgt cagctcgatg agctcgacgg atgtcggcag      960
ctacctcacg ggcgtggaaa aggctctcac cagcctgacg agcgctggcg ctgaactcgg     1020
ctccatctcc tcgcgcatcg acctgcagag cgaattcgtc aacaagctct cggactcgat     1080
cgagtcgggc gtcggccgtc tcgtcgacgc ggacatgaac gaggagtcga cccgcctcaa     1140
ggccctgcag acccagcagc agctcgccat ccaggccctg tcgatcgcca actcggactc     1200
gcagaacgtc ctgtcgctct ccgctaa                                        1228
```

<210> SEQ ID NO 6
<211> LENGTH: 1209
<212> TYPE: DNA
<213> ORGANISM: Artificial Sequence
<220> FEATURE:
<223> OTHER INFORMATION: Description of Artificial Sequence:ES02 mosaic
      flaA gene created by in vitro heteroduplex
      formation followed by in vivo repair

<400> SEQUENCE: 6

```
atgacgagca ttctcaccaa caactccgca atggccgcgc tttccggagt gcgctcgatc       60
tcttccagca tggaagacac gcagagccgc atctcctccg gccttcgcgt cggttcggcc      120
tccgacaacg ccgcctactg gtcgattgcg accaccatgc gctccgacaa ccaggccctt      180
tcggccgtcc aggacgccct cggcctcggc gccgccaagg ttgataccgc ctattccggt      240
atggaatcgg cgatcgaagt cgttaaggaa atcaaggcca agctcgtagc tgccaccgaa      300
gacggcgtcg acaaggccaa gatccaagaa gaaatcactc agctcaagga ccagctgacg      360
agcatcgccg acgcggcttc cttctccggt gagaactggc tgcaggcgga cctcagcggc      420
ggcgccgtca ccaagagcgt cgtcggctcg ttcgtccgtg acggaagcgg ttccgtagcc      480
gtcaagacca tcgattacgc tctgaatgct tccaaggttc tggtggatac ccgcgcaacg      540
ggcaccaaga ccggcattct cgatactgct tataccggcc ttaacgcgaa cacggtgacg      600
gttgatatca caaagggcgg cgtgatcacc caggcctccg tccgcgccta ttccacggac      660
gaaatgctct ccctcaccga agccggtgcg gagttccagg gcaactatgc tcttcagggc      720
ggtaacagct acgtcaaggt cgaaaacgtc tgggttcgag ctgagaccgc tgcaaccggc      780
gccaccggtc aagaaatcgc cgccaccacg acggcagctg gtaccatcac tgcagacagc      840
```

-continued

```
tgggtcgtcg atgtcggcaa cgctcctgcc gccaacgttt cggccggcca gtcggtcgcg      900
aacatcaaca tcgtcggaat gggtgcagct gcgctcgatg ccctgatcag cggtgtcgac      960
gccgctttga cagacatgac cagcgctgcc gcctcgctcg gctccatctc ctcgcgcatc     1020
gacctgcaga gcgaattcgt caacaagctc tcggactcga tcgagtcggg cgtcggccgt     1080
ctcgtcgacg cggacatgaa cgaggagtcg acccgcctca aggccctgca gacccagcag     1140
cagctcgcca tccaggccct gtcgatcgcc aactcggact cgcagaacgt cctgtcgctc     1200
ttccgctaa                                                            1209
```

<210> SEQ ID NO 7
<211> LENGTH: 4039
<212> TYPE: DNA
<213> ORGANISM: Artificial Sequence
<220> FEATURE:
<223> OTHER INFORMATION: Description of Artificial Sequence:Actinoplanes
      utahensis echinocandin B (ECB) deacylase gene
      mutant M-15 created by in vitro heteroduplex
      formation followed by in vivo repair
<221> NAME/KEY: CDS
<222> LOCATION: (1196)..(3559)

<400> SEQUENCE: 7

```
ctgcagcgtg cccagctgtt cgtggtggtg atcgcggccg cgctggccgc cgtcgcggtc       60
gccgccgccg ggccgatcga gttcgtcgcc ttcgtcgtgc cgcagatcgc cctgcggctc      120
tgcggcggca gccggccgcc cctgctcgcc tcggcgatgc tcggcgcgct gctggtggtc      180
ggcgccgacc tggtcgctca gatcgtggtg gcgccgaagg agctgccggt cggcctgctc      240
accgcgatga tcggcacccc gtacctgctc tggctcctgc ttcggcgatc aagaaaggtg      300
agcggatgaa cgcccgcctg cgtggcgagg gcctgcacct cgcgtacggg gacctgaccg      360
tgatcgacgg cctcgacgtc gacgtgcacg acgggctggt caccaccatc atcgggccca      420
acgggtgcgg caagtcgacg ctgctcaagg cgctcggccg gctgctgcgc ccgaccggcg      480
ggcaggtgct gctggacggc cgccgcatcg accggacccc cacccgtgac gtggcccggg      540
tgctcggcgt gctgccgcag tcgcccaccg cgcccgaagg gctcaccgtc gccgacctgg      600
tgatgcgcgg ccggcacccg caccagacct ggttccggca gtggtcgcgc gacgacgagg      660
accaggtcgc cgacgcgctg cgctggaccg acatgctggc gtacgcggac cgcccggtgg      720
acgccctctc cggcggtcag cgccagcgcg cctggatcag catggcgctg gcccagggca      780
ccgacctgct gctgctggac gagccgacca ccttcctcga cctggcccac cagatcgacg      840
tgctggacct ggtccgccgg ctgcacgccg agatgggccg gaccgtggtg atggtgctgc      900
acgacctgag cctggccgcc cggtacgccg accggctgat cgcgatgaag gacggccgga      960
tcgtggcgag cggggcgccg gacgaggtgc tcaccccggc gctgctggag tcggtcttcg     1020
ggctgcgcgc gatggtggtg cccgaccggg cgaccggcac cccgctggtg atccccctgc     1080
cgcgccccgc cacctcggtg cgggcctgaa atcgatgagc gtggttgctt catcggcctg     1140
ccgagcgatg agagtatgtg gcggtagag cgagtctcga gggggagatg ccgcc gtg       1198
                                                                Val
                                                                  1 acg tcc tcg tac atg cgc ctg aaa gca gca gcg atc gcc ttc ggt gtg     1246
Thr Ser Ser Tyr Met Arg Leu Lys Ala Ala Ala Ile Ala Phe Gly Val
           5                  10                  15 atc gtg gcg acc gca gcc gtg ccg tca ccc gct tcc ggc agg gaa cat     1294
Ile Val Ala Thr Ala Ala Val Pro Ser Pro Ala Ser Gly Arg Glu His
 20                  25                  30
```

-continued

```
gac ggc ggc tat gcg gcc ctg atc cgc cgg gcc tcg tac ggc gtc ccg      1342
Asp Gly Gly Tyr Ala Ala Leu Ile Arg Arg Ala Ser Tyr Gly Val Pro
 35                  40                  45 cac atc acc gcc gac gac ttc ggg agc ctc ggt ttc ggc gtc ggg tac      1390
His Ile Thr Ala Asp Asp Phe Gly Ser Leu Gly Phe Gly Val Gly Tyr
 50                  55                  60                  65 gtg cag gcc gag gac aac atc tgc gtc atc gcc gag agc gta gtg acg      1438
Val Gln Ala Glu Asp Asn Ile Cys Val Ile Ala Glu Ser Val Val Thr
                 70                  75                  80 gcc aac ggt gag cgg tcg cgg tgg ttc ggt gcg acc ggg ccg gac gac      1486
Ala Asn Gly Glu Arg Ser Arg Trp Phe Gly Ala Thr Gly Pro Asp Asp
             85                  90                  95 gcc gat gtg cgc agc gac ctc ttc cac cgc aag gcg atc gac gac cgc      1534
Ala Asp Val Arg Ser Asp Leu Phe His Arg Lys Ala Ile Asp Asp Arg
        100                 105                 110 gtc gcc gag cgg ctc ctc gaa ggg ccc cgc gac ggc gtg cgg gcg ccg      1582
Val Ala Glu Arg Leu Leu Glu Gly Pro Arg Asp Gly Val Arg Ala Pro
    115                 120                 125 tcg gac gac gtc cgg gac cag atg cgc ggc ttc gtc gcc ggc tac aac      1630
Ser Asp Asp Val Arg Asp Gln Met Arg Gly Phe Val Ala Gly Tyr Asn
130                 135                 140                 145 cac ttc cta cgc cgc acc ggc gtg cac cgc ctg acc gac ccg gcg tgc      1678
His Phe Leu Arg Arg Thr Gly Val His Arg Leu Thr Asp Pro Ala Cys
                150                 155                 160 cgc ggc aag gcc tgg gtg cgc ccg ctc tcc gag atc gat ctc tgg cgt      1726
Arg Gly Lys Ala Trp Val Arg Pro Leu Ser Glu Ile Asp Leu Trp Arg
            165                 170                 175 acg tcg tgg gac agc atg gtc cgg gcc ggt tcc ggg gcg ctg ctc gac      1774
Thr Ser Trp Asp Ser Met Val Arg Ala Gly Ser Gly Ala Leu Leu Asp
        180                 185                 190 ggc atc gtc gcc gcg acg cca cct aca gcc gcc ggg ccc gcg tca gcc      1822
Gly Ile Val Ala Ala Thr Pro Pro Thr Ala Ala Gly Pro Ala Ser Ala
    195                 200                 205 ccg gag gca ccc gac gcc gcc gcg atc gcc gcc gcc ctc gac ggg acg      1870
Pro Glu Ala Pro Asp Ala Ala Ala Ile Ala Ala Ala Leu Asp Gly Thr
210                 215                 220                 225 agc gcg ggc atc ggc agc aac gcg tac ggc ctc ggc gcg cag gcc acc      1918
Ser Ala Gly Ile Gly Ser Asn Ala Tyr Gly Leu Gly Ala Gln Ala Thr
                230                 235                 240 gtg aac ggc agc ggg atg gtg ctg gcc aac ccg cac ttc ccg tgg cag      1966
Val Asn Gly Ser Gly Met Val Leu Ala Asn Pro His Phe Pro Trp Gln
            245                 250                 255 ggc gcc gca cgc ttc tac cgg atg cac ctc aag gtg ccc ggc cgc tac      2014
Gly Ala Ala Arg Phe Tyr Arg Met His Leu Lys Val Pro Gly Arg Tyr
        260                 265                 270 gac gtc gag ggc gcg gcg ctg atc ggc gac ccg atc atc ggg atc ggg      2062
Asp Val Glu Gly Ala Ala Leu Ile Gly Asp Pro Ile Ile Gly Ile Gly
    275                 280                 285 cac aac cgc acg gtc gcc tgg agc cac acc gtc tcc acc gcc cgc cgg      2110
His Asn Arg Thr Val Ala Trp Ser His Thr Val Ser Thr Ala Arg Arg
290                 295                 300                 305 ttc gtg tgg cac cgc ctg agc ctc gtg ccc ggc gac ccc acc tcc tat      2158
Phe Val Trp His Arg Leu Ser Leu Val Pro Gly Asp Pro Thr Ser Tyr
                310                 315                 320 tac gtc gac ggc cgg ccc gag cgg atg cgc gcc cgc acg gtc acg gtc      2206
Tyr Val Asp Gly Arg Pro Glu Arg Met Arg Ala Arg Thr Val Thr Val
            325                 330                 335 cag acc ggc agc ggc ccg gtc agc cgc acc ttc cac gac acc cgc tac      2254
Gln Thr Gly Ser Gly Pro Val Ser Arg Thr Phe His Asp Thr Arg Tyr
        340                 345                 350
```

```
ggc ccg gtg gcc gtg atg ccg ggc acc ttc gac tgg acg ccg gcc acc      2302
Gly Pro Val Ala Val Met Pro Gly Thr Phe Asp Trp Thr Pro Ala Thr
    355                 360                 365 gcg tac gcc atc acc gac gtc aac gcg ggc aac aac cgc gcc ttc gac      2350
Ala Tyr Ala Ile Thr Asp Val Asn Ala Gly Asn Asn Arg Ala Phe Asp
370                 375                 380                 385 ggg tgg ctg cgg atg ggc cag gcc aag gac gtc cgg gcg ctc aag gcg      2398
Gly Trp Leu Arg Met Gly Gln Ala Lys Asp Val Arg Ala Leu Lys Ala
                390                 395                 400 gtc ctc gac cgg cac cag ttc ctg ccc tgg gtc aac gtg atc gcc gcc      2446
Val Leu Asp Arg His Gln Phe Leu Pro Trp Val Asn Val Ile Ala Ala
            405                 410                 415 gac gcg cgg ggc gag gcc ctc tac ggc gat cat tcg gtc gtc ccc cgg      2494
Asp Ala Arg Gly Glu Ala Leu Tyr Gly Asp His Ser Val Val Pro Arg
        420                 425                 430 gtg acc ggc gcg ctc gct gcc gcc tgc atc ccg gcg ccg ttc cag ccg      2542
Val Thr Gly Ala Leu Ala Ala Ala Cys Ile Pro Ala Pro Phe Gln Pro
    435                 440                 445 ctc tac gcc tcc agc ggc cag gcg gtc ctg gac ggt tcc cgg tcg gac      2590
Leu Tyr Ala Ser Ser Gly Gln Ala Val Leu Asp Gly Ser Arg Ser Asp
450                 455                 460                 465 tgc gcg ctc ggc gcc gac ccc gac gcc gcg gtc ccg ggc att ctc ggc      2638
Cys Ala Leu Gly Ala Asp Pro Asp Ala Ala Val Pro Gly Ile Leu Gly
                470                 475                 480 ccg gcg agc ctg ccg gtg cgg ttc cgc gac gac tac gtc acc aac tcc      2686
Pro Ala Ser Leu Pro Val Arg Phe Arg Asp Asp Tyr Val Thr Asn Ser
            485                 490                 495 aac gac agt cac tgg ctg gcc agc ccg gcc gcc ccg ctg gaa ggc ttc      2734
Asn Asp Ser His Trp Leu Ala Ser Pro Ala Ala Pro Leu Glu Gly Phe
        500                 505                 510 ccg cgg atc ctc ggc aac gaa cgc acc ccg cgc agc ctg cgc acc cgg      2782
Pro Arg Ile Leu Gly Asn Glu Arg Thr Pro Arg Ser Leu Arg Thr Arg
    515                 520                 525 ctc ggg ctg gac cag atc cag cag cgc ctc gcc ggc acg gac ggt ctg      2830
Leu Gly Leu Asp Gln Ile Gln Gln Arg Leu Ala Gly Thr Asp Gly Leu
530                 535                 540                 545 ccc ggc aag ggc ttc acc acc gcc cgg ctc tgg cag gtc atg ttc ggc      2878
Pro Gly Lys Gly Phe Thr Thr Ala Arg Leu Trp Gln Val Met Phe Gly
                550                 555                 560 aac cgg atg cac ggc gcc gaa ctc gcc cgc gac gac ctg gtc gcg ctc      2926
Asn Arg Met His Gly Ala Glu Leu Ala Arg Asp Asp Leu Val Ala Leu
            565                 570                 575 tgc cgc cgc cag ccg acc gcg acc gcc tcg aac ggc gcg atc gtc gac      2974
Cys Arg Arg Gln Pro Thr Ala Thr Ala Ser Asn Gly Ala Ile Val Asp
        580                 585                 590 ctc acc gcg gcc tgc acg gcg ctg tcc cgc ttc gat gag cgt gcc gac      3022
Leu Thr Ala Ala Cys Thr Ala Leu Ser Arg Phe Asp Glu Arg Ala Asp
    595                 600                 605 ctg gac agc cgg ggc gcg cac ctg ttc acc gag ttc gcc ctc gcg ggc      3070
Leu Asp Ser Arg Gly Ala His Leu Phe Thr Glu Phe Ala Leu Ala Gly
610                 615                 620                 625 gga atc agg ttc gcc gac acc ttc gag gtg acc gat ccg gta cgc acc      3118
Gly Ile Arg Phe Ala Asp Thr Phe Glu Val Thr Asp Pro Val Arg Thr
                630                 635                 640 ccg cgc cgt ctg aac acc acg gat ccg cgg gta cgg acg gcg ctc gcc      3166
Pro Arg Arg Leu Asn Thr Thr Asp Pro Arg Val Arg Thr Ala Leu Ala
            645                 650                 655 gac gcc gtg caa cgg ctc gcc ggc atc ccc ctc gac gcg aag ctg gga      3214
Asp Ala Val Gln Arg Leu Ala Gly Ile Pro Leu Asp Ala Lys Leu Gly
```

```

660                  665                 670
gac atc cac acc gac agc cgc ggc gaa cgg cgc atc ccc atc cac ggt            3262
Asp Ile His Thr Asp Ser Arg Gly Glu Arg Arg Ile Pro Ile His Gly
        675                 680                 685 ggc cgc ggg gaa gca ggc acc ttc aac gtg atc acc aac ccg ctc gtg            3310
Gly Arg Gly Glu Ala Gly Thr Phe Asn Val Ile Thr Asn Pro Leu Val
690                 695                 700                 705 ccg ggc gtg gga tac ccg cag gtc gtc cac gga aca tcg ttc gtg atg            3358
Pro Gly Val Gly Tyr Pro Gln Val Val His Gly Thr Ser Phe Val Met
                710                 715                 720 gcc gtc gaa ctc ggc ccg cac ggc ccg tcg gga cgg cag atc ctc acc            3406
Ala Val Glu Leu Gly Pro His Gly Pro Ser Gly Arg Gln Ile Leu Thr
            725                 730                 735 tat gcg cag tcg acg aac ccg aac tca ccc tgg tac gcc gac cag acc            3454
Tyr Ala Gln Ser Thr Asn Pro Asn Ser Pro Trp Tyr Ala Asp Gln Thr
        740                 745                 750 gtg ctc tac tcg cgg aag ggc tgg gac acc atc aag tac acc gag gcg            3502
Val Leu Tyr Ser Arg Lys Gly Trp Asp Thr Ile Lys Tyr Thr Glu Ala
755                 760                 765 cag atc gcg gcc gac ccg aac ctg cgc gtc tac cgg gtg gca cag cgg            3550
Gln Ile Ala Ala Asp Pro Asn Leu Arg Val Tyr Arg Val Ala Gln Arg
770                 775                 780                 785 gga cgc tgacccacgt cacgccggct cggcccgtgc ggggggcgcag ggcgccgatc            3606
Gly Arg gtctctgcat cgccggtcag ccggggcctg cgtcgaccgg cggcggccgg tcgacgcccg          3666
cgtcccggcg cagcgactgg ctgaagcgcc aggcgtcggc ggcccggggc aggttgttga          3726
acatcacgta cgccgggccg ccgtcgagga tgccggcgag gtgtgccagc tcggcatccg          3786
tgtacacatg ccgggcgccg gtgatgccgt gcagccggta ataggccatc ggcgtcagac          3846
tgcggcgcag gaacgggtcg gcggcgtggg tcaggtccag ctcctggcac aagccctcga          3906
ccacctcgtc cggccacggg ccgcgcggct cccacaacag ccggacaccg gccggccggc          3966
gcgctcgggc gcagaactca cgcagtcgcg cgatggcggg ttcggtcggc cggaaactcg          4026
ccgggcactg cag                                                             4039
```

<210> SEQ ID NO 8
<211> LENGTH: 787
<212> TYPE: PRT
<213> ORGANISM: Artificial Sequence
<220> FEATURE:
<223> OTHER INFORMATION: Description of Artificial Sequence:Actinoplanes
    utahensis echinocandin B (ECB) deacylase protein mutant M-15
    transcribed from gene created by in vitro heteroduplex formation
    followed by in vivo repair

<400> SEQUENCE: 8

Val Thr Ser Ser Tyr Met Arg Leu Lys Ala Ala Ala Ile Ala Phe Gly
 1               5                  10                  15

Val Ile Val Ala Thr Ala Ala Val Pro Ser Pro Ala Ser Gly Arg Glu
            20                  25                  30

His Asp Gly Gly Tyr Ala Ala Leu Ile Arg Arg Ala Ser Tyr Gly Val
        35                  40                  45

Pro His Ile Thr Ala Asp Asp Phe Gly Ser Leu Gly Phe Gly Val Gly
    50                  55                  60

Tyr Val Gln Ala Glu Asp Asn Ile Cys Val Ile Ala Glu Ser Val Val
65                  70                  75                  80

Thr Ala Asn Gly Glu Arg Ser Arg Trp Phe Gly Ala Thr Gly Pro Asp
                85                  90                  95

-continued

```
Asp Ala Asp Val Arg Ser Asp Leu Phe His Arg Lys Ala Ile Asp Asp
            100                 105                 110
Arg Val Ala Glu Arg Leu Leu Glu Gly Pro Arg Asp Gly Val Arg Ala
        115                 120                 125
Pro Ser Asp Asp Val Arg Asp Gln Met Arg Gly Phe Val Ala Gly Tyr
    130                 135                 140
Asn His Phe Leu Arg Arg Thr Gly Val His Arg Leu Thr Asp Pro Ala
145                 150                 155                 160
Cys Arg Gly Lys Ala Trp Val Arg Pro Leu Ser Glu Ile Asp Leu Trp
                165                 170                 175
Arg Thr Ser Trp Asp Ser Met Val Arg Ala Gly Ser Gly Ala Leu Leu
            180                 185                 190
Asp Gly Ile Val Ala Ala Thr Pro Thr Ala Ala Gly Pro Ala Ser
        195                 200                 205
Ala Pro Glu Ala Pro Asp Ala Ala Ile Ala Ala Leu Asp Gly
    210                 215                 220
Thr Ser Ala Gly Ile Gly Ser Asn Ala Tyr Gly Leu Gly Ala Gln Ala
225                 230                 235                 240
Thr Val Asn Gly Ser Gly Met Val Leu Ala Asn Pro His Phe Pro Trp
                245                 250                 255
Gln Gly Ala Ala Arg Phe Tyr Arg Met His Leu Lys Val Pro Gly Arg
            260                 265                 270
Tyr Asp Val Glu Gly Ala Ala Leu Ile Gly Asp Pro Ile Ile Gly Ile
        275                 280                 285
Gly His Asn Arg Thr Val Ala Trp Ser His Thr Val Ser Thr Ala Arg
    290                 295                 300
Arg Phe Val Trp His Arg Leu Ser Leu Val Pro Gly Asp Pro Thr Ser
305                 310                 315                 320
Tyr Tyr Val Asp Gly Arg Pro Glu Arg Met Arg Ala Arg Thr Val Thr
                325                 330                 335
Val Gln Thr Gly Ser Gly Pro Val Ser Arg Thr Phe His Asp Thr Arg
            340                 345                 350
Tyr Gly Pro Val Ala Val Met Pro Gly Thr Phe Asp Trp Thr Pro Ala
        355                 360                 365
Thr Ala Tyr Ala Ile Thr Asp Val Asn Ala Gly Asn Asn Arg Ala Phe
    370                 375                 380
Asp Gly Trp Leu Arg Met Gly Gln Ala Lys Asp Val Arg Ala Leu Lys
385                 390                 395                 400
Ala Val Leu Asp Arg His Gln Phe Leu Pro Trp Val Asn Val Ile Ala
                405                 410                 415
Ala Asp Ala Arg Gly Glu Ala Leu Tyr Gly Asp His Ser Val Pro
            420                 425                 430
Arg Val Thr Gly Ala Leu Ala Ala Cys Ile Pro Ala Pro Phe Gln
        435                 440                 445
Pro Leu Tyr Ala Ser Ser Gly Gln Ala Val Leu Asp Gly Ser Arg Ser
    450                 455                 460
Asp Cys Ala Leu Gly Ala Asp Pro Asp Ala Ala Val Pro Gly Ile Leu
465                 470                 475                 480
Gly Pro Ala Ser Leu Pro Val Arg Phe Arg Asp Asp Tyr Val Thr Asn
                485                 490                 495
Ser Asn Asp Ser His Trp Leu Ala Ser Pro Ala Ala Pro Leu Glu Gly
            500                 505                 510
```

```
Phe Pro Arg Ile Leu Gly Asn Glu Arg Thr Pro Arg Ser Leu Arg Thr
            515                 520                 525

Arg Leu Gly Leu Asp Gln Ile Gln Gln Arg Leu Ala Gly Thr Asp Gly
        530                 535                 540

Leu Pro Gly Lys Gly Phe Thr Thr Ala Arg Leu Trp Gln Val Met Phe
545                 550                 555                 560

Gly Asn Arg Met His Gly Ala Glu Leu Ala Arg Asp Asp Leu Val Ala
                565                 570                 575

Leu Cys Arg Arg Gln Pro Thr Ala Thr Ala Ser Asn Gly Ala Ile Val
            580                 585                 590

Asp Leu Thr Ala Ala Cys Thr Ala Leu Ser Arg Phe Asp Glu Arg Ala
        595                 600                 605

Asp Leu Asp Ser Arg Gly Ala His Leu Phe Thr Glu Phe Ala Leu Ala
    610                 615                 620

Gly Gly Ile Arg Phe Ala Asp Thr Phe Glu Val Thr Asp Pro Val Arg
625                 630                 635                 640

Thr Pro Arg Arg Leu Asn Thr Thr Asp Pro Arg Val Arg Thr Ala Leu
                645                 650                 655

Ala Asp Ala Val Gln Arg Leu Ala Gly Ile Pro Leu Asp Ala Lys Leu
            660                 665                 670

Gly Asp Ile His Thr Asp Ser Arg Gly Glu Arg Ile Pro Ile His
        675                 680                 685

Gly Gly Arg Gly Glu Ala Gly Thr Phe Asn Val Ile Thr Asn Pro Leu
    690                 695                 700

Val Pro Gly Val Gly Tyr Pro Gln Val Val His Gly Thr Ser Phe Val
705                 710                 715                 720

Met Ala Val Glu Leu Gly Pro His Gly Pro Ser Gly Arg Gln Ile Leu
                725                 730                 735

Thr Tyr Ala Gln Ser Thr Asn Pro Asn Ser Pro Trp Tyr Ala Asp Gln
            740                 745                 750

Thr Val Leu Tyr Ser Arg Lys Gly Trp Asp Thr Ile Lys Tyr Thr Glu
        755                 760                 765

Ala Gln Ile Ala Ala Asp Pro Asn Leu Arg Val Tyr Arg Val Ala Gln
    770                 775                 780

Arg Gly Arg
785

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:forward
      primer corresponding to the vector sequence of pGFP
      plasmid (Aequorea victoria green fluorescent
      protein)

<400> SEQUENCE: 9
ccgactggaa agcgggcagt g                                           21

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence:reverse
      primer corresponding to the vector sequence of pGFP
      plasmid (Aequorea victoria green fluorescent
      protein)
```

```
<400> SEQUENCE: 10
cggggctggc ttaactatgc gg                                            22

<210> SEQ ID NO 11
<211> LENGTH: 4
<212> TYPE: PRT
<213> ORGANISM: Artificial Sequence
<220> FEATURE:
<221> NAME/KEY: MOD_RES
<222> LOCATION: (1)
<223> OTHER INFORMATION: Xaa = succinyl-Ala
<221> NAME/KEY: MOD_RES
<222> LOCATION: (4)
<223> OTHER INFORMATION: Xaa = Phe-p-nitroanilide
<223> OTHER INFORMATION: Description of Artificial Sequence:Bacillus
      subtilis subtilisin E thermostability assay
      substrate

<400> SEQUENCE: 11

Xaa Ala Pro Xaa
 1
```